(12) United States Patent
Hafner et al.

(10) Patent No.: US 9,180,098 B2
(45) Date of Patent: *Nov. 10, 2015

(54) COMPOSITIONS WITH REDUCED DIMER FORMATION

(75) Inventors: Roderick Peter Hafner, Oxford (GB); Paul Laidler, Oxford (GB)

(73) Assignee: Circassia Limited, Oxford (GB)

( * ) Notice: Subject to any disclaimer, the term of this patent is extended or adjusted under 35 U.S.C. 154(b) by 381 days.

This patent is subject to a terminal disclaimer.

(21) Appl. No.: 13/131,505

(22) PCT Filed: Nov. 27, 2009

(86) PCT No.: PCT/GB2009/002767
§ 371 (c)(1),
(2), (4) Date: Oct. 5, 2011

(87) PCT Pub. No.: WO2010/061193
PCT Pub. Date: Jun. 3, 2010

(65) Prior Publication Data
US 2012/0014978 A1  Jan. 19, 2012

(30) Foreign Application Priority Data
Nov. 28, 2008  (GB) .................................. 0821806.7

(51) Int. Cl.
| | |
|---|---|
| *A61K 38/00* | (2006.01) |
| *A61K 38/04* | (2006.01) |
| *A61K 39/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *A61K 9/19* | (2006.01) |
| *A61K 39/35* | (2006.01) |
| *A61K 47/10* | (2006.01) |
| *A61K 47/26* | (2006.01) |

(52) U.S. Cl.
CPC ............... *A61K 9/19* (2013.01); *A61K 39/0008* (2013.01); *A61K 39/35* (2013.01); *A61K 47/10* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 4,442,212 A | 4/1984 | Briggs | |
| 4,855,407 A | 8/1989 | Wang | |
| 6,204,036 B1 | 3/2001 | Metzner et al. | |
| 7,462,596 B2 * | 12/2008 | Larsen et al. | ............. 514/1.1 |
| 8,551,492 B2 | 10/2013 | Hafner et al. | |
| 8,551,493 B2 * | 10/2013 | Hafner et al. | ............. 424/185.1 |
| 2005/0203017 A1 | 9/2005 | Hobson et al. | |
| 2006/0024334 A1 | 2/2006 | Larche et al. | |
| 2008/0293624 A1 | 11/2008 | Hageman et al. | |

FOREIGN PATENT DOCUMENTS

| | | |
|---|---|---|
| CN | 1283997 | 2/2001 |
| EP | 0044532 A2 | 1/1982 |
| EP | 1958645 A1 | 8/2008 |
| EP | 2079481 B1 | 7/2009 |
| EP | 2190473 B1 | 6/2010 |
| EP | 2373293 B8 | 10/2011 |
| JP | 2007-277094 | 10/2007 |
| WO | 93/08279 A1 | 4/1993 |
| WO | 93/21321 A2 | 10/1993 |
| WO | 94/10314 A1 | 5/1994 |
| WO | 94/16068 A2 | 7/1994 |
| WO | 96/07428 A1 | 3/1996 |
| WO | 99/32135 A1 | 7/1999 |
| WO | 99/34826 A1 | 7/1999 |
| WO | 02/17956 A2 | 3/2002 |
| WO | 03/042344 A2 | 5/2003 |
| WO | 03/047618 A2 | 6/2003 |
| WO | 03/093299 A2 | 11/2003 |
| WO | 2005/047323 A1 | 5/2005 |
| WO | 2006/017773 A1 | 2/2006 |
| WO | 2006/083906 A2 | 8/2006 |
| WO | 2006/127910 A2 | 11/2006 |
| WO | 2008098749 A2 | 8/2008 |
| WO | 2008/115428 A2 | 9/2008 |
| WO | 2008/145998 A1 | 12/2008 |
| WO | 2009/022155 A2 | 2/2009 |

OTHER PUBLICATIONS

Tang et al. 'Design of freeze-drying processes for pharmaceuticals:practical advice.' Pharm. Res. 21(2):191-200, 2004.*
Bedu-Addo et al. 'Understanding Lyophilization Formulation Development.' Pharmaceutical Technology, Feb. 1, 2004.*
Gotte, Giovanni et al., "Oligomerization of ribonuclease A under reducing conditions," Biochimica et Biophysica Acta, vol. 1784:638-650 (2008).
International Search Report and Written Opinion for Application No. PCT/GB2009/002767, dated Apr. 29, 2011.
Great Britain Search Report for Application No. GB0821806.7.

(Continued)

*Primary Examiner* — Nora Rooney
(74) *Attorney, Agent, or Firm* — Nelson Mullins Riley & Scarborough LLP; Jane E. Remillard, Esq.; Jeanne M. DiGiorgio, Esq.

(57) ABSTRACT

The present invention relates to the use of a non-reducing carbohydrate or carbohydrate derivative and at least one agent which inhibits dimer formation in a freeze-dried composition comprising at least one peptide that contains a free cysteine residue, to provide a freeze-dried composition with improved long-term storage stability.

9 Claims, 29 Drawing Sheets

(56) References Cited

OTHER PUBLICATIONS

Akers, Michael J., "Antioxidants in Pharmaceutical Products," Journal of Parenteral Science and Technology, vol. 36 (5):222-228 (1982).
Akers, Michael J. et al., "Formulation Development of Protein Dosage Forms," Pharmaceutical Biotechnology, vol. 14, Development and Manufacture of Protein Pharmaceuticals, Steven L. Nail (Ed.), Kluwer Academic/Plenum Publishers, New York, pp. 47, 65-69 (2002).
Akers, Michael J. et al., "Peptides and Proteins as Parenteral Solutions," Pharmaceutical Formulation Development of Peptides and Proteins, Sven Frokjaer (Ed.), Taylor & Francis, Inc., Philadelphia, PA, Chapter 8, pp. 145-177 (2000).
Daniel, Dylan et al., "Protection of nonobese diabetic mice from diabetes by intranasal or subcutaneous administration of insulin peptide B-(9-23)," Proc. Natl. Acad. Sci. USA, vol. 93:956-960 (1996).
Higgins, Paul J. et al., "Suppression of Experimental Autoimmune Encephalomyelitis by Oral Administration of Myelin Basic Protein and Its Fragments," The Journal of Immunology, vol. 140(2):440-445 (1988).
Hoyne, Gerard F. et al., "Inhibition of T Cell and Antibody Responses to House Dust Mite Allergen by Inhalation of the Dominant T Cell Epitope in Naive and Sensitized Mice," J. Exp. Med., vol. 178:1783-1788 (1993).
Kent, Sally C. et al., "Expanded T cells from pancreatic lymph nodes of type 1 diabetic subjects recognize an insulin epitope," Nature, vol. 435:224-228 (2005).
Knepp, Victoria M. et al., "Identification of Antioxidants for Prevention of Peroxide-Mediated Oxidation of Recombinant Human Ciliary Neurotrophic Factor and Recombinant Human Nerve Growth Factor," PDA Journal of Pharmaceutical Sciences & Technology, vol. 50(3):163-171 (1996).
Muller, Ulrich et al., "Successful immunotherapy with T-cell epitope peptides of bee venom phospholipase A2 induces specific T-cell anergy in patients allergic to bee venom," J. Allergy Clin. Immunol., vol. 101(6 pt. 1):747-754 (1998).
Prakken, Berent J. et al., "Peptide-induced nasal tolerance for the mycobacterial heat shock protein 60 T cell epitope in rats suppresses both adjuvant arthritis and nonmicrobially induced experimental arthritis," Proc. Natl. Acad. Sci. USA, vol. 94:3284-3289 (1997).
Staines, N.A. et al., "Mucosal tolerance and suppression of collagen-induced arthritis (CIA) induced by nasal inhalation of synthetic peptide 184-198 of bovine type II collagen (CII) expressing a dominant T cell epitope," Clin. Exp. Immunol., vol. 103:368-375 (1996).
Tian, Jide et al., "Nasal Administration Of Glutamate Decarboxylase (GAD65) Peptides Induces Th2 Responses and Prevents Murine Insulin-dependent Diabetes," J. Exp. Med., vol. 183:1561-1567 (1996).
Zhu, Xiaojiu et al., "T Cell Epitope Mapping of Ragweed Pollen Allergen *Ambrosia artemisiifolia* (Amb a 5) and *Ambrosia trifida* (Amb t 5) and the Role of Free Sulfhydryl Groups in T Cell Recognition," The Journal of Immunology, vol. 155:5064-5073 (1995).
Certified copy of GB Application No. 0710529.9, 105 pages, dated Jun. 1, 2007.
Extract from the Register of European Patents, EP2079481, 2 pages (2013).
Notice of Opposition, EP2190473, Circassia Limited, 32 pages, dated Jan. 16, 2013.
European Patent No. 2190473, Circassia Limited, Peptide with Reduced Dimer Formation, Facts & Arguments in Support of Opposition by Strawman Limited, 25 pages, dated Oct. 15, 2013.
European Search Report for Application No. 13176176.9, 8 pages, dated Sep. 12, 2013.
Japanese Office Action for Application No. 538050/2001, 4 pages, dated Dec. 17, 2013.
Akers, Michael J., "Excipient—Drug Interactions in Parenteral Formulations," Journal of Pharmaceutical Sciences, vol. 91(11)2283-2300 (2002).
Andreu, David et al., "Formation of Disulfide Bonds in Synthetic Peptides and Proteins," Methods in Molecular Biology, vol. 35, Peptide Synthesis Protocols, M.W. Pennington (Ed.), Humana Press Inc., Totowa, NJ, Chapter 7, pp. 91-169 (1994).
Jain, Nishant Kumar et al., "Effect of trehalose on protein structure," Protein Science, vol. 18(1):24-36 (2009).
Kaushik, Jai K. et al., "Why Is Trehalose an Exceptional Protein Stabilizer?" The Journal of Biological Chemistry, vol. 278(29):26458-26465 (2003).
Rowe, Raymond C. et al., Handbook of Pharmaceutical Excipients, Sixth Edition, Pharmaceutical Press, London, 917 pages (2009).
Wang, Wei, "Instability, stabilization, and formulation of liquid protein pharmaceuticals," International Journal of Pharmaceutics, vol. 185:129-188 (1999).
Wang, Wei, "Lyophilization and development of solid protein pharmaceuticals," International Journal of Pharmaceutics, vol. 203:1-60 (2000).
Notice of Opposition, Patent No. EP2373293, 7 pages, dated Mar. 17, 2014.
Facts & Arguments in Support of Opposition by Stawman Limited, Patent No. EP2373293, 41 pages, dated Mar. 17, 2014.
Response to Opposition for Patent No. EP2190473, 16 pages, dated Jun. 2, 2014.
Oldfield, W. L. et al., "Allergen-derived T cell peptide-induced late asthmatic reactions precede the induction of antigen-specific hyporesponsiveness in atopic allergic asthmatic subjects," American Association of Immunologists, 6 pages (2001).
Goolcharran, Chimanlall et al., "Chemical Pathways of Peptide and Protein Degradation," Pharmaceutical Formulation Development of Peptides and Proteins, Chapter 5:70-88(2000).
Morin, Leo, et al., "Creatine Kinase: Re-examination of Optimum Reaction Conditions," Clinical Chemistry, vol. 23 (9):1569-1575(1977).
Response to Opposition for Patent No. EP2373293, 44 pages, dated Dec. 16, 2014.
Declaration of Professor Geoffrey Lee, 14 pages, Opposition for European Patent No. EP2373293, dated Dec. 13, 2014.
Curriculum Vitae of Professor Geoffrey Lee, 4 pages, Opposition for European Patent No. EP2373293, dated Dec. 13, 2014.

* cited by examiner

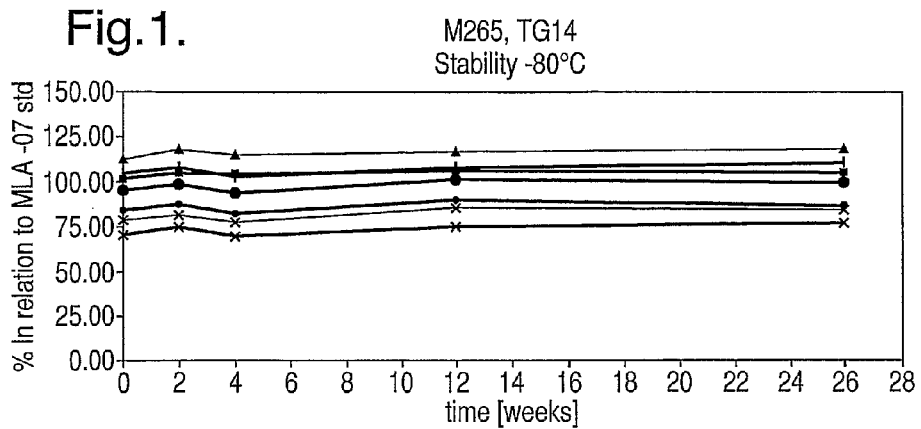
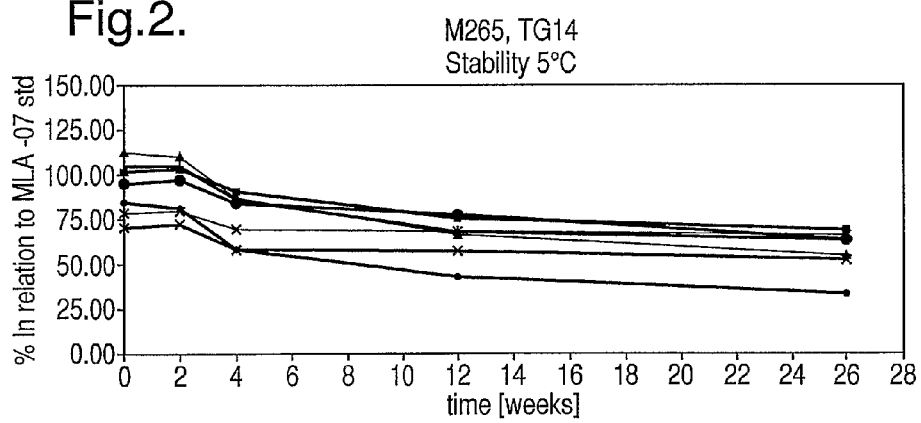
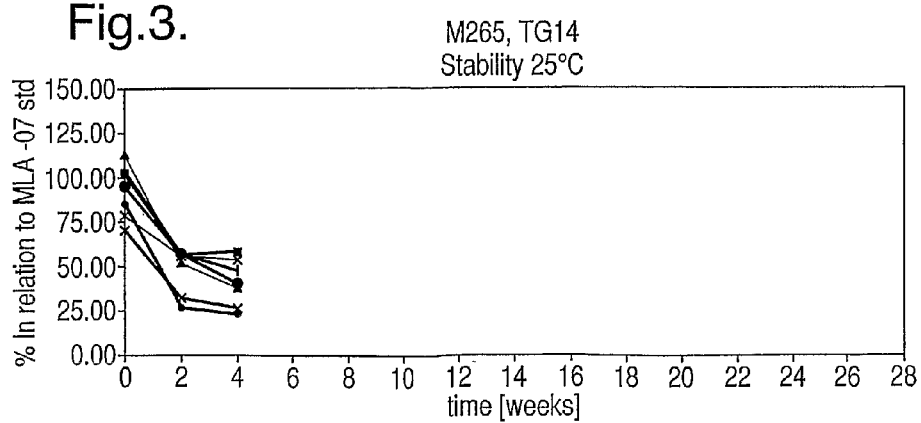

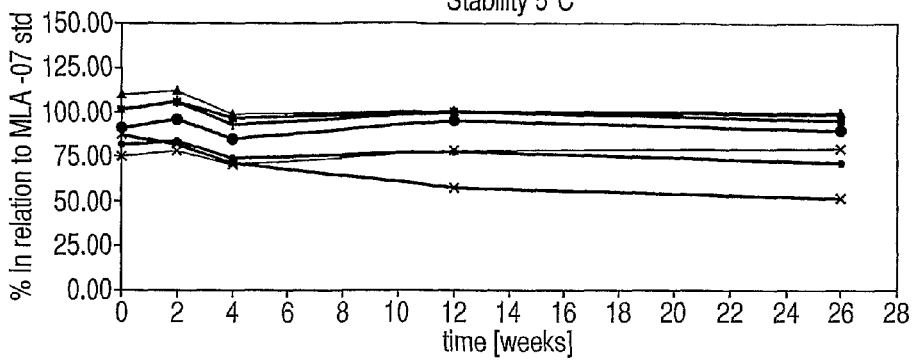
Fig.10. M260, TG14, Met5 Stability 5°C
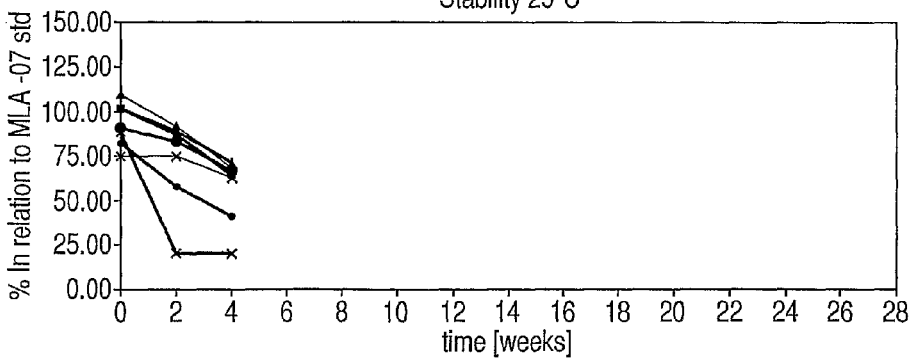
Fig.11. M260, TG14, Met5 Stability 25°C
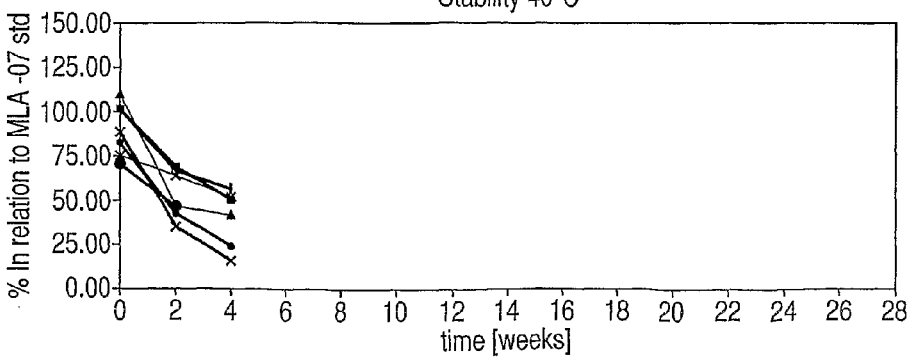
Fig.12. M260, TG14, Met5 Stability 40°C

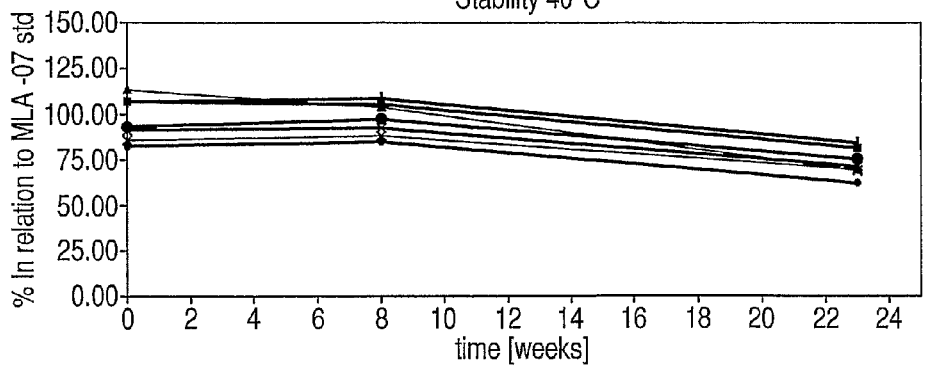
Fig. 19. T250mM, TG46, Met5 Stability 40°C
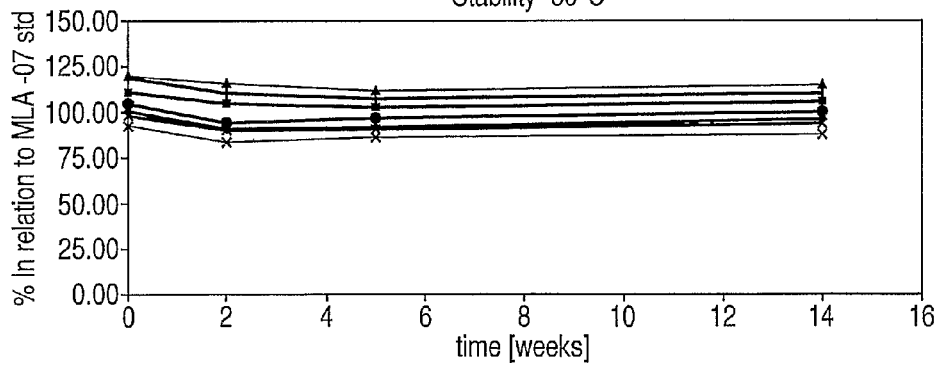
Fig. 20. G95, T165, TG46, Met5 Stability -80°C
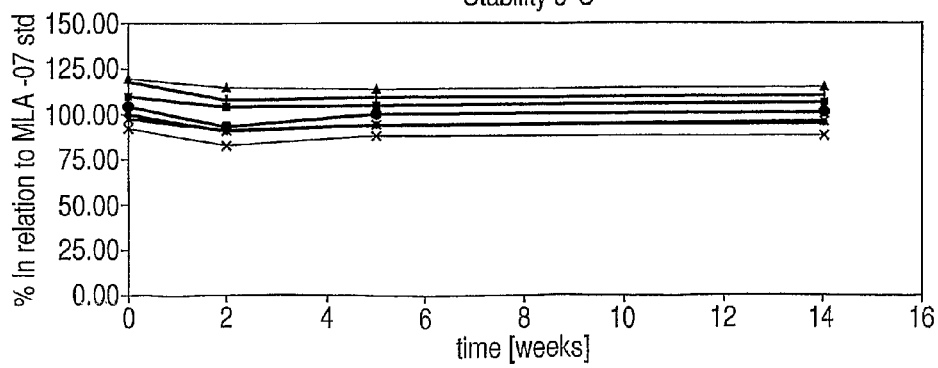
Fig. 21. G95, T165, TG46, Met5 Stability 5°C

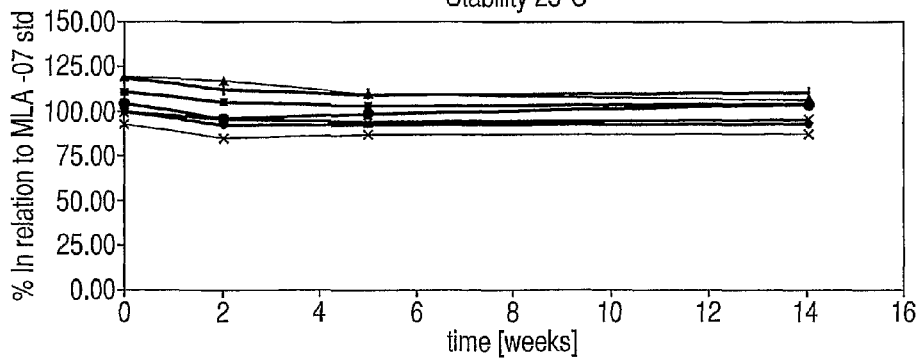
Fig.22. G95, T165, TG46, Met5 Stability 25°C
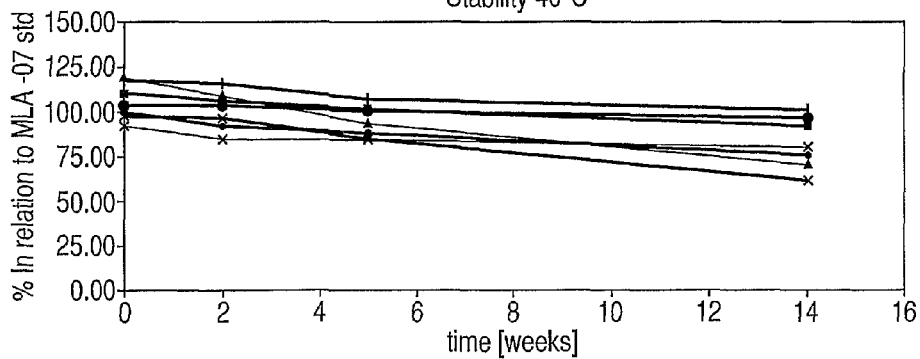
Fig.23. G95, T165, TG46, Met5 Stability 40°C
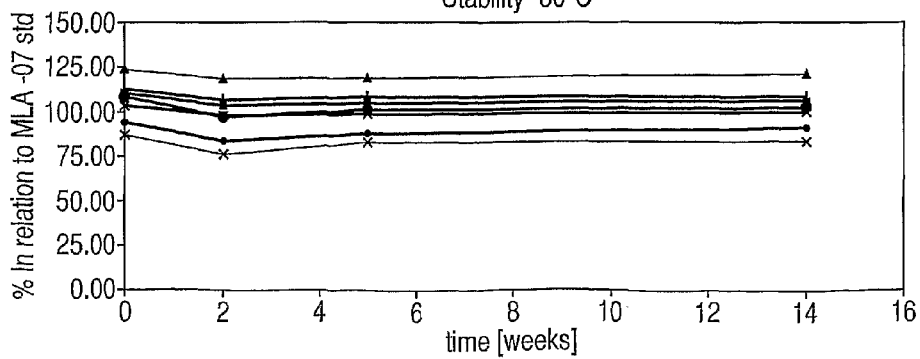
Fig.24. G78, S182, TG46, Met5 Stability -80°C

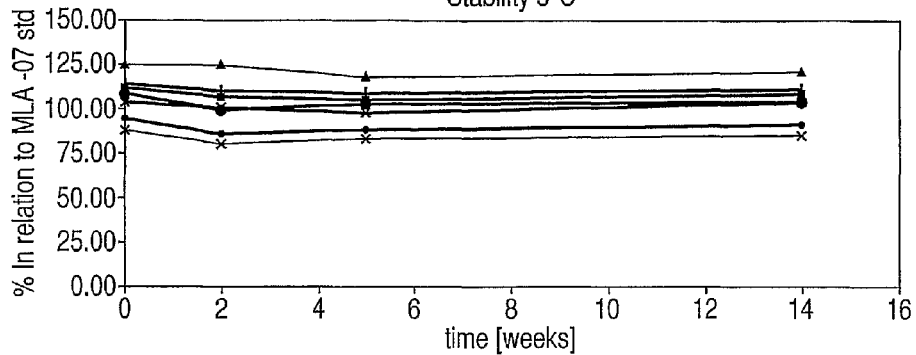
Fig.25. G78, S182, TG46, Met5 Stability 5°C
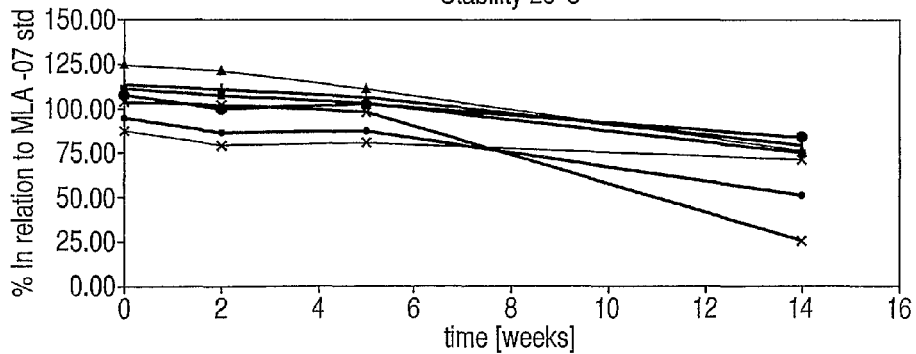
Fig.26. G78, S182, TG46, Met5 Stability 25°C
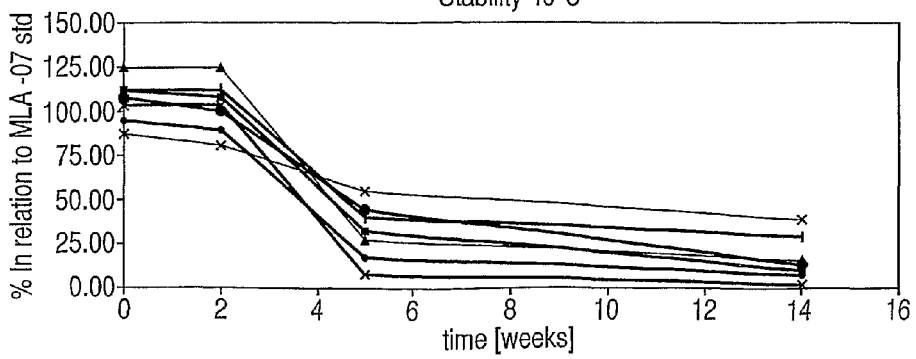
Fig.27. G78, S182, TG46, Met5 Stability 40°C

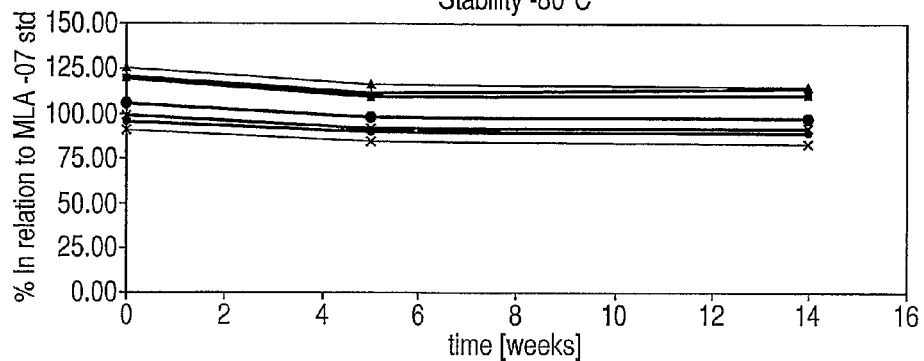
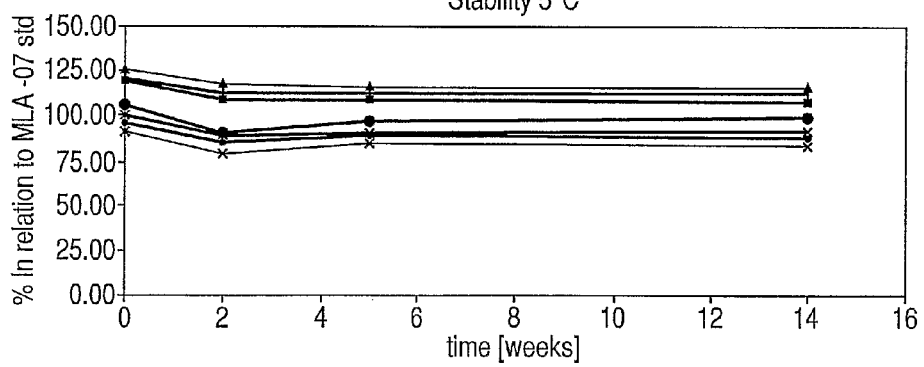
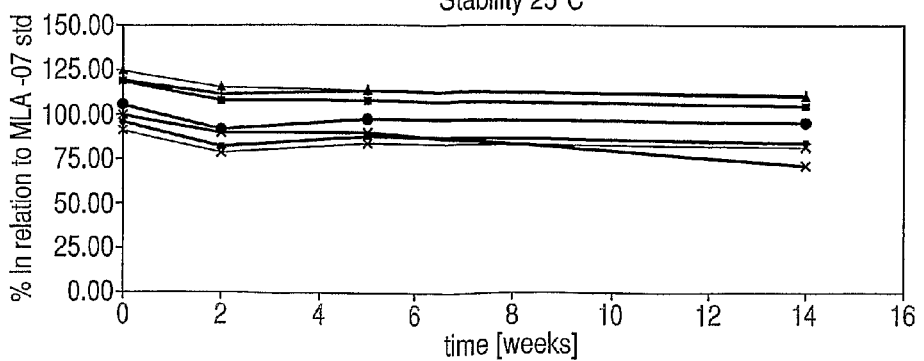

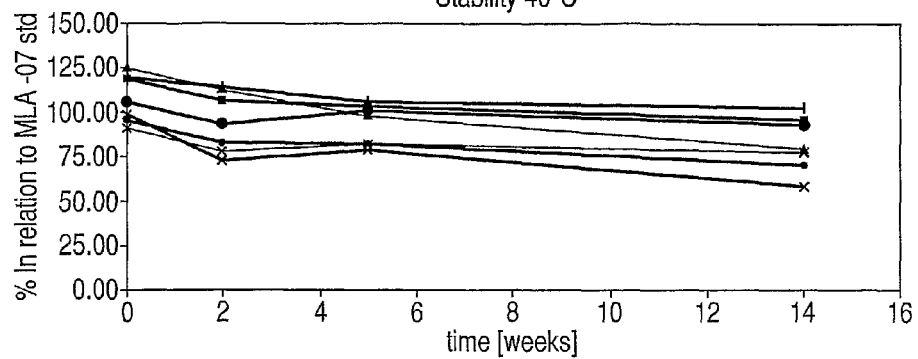
Fig.31. M100, T160, TG46, Met5 Stability 40°C
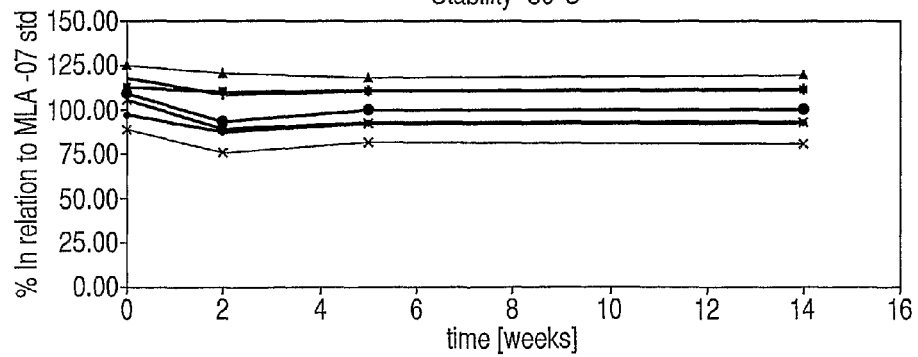
Fig.32. M110, S150, TG46, Met5 Stability -80°C
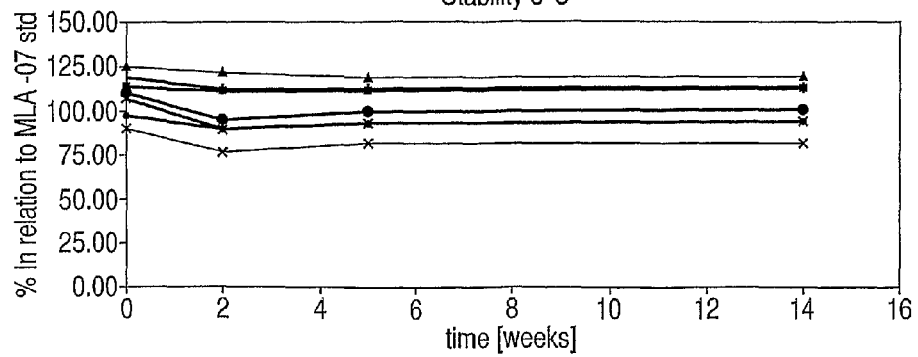
Fig.33. M110, S150, TG46, Met5 Stability 5°C

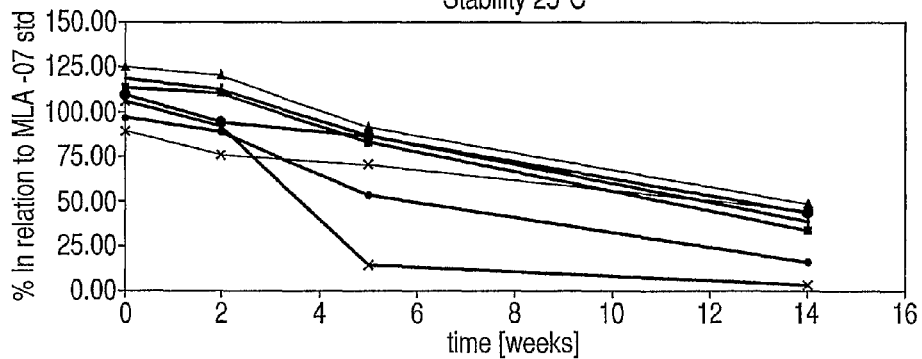
Fig.34. M110, S150, TG46, Met5 Stability 25°C
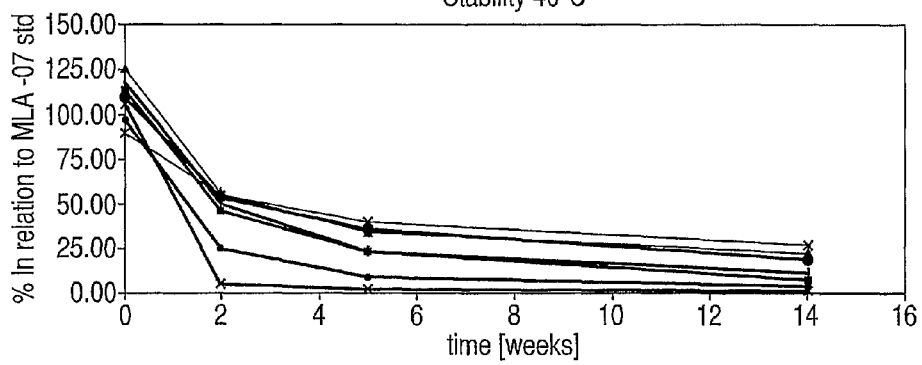
Fig.35. M110, S150, TG46, Met5 Stability 40°C
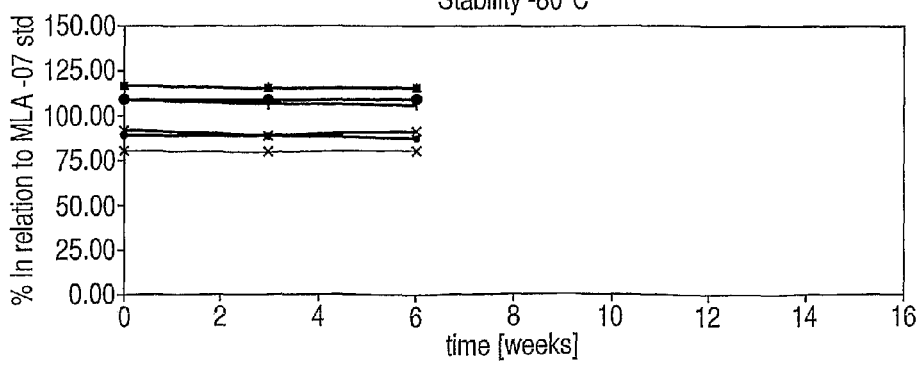
Fig.36. M245, T10, TG46, Met5 Stability -80°C

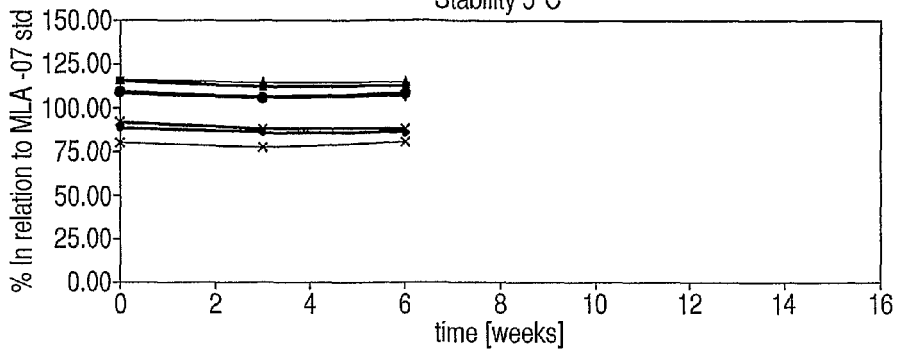
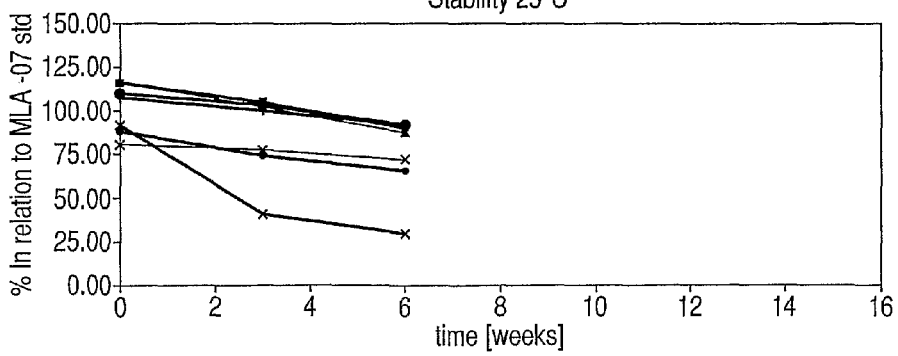
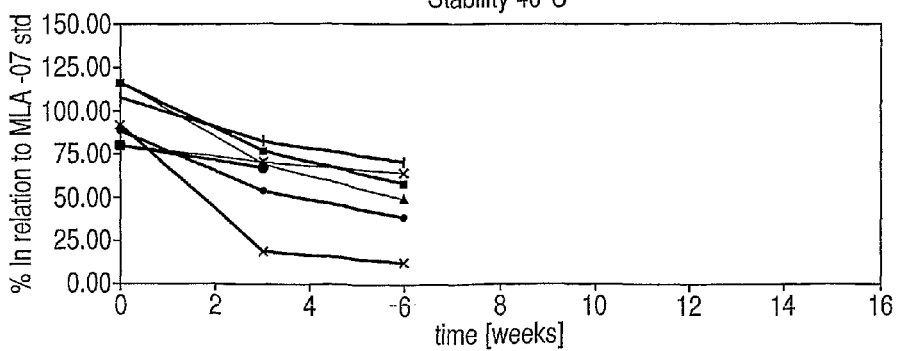

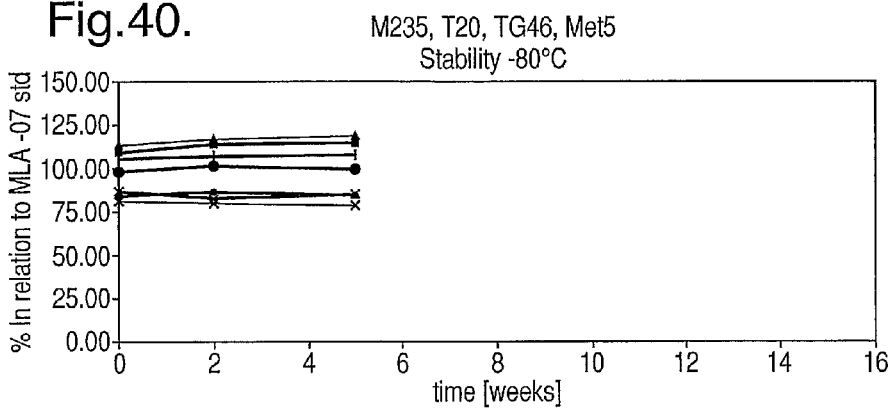
Fig.40. M235, T20, TG46, Met5 Stability -80°C
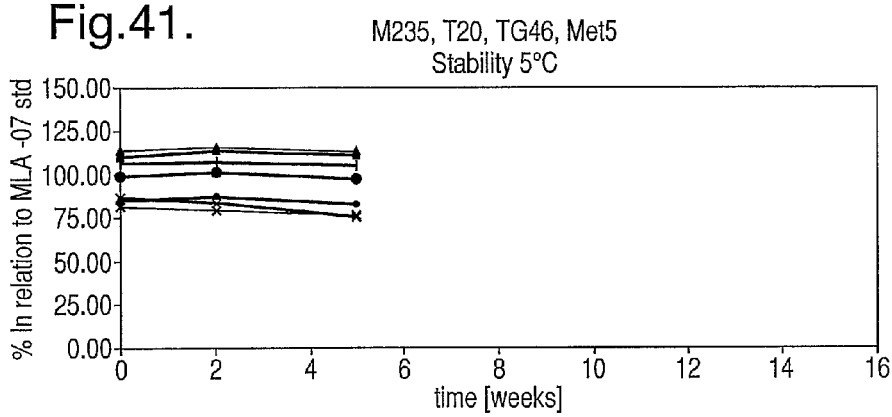
Fig.41. M235, T20, TG46, Met5 Stability 5°C
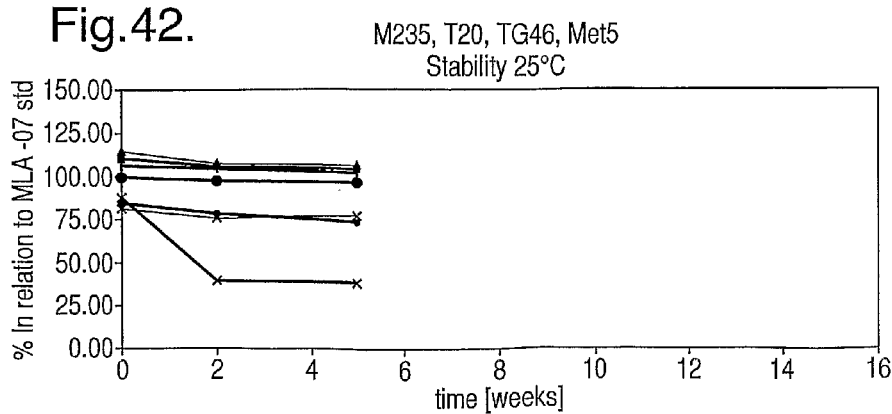
Fig.42. M235, T20, TG46, Met5 Stability 25°C

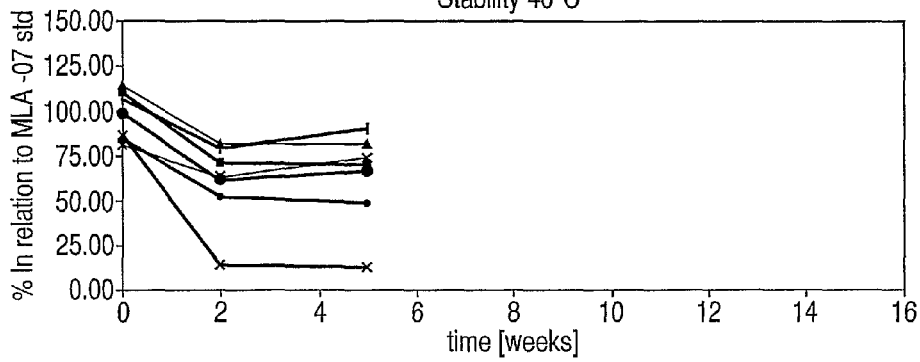
Fig.43. M235, T20, TG46, Met5 Stability 40°C
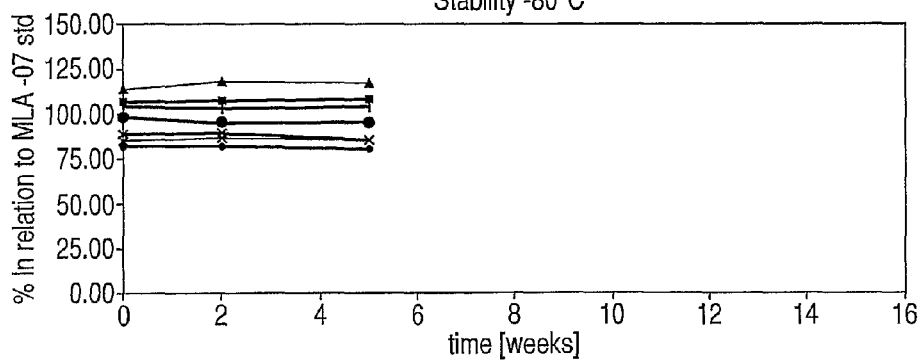
Fig.44. M225, T30, TG46, Met5 Stability -80°C
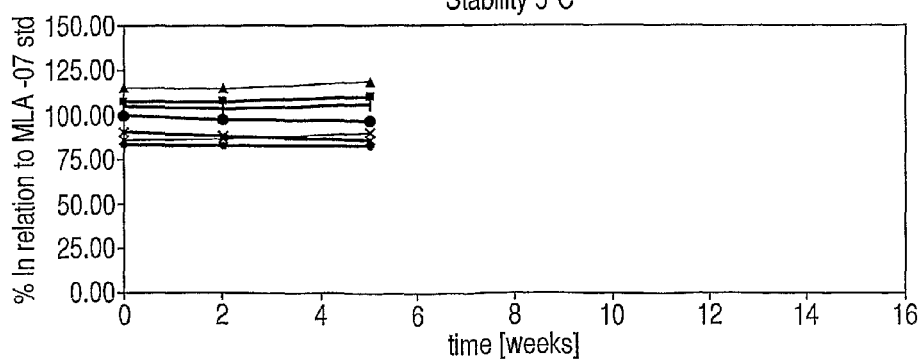
Fig.45. M225, T30, TG46, Met5 Stability 5°C

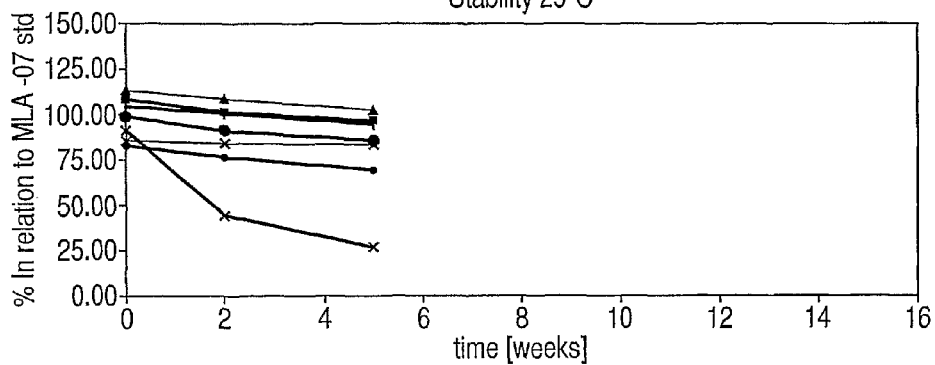
Fig.46. M225, T30, TG46, Met5 Stability 25°C
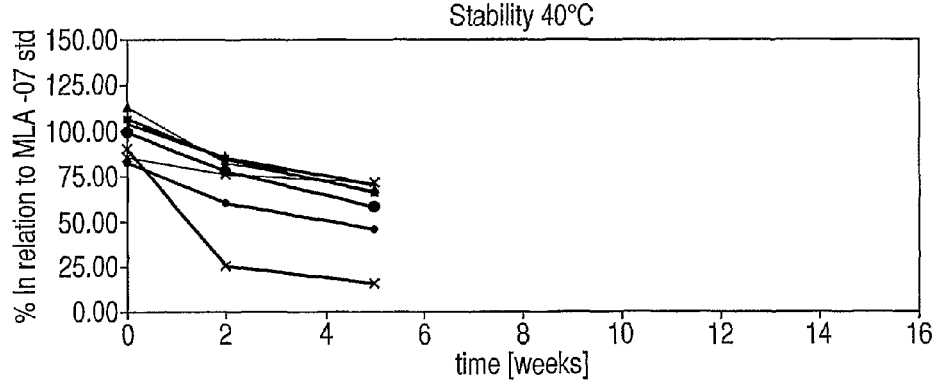
Fig.47. M225, T30, TG46, Met5 Stability 40°C
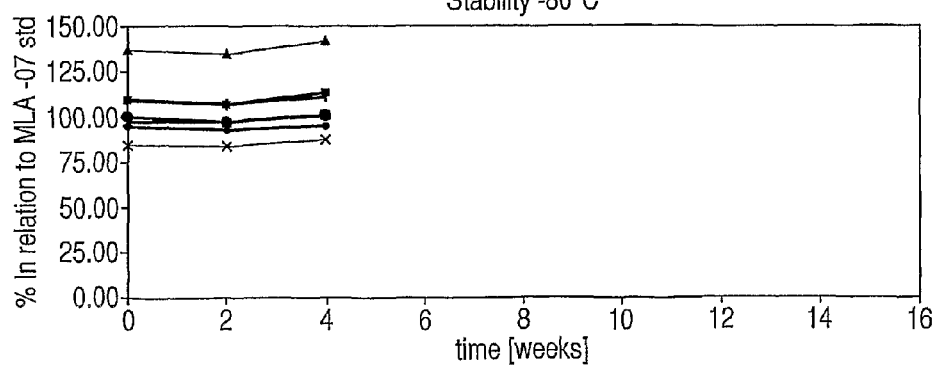
Fig.48. M245, T10, TG46, Met5, EDTA 0,5 Stability -80°C

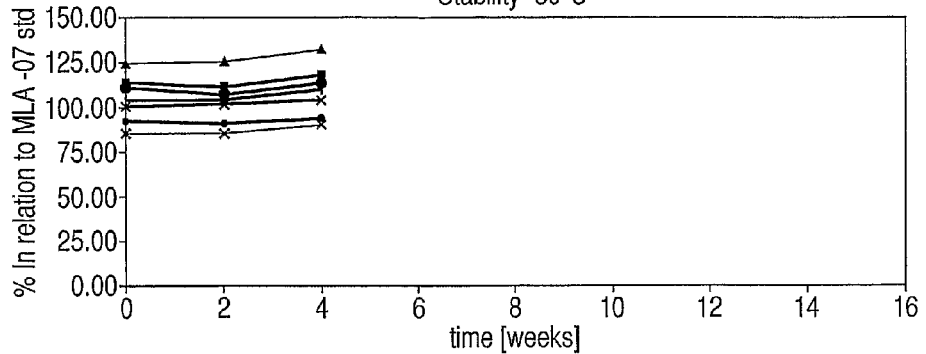
Fig.52. M235, T20, TG46, Met5, EDTA 0,5 Stability -80°C
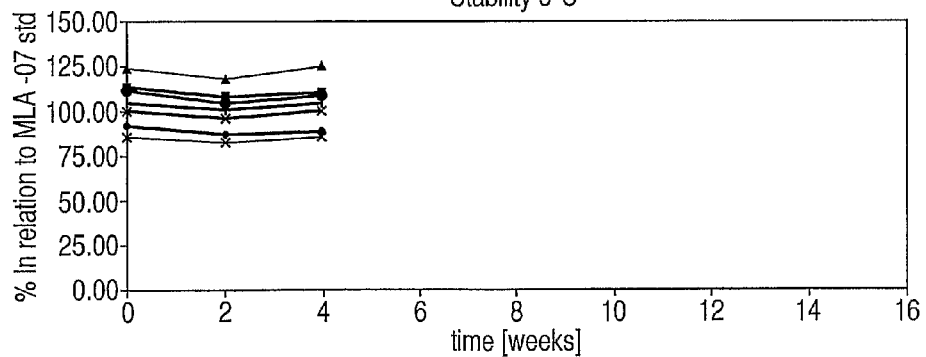
Fig.53. M235, T20, TG46, Met5, EDTA 0,5 Stability 5°C
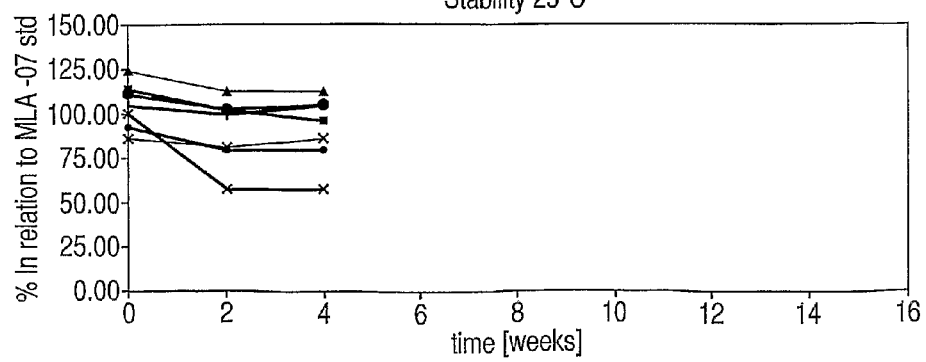
Fig.54. M235, T20, TG46, Met5, EDTA 0,5 Stability 25°C

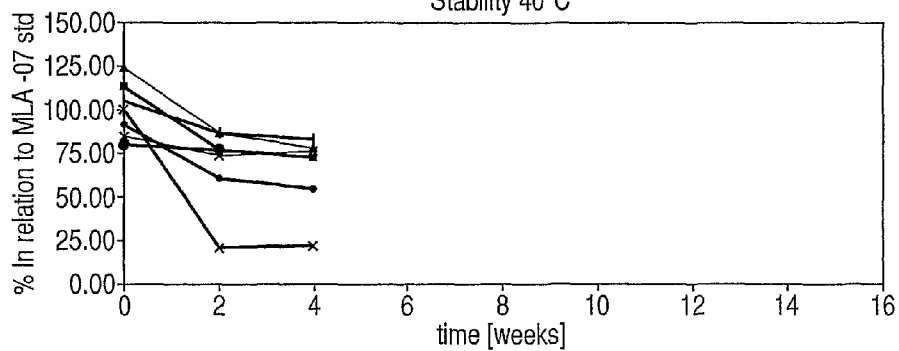
Fig.55. M235, T20, TG46, Met5, EDTA 0,5 Stability 40°C
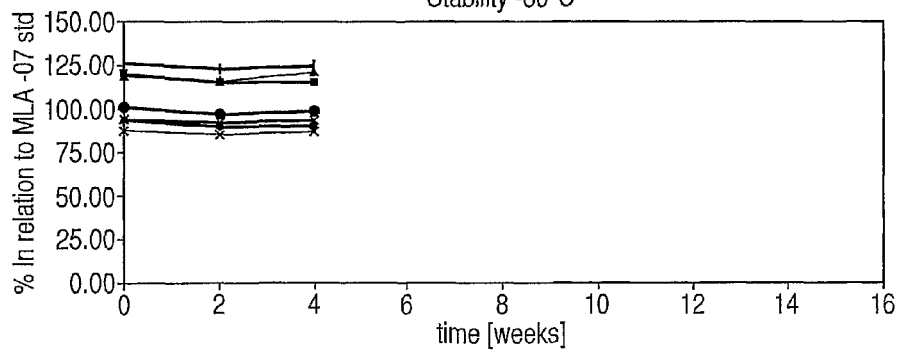
Fig.56. M225, T30, TG46, Met5, EDTA 0,5 Stability -80°C
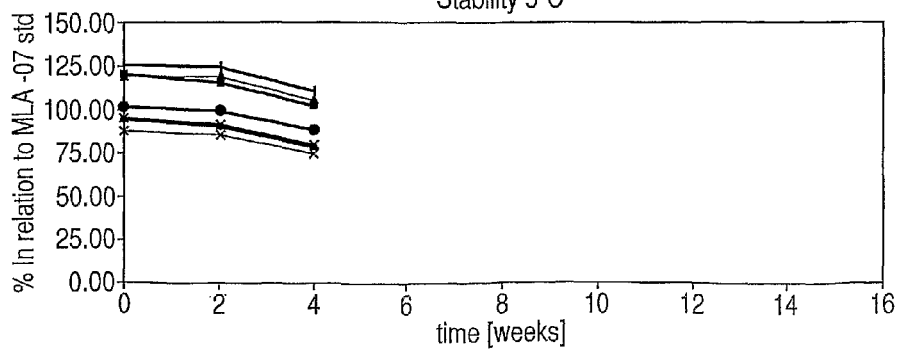
Fig.57. M225, T30, TG46, Met5, EDTA 0,5 Stability 5°C

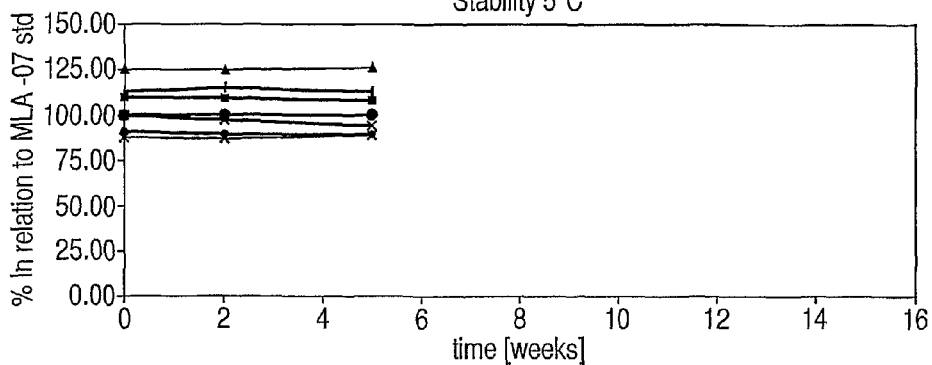
Fig.61. M245, S10, TG46, Met5 Stability 5°C
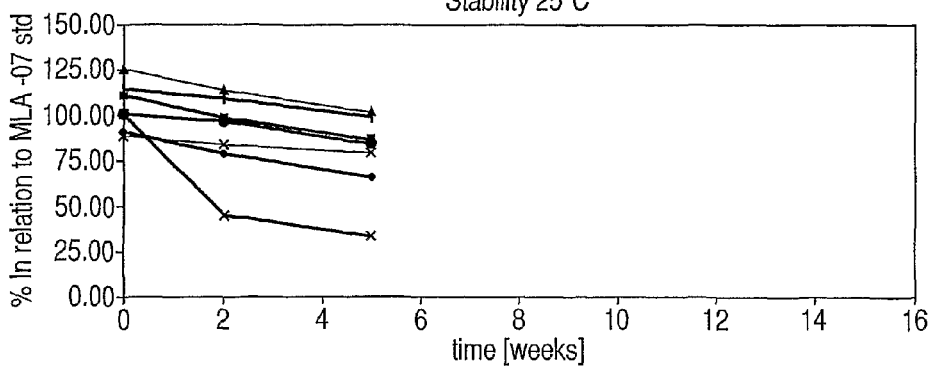
Fig.62. M245, S10, TG46, Met5 Stability 25°C
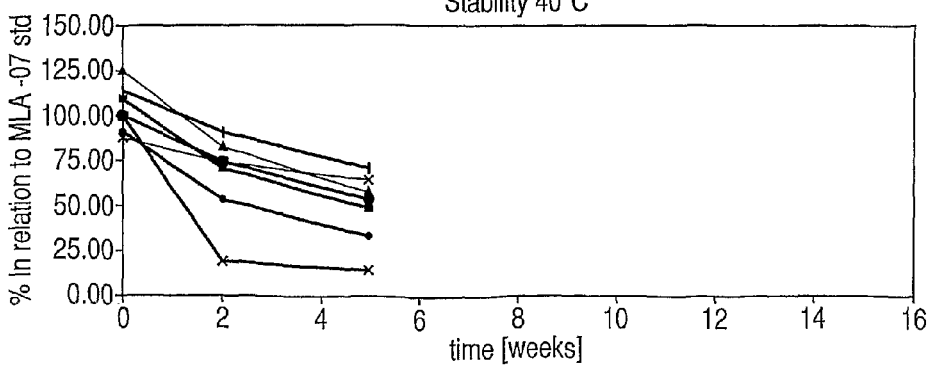
Fig.63. M245, S10, TG46, Met5 Stability 40°C

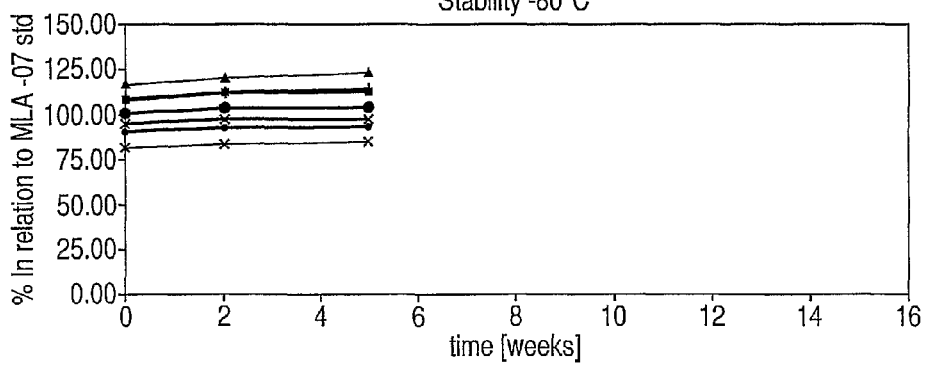
Fig.64. M235, S20, TG46, Met5 Stability -80°C
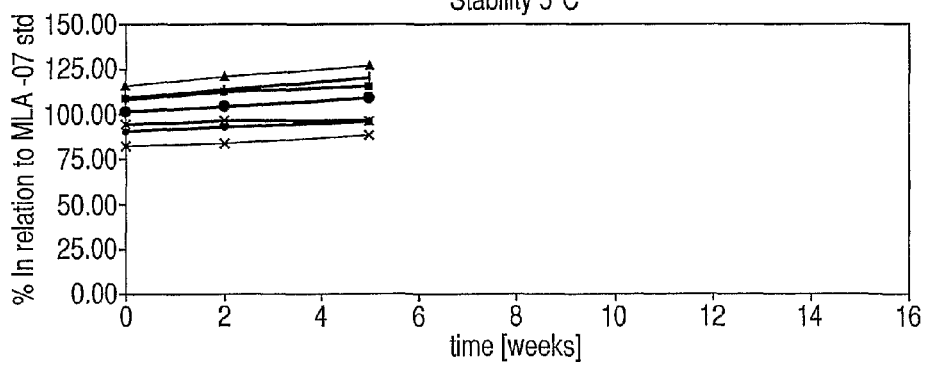
Fig.65. M235, S20, TG46, Met5 Stability 5°C
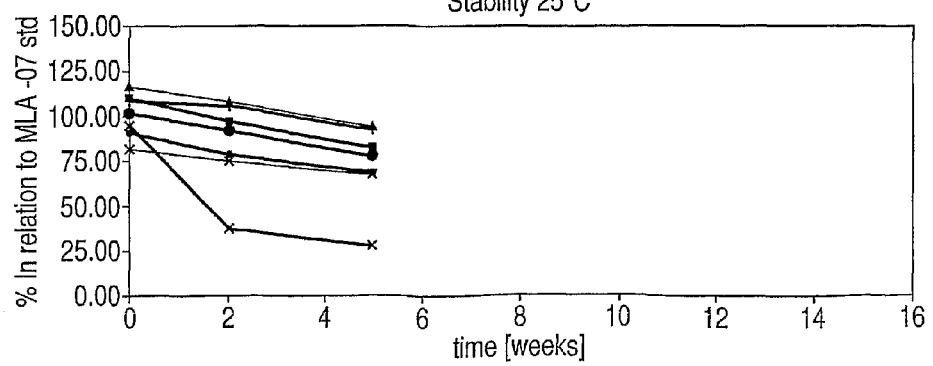
Fig.66. M235, S20, TG46, Met5 Stability 25°C

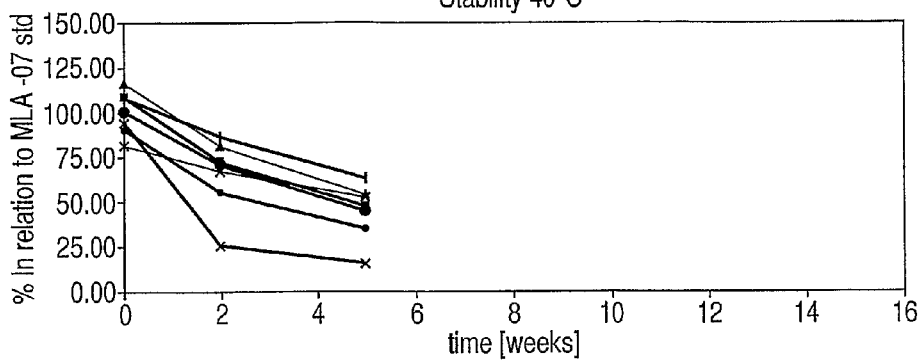
Fig.67. M235, S20, TG46, Met5 Stability 40°C
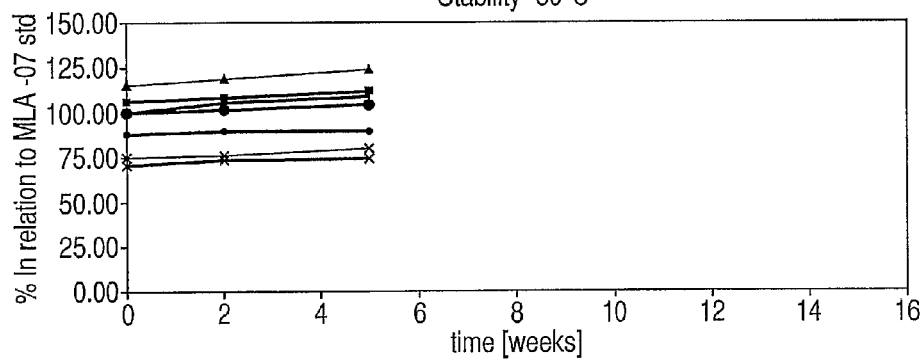
Fig.68. M225, S30, TG46, Met5 Stability -80°C
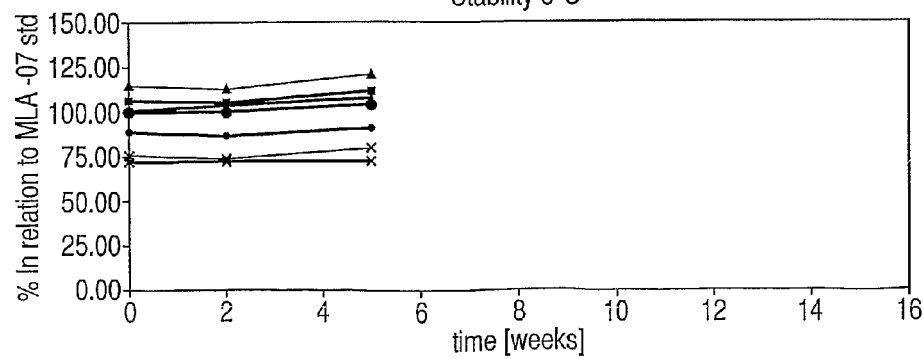
Fig.69. M225, S30, TG46, Met5 Stability 5°C

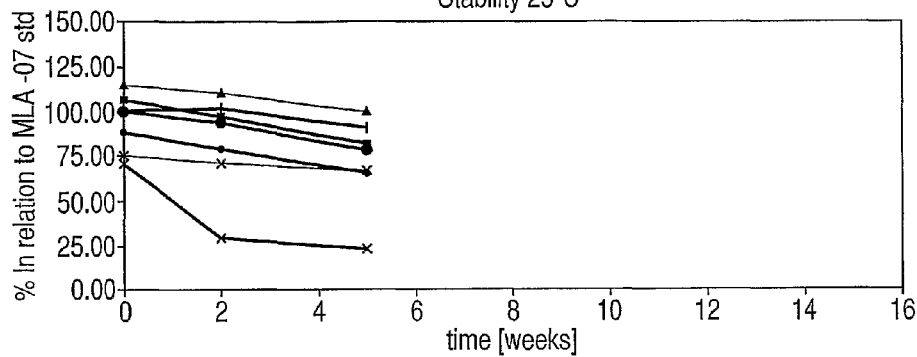
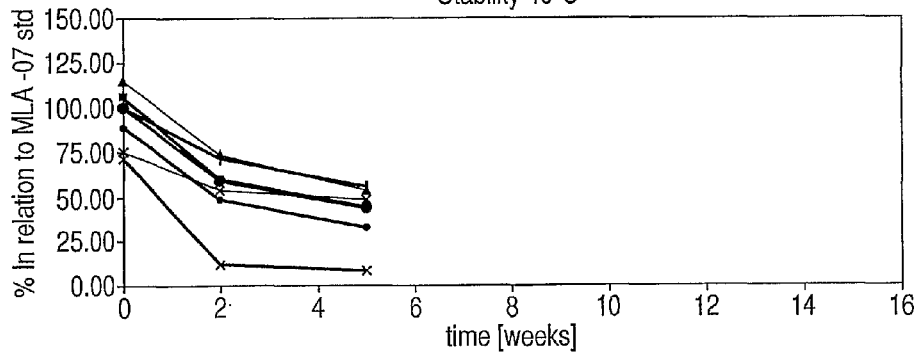
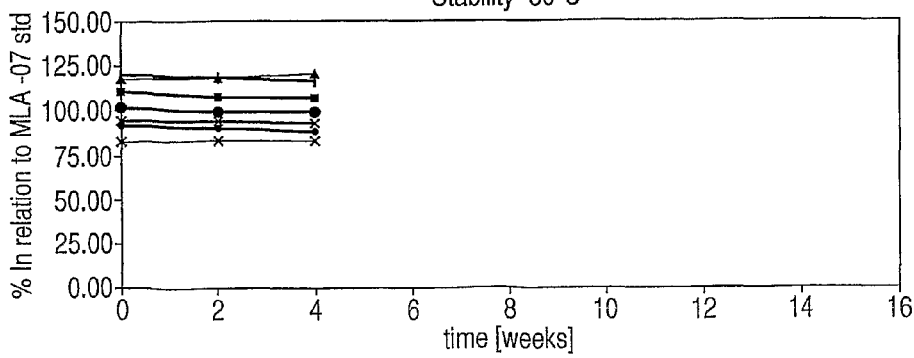

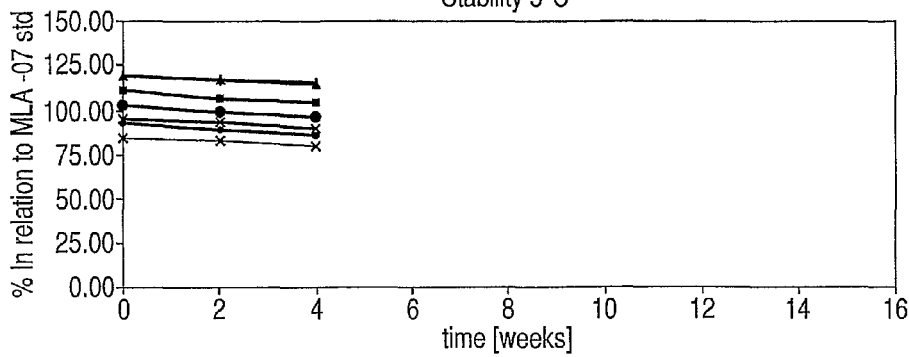
Fig. 73. M245, S10, TG46, Met5, EDTA 0,5 Stability 5°C
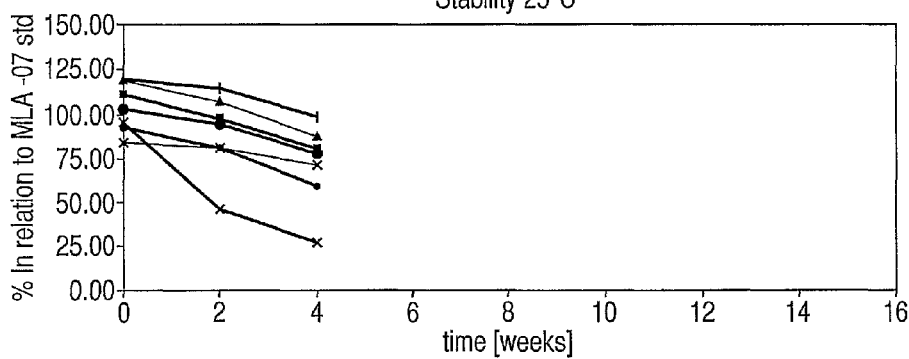
Fig. 74. M245, S10, TG46, Met5, EDTA 0,5 Stability 25°C
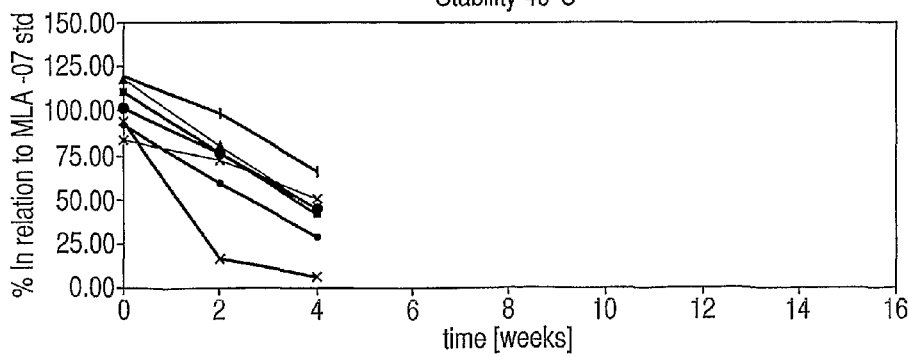
Fig. 75. M245, S10, TG46, Met5, EDTA 0,5 Stability 40°C

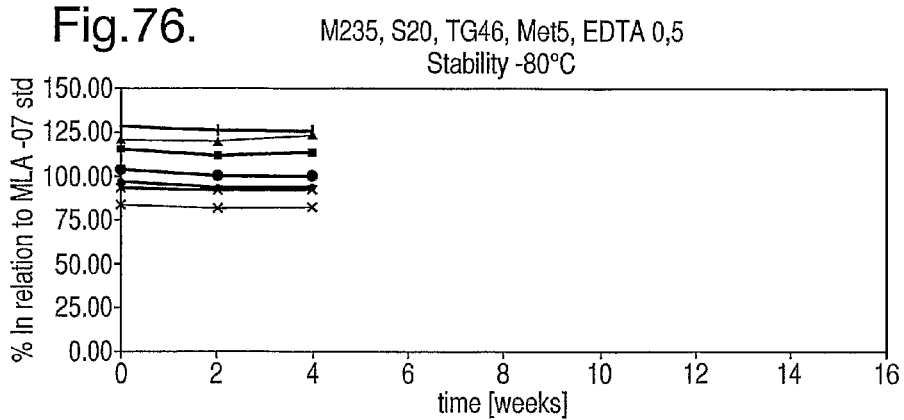
Fig.76. M235, S20, TG46, Met5, EDTA 0,5 Stability -80°C
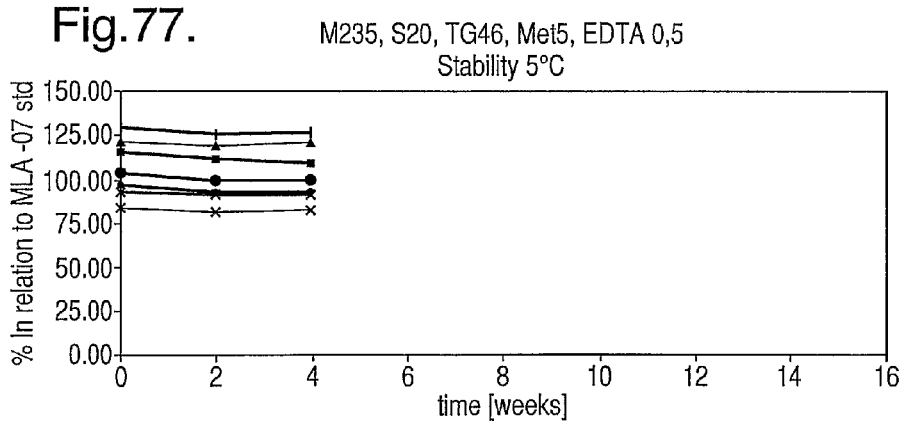
Fig.77. M235, S20, TG46, Met5, EDTA 0,5 Stability 5°C
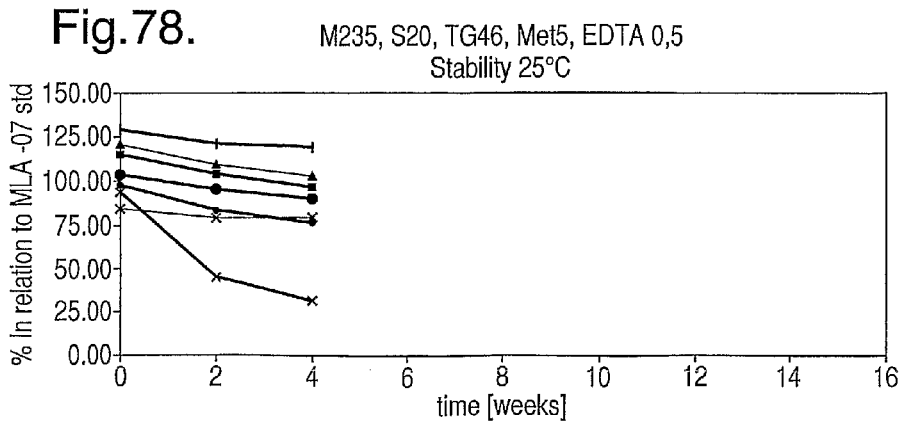
Fig.78. M235, S20, TG46, Met5, EDTA 0,5 Stability 25°C

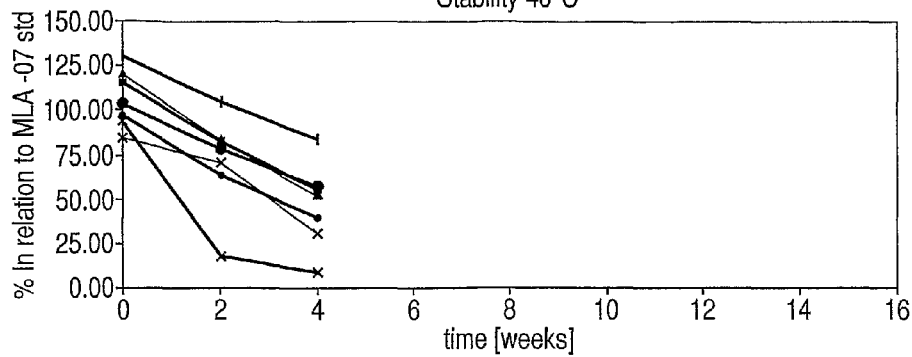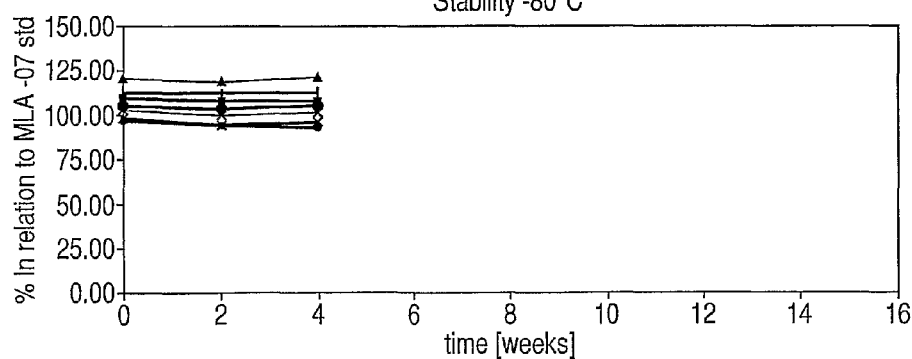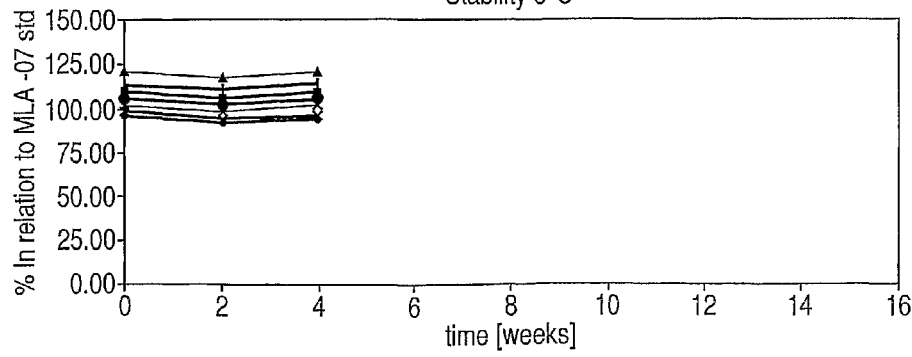

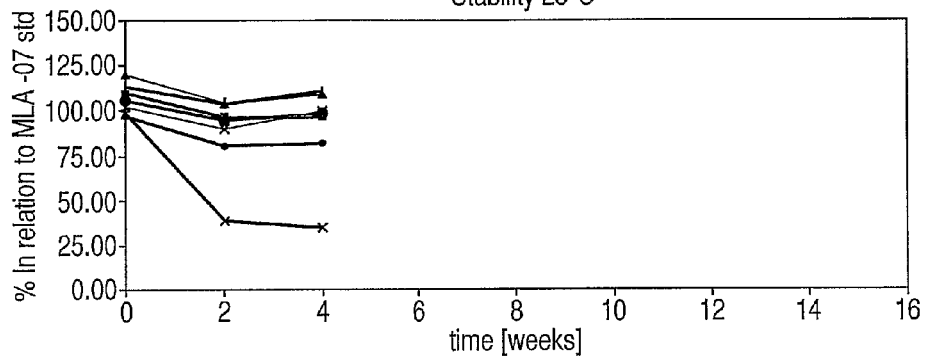
Fig.82. M225, S30, TG46, Met5, EDTA 0,5 Stability 25°C
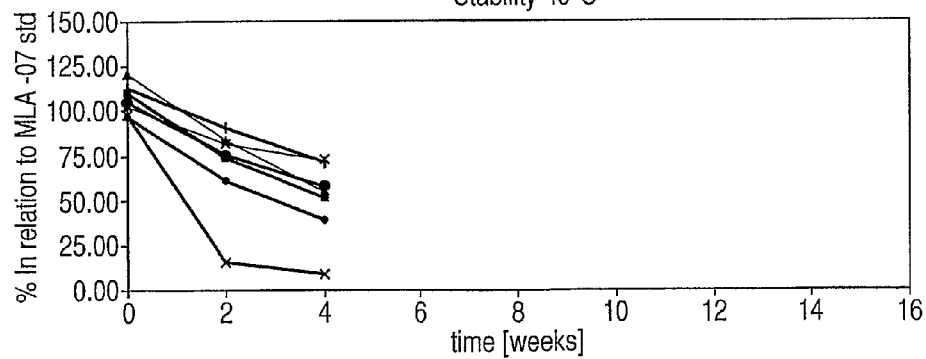
Fig.83. M225, S30, TG46, Met5, EDTA 0,5 Stability 40°C

SEQUENCE LISTING

<160> NUMBER OF SEQ ID NOS: 86

<210> SEQ ID NO 1
<211> LENGTH: 13
<212> TYPE: PRT
<213> ORGANISM: Felis catus

<400> SEQUENCE: 1

Cys Pro Ala Val Lys Arg Asp Val Asp Leu Phe Leu Thr
1               5                   10

<210> SEQ ID NO 2
<211> LENGTH: 17
<212> TYPE: PRT
<213> ORGANISM: Felis catus

<400> SEQUENCE: 2

```
Lys Ala Leu Pro Val Val Leu Glu Asn Ala Arg Ile Leu Lys Asn Cys
1               5                   10                  15
Val

<210> SEQ ID NO 3
<211> LENGTH: 17
<212> TYPE: PRT
<213> ORGANISM: Felis catus

<400> SEQUENCE: 3

Arg Ile Leu Lys Asn Cys Val Asp Ala Lys Met Thr Glu Glu Asp Lys
1               5                   10                  15
Glu

<210> SEQ ID NO 4
<211> LENGTH: 16
<212> TYPE: PRT
<213> ORGANISM: Felis catus

<400> SEQUENCE: 4

Thr Ala Met Lys Lys Ile Gln Asp Cys Tyr Val Glu Asn Gly Leu Ile
1               5                   10                  15

<210> SEQ ID NO 5
<211> LENGTH: 16
<212> TYPE: PRT
<213> ORGANISM: Felis catus

<400> SEQUENCE: 5

Ile Ser Ser Ser Lys Asp Cys Met Gly Glu Ala Val Gln Asn Thr Val
1               5                   10                  15

<210> SEQ ID NO 6
<211> LENGTH: 13
<212> TYPE: PRT
<213> ORGANISM: Dermatophagoides pteronyssinus

<400> SEQUENCE: 6

Arg Thr Val Thr Pro Ile Arg Met Gln Gly Gly Cys Gly
1               5                   10

<210> SEQ ID NO 7
<211> LENGTH: 19
<212> TYPE: PRT
<213> ORGANISM: Dermatophagoides pteronyssinus

<400> SEQUENCE: 7

Arg Asn Gln Ser Leu Asp Leu Ala Glu Gln Glu Leu Val Asp Cys Ala
1               5                   10                  15
Ser Gln His

<210> SEQ ID NO 8
<211> LENGTH: 13
<212> TYPE: PRT
<213> ORGANISM: Dermatophagoides pteronyssinus

<400> SEQUENCE: 8

Arg Tyr Val Ala Arg Glu Gln Ser Cys Arg Arg Pro Asn
1               5                   10

<210> SEQ ID NO 9
<211> LENGTH: 15
<212> TYPE: PRT
```

```
<213> ORGANISM: Dermatophagoides pteronyssinus

<400> SEQUENCE: 9

Asp Gln Val Asp Val Lys Asp Cys Ala Asn His Glu Ile Lys Lys
1               5                   10                  15

<210> SEQ ID NO 10
<211> LENGTH: 14
<212> TYPE: PRT
<213> ORGANISM: Dermatophagoides pteronyssinus

<400> SEQUENCE: 10

Gly Val Leu Ala Cys Ala Ile Ala Thr His Ala Lys Ile Arg
1               5                   10

<210> SEQ ID NO 11
<211> LENGTH: 13
<212> TYPE: PRT
<213> ORGANISM: Dermatophagoides pteronyssinus

<400> SEQUENCE: 11

Cys Ile Ile His Arg Gly Lys Pro Phe Gln Leu Glu Ala
1               5                   10

<210> SEQ ID NO 12
<211> LENGTH: 17
<212> TYPE: PRT
<213> ORGANISM: Dermatophagoides pteronyssinus

<400> SEQUENCE: 12

Arg Phe Gly Ile Ser Asn Tyr Cys Gln Ile Tyr Pro Pro Asn Val Asn
1               5                   10                  15

Lys

<210> SEQ ID NO 13
<211> LENGTH: 16
<212> TYPE: PRT
<213> ORGANISM: Dermatophagoides pteronyssinus

<400> SEQUENCE: 13

Asn Tyr Cys Gln Ile Tyr Pro Pro Asn Val Asn Lys Ile Arg Glu Ala
1               5                   10                  15

<210> SEQ ID NO 14
<211> LENGTH: 13
<212> TYPE: PRT
<213> ORGANISM: Dermatophagoides pteronyssinus

<400> SEQUENCE: 14

Asn Ala Gln Arg Phe Gly Ile Ser Asn Tyr Cys Gln Ile
1               5                   10

<210> SEQ ID NO 15
<211> LENGTH: 19
<212> TYPE: PRT
<213> ORGANISM: Dermatophagoides pteronyssinus

<400> SEQUENCE: 15

Asp Leu Arg Gln Met Arg Thr Val Thr Pro Ile Arg Met Gln Gly Gly
1               5                   10                  15

Cys Gly Ser

<210> SEQ ID NO 16
```

```
<211> LENGTH: 22
<212> TYPE: PRT
<213> ORGANISM: Dermatophagoides pteronyssinus

<400> SEQUENCE: 16

Gln Glu Ser Tyr Tyr Arg Tyr Val Ala Arg Glu Gln Ser Cys Arg Arg
1               5                   10                  15

Pro Asn Ala Gln Arg Phe
            20

<210> SEQ ID NO 17
<211> LENGTH: 22
<212> TYPE: PRT
<213> ORGANISM: Dermatophagoides pteronyssinus

<400> SEQUENCE: 17

Glu Pro Cys Ile Ile His Arg Gly Lys Pro Phe Gln Leu Glu Ala Val
1               5                   10                  15

Phe Glu Ala Asn Gln Asn
            20

<210> SEQ ID NO 18
<211> LENGTH: 15
<212> TYPE: PRT
<213> ORGANISM: Ambrosia artemisiifolia

<400> SEQUENCE: 18

Gly Ser Ser Gln Ile Trp Ile Asp His Cys Ser Leu Ser Lys Ser
1               5                   10                  15

<210> SEQ ID NO 19
<211> LENGTH: 15
<212> TYPE: PRT
<213> ORGANISM: Ambrosia artemisiifolia

<400> SEQUENCE: 19

Gly Gly Ser Gln Ile Trp Ile Asp His Cys Ser Leu Ser Lys Ala
1               5                   10                  15

<210> SEQ ID NO 20
<211> LENGTH: 12
<212> TYPE: PRT
<213> ORGANISM: Ambrosia artemisiifolia

<400> SEQUENCE: 20

Gly Ser Ser His Val Thr Val Ser Asn Cys Lys Phe
1               5                   10

<210> SEQ ID NO 21
<211> LENGTH: 12
<212> TYPE: PRT
<213> ORGANISM: Ambrosia artemisiifolia

<400> SEQUENCE: 21

Gly Ser Thr His Val Thr Ile Ser Asn Cys Lys Phe
1               5                   10

<210> SEQ ID NO 22
<211> LENGTH: 12
<212> TYPE: PRT
<213> ORGANISM: Ambrosia artemisiifolia

<400> SEQUENCE: 22

Gly Ser Thr His Phe Thr Val Ser Asn Cys Leu Phe
```

-continued

```
1               5                   10
```

<210> SEQ ID NO 23
<211> LENGTH: 15
<212> TYPE: PRT
<213> ORGANISM: Homo sapiens

<400> SEQUENCE: 23

```
His Ala Val Ser Asp His Glu Ala Thr Leu Arg Cys Trp Ala Leu
1               5                   10                  15
```

<210> SEQ ID NO 24
<211> LENGTH: 15
<212> TYPE: PRT
<213> ORGANISM: Homo sapiens

<400> SEQUENCE: 24

```
His Pro Ile Ser Asp His Glu Ala Thr Leu Arg Cys Trp Ala Leu
1               5                   10                  15
```

<210> SEQ ID NO 25
<211> LENGTH: 15
<212> TYPE: PRT
<213> ORGANISM: Homo sapiens

<400> SEQUENCE: 25

```
His Pro Val Ser Asp His Glu Ala Thr Leu Arg Cys Trp Ala Leu
1               5                   10                  15
```

<210> SEQ ID NO 26
<211> LENGTH: 15
<212> TYPE: PRT
<213> ORGANISM: Homo sapiens

<400> SEQUENCE: 26

```
Arg Cys Trp Ala Leu Ser Phe Tyr Pro Ala Glu Ile Thr Leu Thr
1               5                   10                  15
```

<210> SEQ ID NO 27
<211> LENGTH: 15
<212> TYPE: PRT
<213> ORGANISM: Homo sapiens

<400> SEQUENCE: 27

```
Arg Cys Trp Ala Leu Gly Phe Tyr Pro Ala Glu Ile Thr Leu Thr
1               5                   10                  15
```

<210> SEQ ID NO 28
<211> LENGTH: 29
<212> TYPE: PRT
<213> ORGANISM: Homo sapiens

<400> SEQUENCE: 28

```
Val Ser Pro Met Cys Ala Trp Cys Ser Asp Glu Ala Leu Pro Leu Gly
1               5                   10                  15

Ser Pro Arg Cys Asp Leu Lys Glu Asn Leu Leu Lys Asp
                20                  25
```

<210> SEQ ID NO 29
<211> LENGTH: 15
<212> TYPE: PRT
<213> ORGANISM: Homo sapiens

<400> SEQUENCE: 29

```
Val Ser Pro Met Cys Ala Trp Cys Ser Asp Glu Ala Leu Pro Leu
1               5                   10                  15
```

<210> SEQ ID NO 30
<211> LENGTH: 10
<212> TYPE: PRT
<213> ORGANISM: Homo sapiens

<400> SEQUENCE: 30

```
Ala Trp Cys Ser Asp Glu Ala Leu Pro Leu
1               5                   10
```

<210> SEQ ID NO 31
<211> LENGTH: 14
<212> TYPE: PRT
<213> ORGANISM: Homo sapiens

<400> SEQUENCE: 31

```
Ala Trp Cys Ser Asp Glu Ala Leu Pro Leu Gly Ser Pro Arg
1               5                   10
```

<210> SEQ ID NO 32
<211> LENGTH: 18
<212> TYPE: PRT
<213> ORGANISM: Homo sapiens

<400> SEQUENCE: 32

```
Ala Trp Cys Ser Asp Glu Ala Leu Pro Leu Gly Ser Pro Arg Cys Asp
1               5                   10                  15

Leu Lys
```

<210> SEQ ID NO 33
<211> LENGTH: 18
<212> TYPE: PRT
<213> ORGANISM: Homo sapiens

<400> SEQUENCE: 33

```
Ala Trp Ser Ser Asp Glu Ala Leu Pro Leu Gly Ser Pro Arg Cys Asp
1               5                   10                  15

Leu Lys
```

<210> SEQ ID NO 34
<211> LENGTH: 18
<212> TYPE: PRT
<213> ORGANISM: Homo sapiens

<400> SEQUENCE: 34

```
Ala Trp Gly Ser Asp Glu Ala Leu Pro Leu Gly Ser Pro Arg Cys Asp
1               5                   10                  15

Leu Lys
```

<210> SEQ ID NO 35
<211> LENGTH: 18
<212> TYPE: PRT
<213> ORGANISM: Homo sapiens

<400> SEQUENCE: 35

```
Ala Trp Cys Ser Asp Glu Ala Leu Pro Leu Gly Ser Pro Arg Ser Asp
1               5                   10                  15

Leu Lys
```

<210> SEQ ID NO 36

```
<211> LENGTH: 18
<212> TYPE: PRT
<213> ORGANISM: Homo sapiens

<400> SEQUENCE: 36

Ala Trp Cys Ser Asp Glu Ala Leu Pro Leu Gly Ser Pro Arg Gly Asp
1               5                   10                  15

Leu Lys

<210> SEQ ID NO 37
<211> LENGTH: 15
<212> TYPE: PRT
<213> ORGANISM: Homo sapiens

<400> SEQUENCE: 37

Thr Thr Arg Gly Val Ser Ser Cys Gln Gln Cys Leu Ala Val Ser
1               5                   10                  15

<210> SEQ ID NO 38
<211> LENGTH: 15
<212> TYPE: PRT
<213> ORGANISM: Homo sapiens

<400> SEQUENCE: 38

Asp Leu Pro Glu Glu Leu Ser Leu Ser Phe Asn Ala Thr Cys Leu
1               5                   10                  15

<210> SEQ ID NO 39
<211> LENGTH: 15
<212> TYPE: PRT
<213> ORGANISM: Homo sapiens

<400> SEQUENCE: 39

Phe Lys Asp Ser Leu Ile Val Gln Val Thr Phe Asp Cys Asp Cys
1               5                   10                  15

<210> SEQ ID NO 40
<211> LENGTH: 15
<212> TYPE: PRT
<213> ORGANISM: Homo sapiens

<400> SEQUENCE: 40

Pro Gly Ser Tyr Glu Asp Thr Cys Glu Lys Cys Pro Thr Cys Pro
1               5                   10                  15

<210> SEQ ID NO 41
<211> LENGTH: 15
<212> TYPE: PRT
<213> ORGANISM: Homo sapiens

<400> SEQUENCE: 41

Asp Asp Cys Val Val Arg Phe Gln Tyr Tyr Glu Asp Ser Ser Gly
1               5                   10                  15

<210> SEQ ID NO 42
<211> LENGTH: 15
<212> TYPE: PRT
<213> ORGANISM: Homo sapiens

<400> SEQUENCE: 42

Ala Tyr Phe Gly Leu Ser Val Ala Trp Cys Leu Pro Lys Pro Leu
1               5                   10                  15

<210> SEQ ID NO 43
```

```
<211> LENGTH: 24
<212> TYPE: PRT
<213> ORGANISM: Homo sapiens

<400> SEQUENCE: 43

Leu Cys Leu Leu Arg Phe Cys Phe Ser Ala Thr Arg Arg Tyr Tyr Leu
1               5                   10                  15

Gly Ala Val Glu Leu Ser Trp Asp
            20

<210> SEQ ID NO 44
<211> LENGTH: 16
<212> TYPE: PRT
<213> ORGANISM: Homo sapiens

<400> SEQUENCE: 44

Val Asn Gly Tyr Val Asn Arg Ser Leu Pro Gly Leu Ile Gly Cys His
1               5                   10                  15

<210> SEQ ID NO 45
<211> LENGTH: 23
<212> TYPE: PRT
<213> ORGANISM: Homo sapiens

<400> SEQUENCE: 45

Ile Ser Pro Ile Thr Phe Leu Thr Ala Gln Thr Leu Leu Met Asp Leu
1               5                   10                  15

Gly Gln Phe Leu Leu Phe Cys
            20

<210> SEQ ID NO 46
<211> LENGTH: 18
<212> TYPE: PRT
<213> ORGANISM: Homo sapiens

<400> SEQUENCE: 46

His Asp Gly Met Glu Ala Tyr Val Lys Val Asp Ser Cys Pro Glu Glu
1               5                   10                  15

Pro Gln

<210> SEQ ID NO 47
<211> LENGTH: 25
<212> TYPE: PRT
<213> ORGANISM: Homo sapiens

<400> SEQUENCE: 47

Pro Arg Cys Leu Thr Arg Tyr Tyr Ser Ser Phe Val Asn Met Glu Arg
1               5                   10                  15

Asp Leu Ala Ser Gly Leu Ile Gly Pro
            20                  25

<210> SEQ ID NO 48
<211> LENGTH: 21
<212> TYPE: PRT
<213> ORGANISM: Homo sapiens

<400> SEQUENCE: 48

Lys Thr Ala Phe Lys Lys Lys Asp Thr Ile Leu Ser Leu Asn Ala Cys
1               5                   10                  15

Glu Ser Asn His Ala
            20
```

```
<210> SEQ ID NO 49
<211> LENGTH: 25
<212> TYPE: PRT
<213> ORGANISM: Homo sapiens

<400> SEQUENCE: 49

Ile Ala Arg Tyr Ile Arg Leu His Pro Thr His Tyr Ser Ile Arg Ser
1               5                   10                  15

Thr Leu Arg Met Glu Leu Met Gly Cys
            20                  25

<210> SEQ ID NO 50
<211> LENGTH: 21
<212> TYPE: PRT
<213> ORGANISM: Homo sapiens

<400> SEQUENCE: 50

Pro Gln Ser Trp Val His Gln Ile Ala Leu Arg Met Glu Val Leu Gly
1               5                   10                  15

Cys Glu Ala Gln Asp
            20

<210> SEQ ID NO 51
<211> LENGTH: 19
<212> TYPE: PRT
<213> ORGANISM: Dermatophagoides farinae

<400> SEQUENCE: 51

Arg Asn Thr Ser Leu Asp Leu Ser Glu Gln Glu Leu Val Asp Cys Ala
1               5                   10                  15

Ser Gln His

<210> SEQ ID NO 52
<211> LENGTH: 20
<212> TYPE: PRT
<213> ORGANISM: Dermatophagoides pteronyssinus

<400> SEQUENCE: 52

Arg Asn Gln Ser Leu Asp Leu Ala Glu Gln Glu Leu Val Asp Cys Ala
1               5                   10                  15

Ser Gln His Gly
            20

<210> SEQ ID NO 53
<211> LENGTH: 23
<212> TYPE: PRT
<213> ORGANISM: Dermatophagoides pteronyssinus

<400> SEQUENCE: 53

Ser Ala Tyr Leu Ala His Arg Asn Gln Ser Leu Asp Leu Ala Glu Gln
1               5                   10                  15

Glu Leu Val Asp Cys Ala Ser
            20

<210> SEQ ID NO 54
<211> LENGTH: 10
<212> TYPE: PRT
<213> ORGANISM: Dermatophagoides pteronyssinus

<400> SEQUENCE: 54

Glu Leu Val Asp Cys Ala Ser Gln His Gly
1               5                   10
```

```
<210> SEQ ID NO 55
<211> LENGTH: 13
<212> TYPE: PRT
<213> ORGANISM: Dermatophagoides farinae

<400> SEQUENCE: 55

Pro Tyr Val Ala Arg Glu Gln Arg Cys Arg Arg Pro Asn
1               5                   10

<210> SEQ ID NO 56
<211> LENGTH: 15
<212> TYPE: PRT
<213> ORGANISM: Dermatophagoides farinae

<400> SEQUENCE: 56

Asp Gln Val Asp Val Lys Asp Cys Ala Asn Asn Glu Ile Lys Lys
1               5                   10                  15

<210> SEQ ID NO 57
<211> LENGTH: 13
<212> TYPE: PRT
<213> ORGANISM: Dermatophagoides farinae

<400> SEQUENCE: 57

Cys Ile Ile His Arg Gly Lys Pro Phe Thr Leu Glu Ala
1               5                   10

<210> SEQ ID NO 58
<211> LENGTH: 15
<212> TYPE: PRT
<213> ORGANISM: Dermatophagoides farinae

<400> SEQUENCE: 58

Asn Gly Val Leu Ala Cys Ala Ile Ala Thr His Gly Lys Ile Arg
1               5                   10                  15

<210> SEQ ID NO 59
<211> LENGTH: 15
<212> TYPE: PRT
<213> ORGANISM: Homo sapiens

<400> SEQUENCE: 59

Pro Arg Cys Leu Thr Arg Tyr Tyr Ser Ser Phe Val Asn Met Glu
1               5                   10                  15

<210> SEQ ID NO 60
<211> LENGTH: 23
<212> TYPE: PRT
<213> ORGANISM: Phleum pratense

<400> SEQUENCE: 60

Gly Asp Glu Gln Lys Leu Arg Ser Ala Gly Glu Leu Glu Leu Gln Phe
1               5                   10                  15

Arg Arg Val Lys Cys Lys Tyr
                20

<210> SEQ ID NO 61
<211> LENGTH: 20
<212> TYPE: PRT
<213> ORGANISM: Phleum pratense

<400> SEQUENCE: 61

Gly Ala Tyr Asp Thr Tyr Lys Cys Ile Pro Ser Leu Glu Ala Ala Val
1               5                   10                  15
```

Lys Gln Ala Tyr
        20

<210> SEQ ID NO 62
<211> LENGTH: 23
<212> TYPE: PRT
<213> ORGANISM: Alternaria alternata

<400> SEQUENCE: 62

Ser Asp Asp Ile Thr Tyr Val Ala Thr Ala Thr Leu Pro Asn Tyr Cys
1               5                   10                  15

Arg Ala Gly Gly Asn Gly Pro
        20

<210> SEQ ID NO 63
<211> LENGTH: 24
<212> TYPE: PRT
<213> ORGANISM: Alternaria alternata

<400> SEQUENCE: 63

Arg Asn Gly Phe Lys Arg Cys Leu Gln Phe Thr Leu Tyr Arg Pro Arg
1               5                   10                  15

Asp Leu Leu Ser Leu Leu Asn Glu
        20

<210> SEQ ID NO 64
<211> LENGTH: 23
<212> TYPE: PRT
<213> ORGANISM: Alternaria alternata

<400> SEQUENCE: 64

Ala Ile Glu Leu Lys Ser Cys Asn Ala Leu Leu Leu Lys Val Asn Gln
1               5                   10                  15

Ile Gly Thr Ile Thr Glu Ala
        20

<210> SEQ ID NO 65
<211> LENGTH: 13
<212> TYPE: PRT
<213> ORGANISM: Alternaria alternata

<400> SEQUENCE: 65

Glu Phe Ile Lys Lys Ala Ile Glu Leu Lys Ser Cys Asn
1               5                   10

<210> SEQ ID NO 66
<211> LENGTH: 12
<212> TYPE: PRT
<213> ORGANISM: Alternaria alternata

<400> SEQUENCE: 66

Ile Glu Leu Lys Ser Cys Asn Ala Leu Leu Leu Lys
1               5                   10

<210> SEQ ID NO 67
<211> LENGTH: 23
<212> TYPE: PRT
<213> ORGANISM: Alternaria alternata

<400> SEQUENCE: 67

Cys Ala Glu Tyr Gly Ala Asp Leu Ala Ile Thr Tyr Asn Ser Arg Ala
1               5                   10                  15

Glu Gly Ala Glu Lys Asn Ala
            20

<210> SEQ ID NO 68
<211> LENGTH: 21
<212> TYPE: PRT
<213> ORGANISM: Alternaria alternata

<400> SEQUENCE: 68

Ala Thr Glu Leu Lys Gly Ala Tyr Val Tyr Phe Ala Ser Asp Ala Ser
1               5                   10                  15

Ser Tyr Cys Thr Gly
            20

<210> SEQ ID NO 69
<211> LENGTH: 22
<212> TYPE: PRT
<213> ORGANISM: Alternaria alternata

<400> SEQUENCE: 69

Ser Asp Asp Ile Thr Tyr Val Ala Thr Ala Thr Leu Pro Asn Tyr Cys
1               5                   10                  15

Arg Ala Gly Gly Asn Gly
            20

<210> SEQ ID NO 70
<211> LENGTH: 20
<212> TYPE: PRT
<213> ORGANISM: Alternaria alternata

<400> SEQUENCE: 70

Ala Ile His Trp Val Asn Phe Gly Ile Tyr Phe Asn His Gly Gln Ala
1               5                   10                  15

Cys Cys Ala Gly
            20

<210> SEQ ID NO 71
<211> LENGTH: 23
<212> TYPE: PRT
<213> ORGANISM: Alternaria alternata

<400> SEQUENCE: 71

Cys Ala Glu Met Gly Ala Ala Val Ala Ile Thr Tyr Ala Ser Arg Ala
1               5                   10                  15

Gln Gly Ala Glu Glu Asn Val
            20

<210> SEQ ID NO 72
<211> LENGTH: 9
<212> TYPE: PRT
<213> ORGANISM: Alternaria alternata

<400> SEQUENCE: 72

Tyr Asn Val Ala Lys Ala Gly Cys Ile
1               5

<210> SEQ ID NO 73
<211> LENGTH: 20
<212> TYPE: PRT
<213> ORGANISM: Alternaria alternata

<400> SEQUENCE: 73

Ala Ile Ser Trp Val Asn Phe Gly Ile Phe Phe Asn His Gly Gln Cys

```
1               5                   10                  15

Cys Cys Ala Gly
            20

<210> SEQ ID NO 74
<211> LENGTH: 17
<212> TYPE: PRT
<213> ORGANISM: Alternaria alternata

<400> SEQUENCE: 74

Pro Asp Thr Phe Asn Tyr Val Lys Lys Glu Pro Ile Gly Val Cys Arg
1               5                   10                  15

Ser

<210> SEQ ID NO 75
<211> LENGTH: 14
<212> TYPE: PRT
<213> ORGANISM: Alternaria alternata

<400> SEQUENCE: 75

Ser Tyr Asn Val Ala Lys Ala Gly Cys Ile His Leu Ala Lys
1               5                   10

<210> SEQ ID NO 76
<211> LENGTH: 15
<212> TYPE: PRT
<213> ORGANISM: Betula sp

<400> SEQUENCE: 76

Cys Asn Glu Ile Lys Ile Val Ala Thr Pro Asp Gly Gly Ser Ile
1               5                   10                  15

<210> SEQ ID NO 77
<211> LENGTH: 15
<212> TYPE: PRT
<213> ORGANISM: Betula sp

<400> SEQUENCE: 77

Cys Asn Glu Ile Lys Leu Val Ala Thr Pro Asp Gly Gly Ser Thr
1               5                   10                  15

<210> SEQ ID NO 78
<211> LENGTH: 15
<212> TYPE: PRT
<213> ORGANISM: Betula sp

<400> SEQUENCE: 78

Cys Asn Glu Ile Lys Ile Val Ala Thr Pro Asp Gly Gly Cys Val
1               5                   10                  15

<210> SEQ ID NO 79
<211> LENGTH: 14
<212> TYPE: PRT
<213> ORGANISM: Betula sp

<400> SEQUENCE: 79

Ser Asn Glu Ile Lys Ile Val Ala Thr Pro Asp Gly Gly Cys
1               5                   10

<210> SEQ ID NO 80
<211> LENGTH: 15
<212> TYPE: PRT
<213> ORGANISM: Betula sp
```

```
<400> SEQUENCE: 80

Ser Asn Glu Ile Lys Ile Val Thr Thr Pro Asp Gly Gly Cys Val
1               5                   10                  15

<210> SEQ ID NO 81
<211> LENGTH: 17
<212> TYPE: PRT
<213> ORGANISM: Betula sp

<400> SEQUENCE: 81

Cys Asn Glu Ile Lys Ile Val Ala Ala Pro Gly Gly Gly Ser Ile Leu
1               5                   10                  15

Lys

<210> SEQ ID NO 82
<211> LENGTH: 15
<212> TYPE: PRT
<213> ORGANISM: Betula sp

<400> SEQUENCE: 82

Ala Glu Asn Phe Arg Ala Leu Cys Thr Gly Glu Lys Gly Asn Gly
1               5                   10                  15

<210> SEQ ID NO 83
<211> LENGTH: 21
<212> TYPE: PRT
<213> ORGANISM: Ambrosia artemisiifolia

<400> SEQUENCE: 83

Asp Gly Cys Trp Arg Gly Lys Ala Asp Trp Ala Glu Asn Arg Lys Ala
1               5                   10                  15

Leu Ala Asp Cys Ala
            20

<210> SEQ ID NO 84
<211> LENGTH: 16
<212> TYPE: PRT
<213> ORGANISM: Felis catus

<400> SEQUENCE: 84

Glu Gln Val Ala Gln Tyr Lys Ala Leu Pro Val Val Leu Glu Asn Ala
1               5                   10                  15

<210> SEQ ID NO 85
<211> LENGTH: 16
<212> TYPE: PRT
<213> ORGANISM: Felis catus

<400> SEQUENCE: 85

Lys Glu Asn Ala Leu Ser Leu Leu Asp Lys Ile Tyr Thr Ser Pro Leu
1               5                   10                  15

<210> SEQ ID NO 86
<211> LENGTH: 16
<212> TYPE: PRT
<213> ORGANISM: Felis catus

<400> SEQUENCE: 86

Ser Arg Val Leu Asp Gly Leu Val Met Thr Thr Ile Ser Ser Ser Lys
1               5                   10                  15
```

COMPOSITIONS WITH REDUCED DIMER FORMATION

RELATED APPLICATIONS

This application is a 35 U.S.C. 371 national stage filing of International Application No. PCT/GB2009/002767 filed Nov. 27, 2009, which claims priority to GB Application No. 0821806.7 filed Nov. 28, 2008. The contents of the aforementioned applications are hereby incorporated by reference.

FIELD OF THE INVENTION

The present invention relates to the use of a non-reducing carbohydrate or carbohydrate derivative and at least one agent which inhibits dimer formation in a freeze-dried composition comprising at least one peptide that contains a free cysteine residue, to provide a freeze-dried composition with improved long-term storage stability.

BACKGROUND OF THE INVENTION

There are various methods known in the art that are used to preserve a perishable material or make the material more convenient for transport. For pharmaceutical, biotechnological or food materials, a typical method is freeze-drying (also known as lyophilization or cryodesiccation). This is a dehydration process, which works by freezing the material and then reducing the surrounding pressure and adding only enough heat to allow the frozen water in the material to sublime directly from the solid phase to gas. The resulting freeze-dried product can then be readily reconstituted in solution for future use.

The advantage of a freeze-dried product, is that it is generally more stable during storage and transport and has a longer shelf-life than the equivalent material in solution. However, there are some problems with freeze-drying, in that damage to the material to be preserved can occur during the freezing and drying processes. These problems are to some extent addressed by the addition of cryoprotectants and lyoprotectants to the material to be freeze-dried. However, what is less well recognised is that some perishable materials, especially peptides that contain at least one free cysteine residue, are subject to degradation and damage even after completion of the freeze-drying process. That is, although freeze-drying has a preservative effect, freeze-dried products comprising peptides that comprise at least one free cysteine residue often have a shorter than desired shelf-life. There is a clear need for means to improve the stability of freeze-dried compositions comprising such peptides.

SUMMARY OF THE INVENTION

The invention relates to the use of (i) at least one non-reducing carbohydrate and (ii) at least one agent which inhibits dimer formation, in a freeze-dried composition comprising at least one peptide comprising at least one free cysteine residue, wherein the use is for preventing or reducing dimerisation of said at least one peptide in said composition.

The invention further relates to a method of producing a stable freeze-dried composition comprising at least one peptide, said method comprising:
a) preparing a composition comprising in solution (i) at least one non-reducing carbohydrate, (ii) at least one agent which inhibits dimer formation and (iii) at least one peptide comprising at least one free cysteine residue; and
b) freeze-drying the composition resulting from step (a).

In one embodiment, the resulting freeze-dried composition is stable for at least 2 years when stored at a temperature 2-8° C. In a further embodiment, the method further comprises reconstituting the freeze-dried composition of step (b) in solution.

The invention further relates to a stable, freeze-dried composition comprising at least one peptide for immunisation or tolerisation, wherein the composition additionally comprises at least one non-reducing carbohydrate and at least one agent which inhibits dimer formation.

In one embodiment of the uses, methods and compositions above, the at least one non-reducing carbohydrate is selected from trehalose, sucrose, raffinose, stachyose or melezitose and the agent is thioglycerol.

In one embodiment of the uses, methods and compositions above, the at least one peptide is for use in immunisation or tolerisation, is of 8 to 30 amino acids in length and comprises:
a) at least one cysteine residue; and
b) a region comprising at least one T cell epitope

DESCRIPTION OF THE DRAWINGS

FIGS. 1 to 83 show the stability of peptides, stored under different conditions as indicated, when comprised within different freeze-dried compositions as described in the Examples (T=trehalose, S=sucrose, M=mannitol, TG=thioglycerol, G=Glycine, Met=methionine). Time (weeks) is shown on the X-axis. The amount of non-degraded peptide present in a solution reconstituted from a given composition is shown on the Y axis. The amount is shown as a percentage relative to the amount of a standard of peptide MLA07 which has not been freeze-dried.

Each figure shows seven different result sets, corresponding to each of the following different peptides: MLA05 (dark line, small circular points); MLA12 (dark line, square points), MLA03 (light grey line, triangular points); MLA14 (light grey line, x-shaped points); MLA01 (dark line, x-shaped points), MLA04 (dark line, large circular points); MLA07 (dark line; vertical line-shaped points). Data was generated following freeze-drying a mixture of the seven peptides in each composition.

Figure 84:
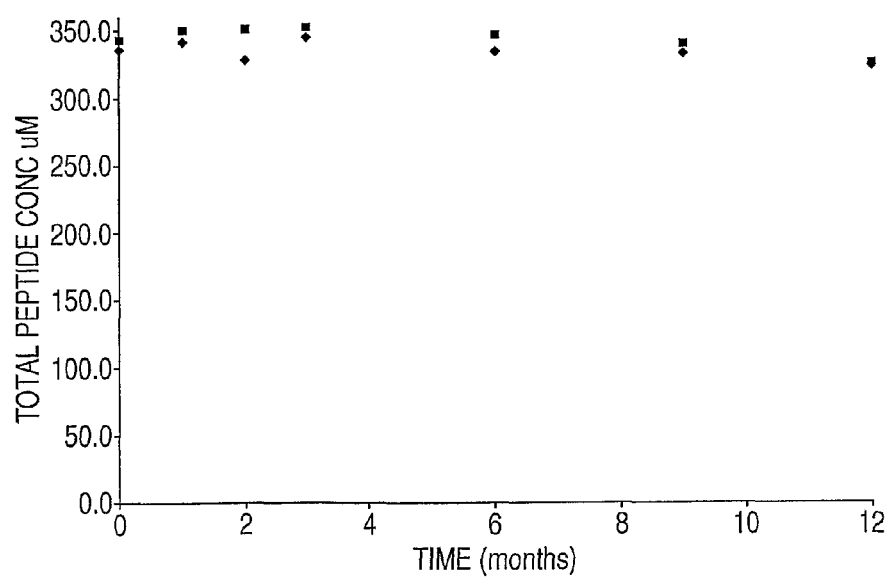

FIG. 84 shows the stability at 30° C./65% RH over 12 months of a mixture of the seven peptides: MLA05; MLA12, MLA03; MLA14; MLA01; MLA04 and MLA07, comprised in the specific compositions described in Example 4, that is Thioglycerol "low" (diamonds) and Thiglycerol "high" (squares).

DESCRIPTION OF THE SEQUENCES

SEQ ID NOS: 1 to 83 represent the sequences of peptides which are particularly preferred for inclusion in the compositions of the invention. SEQ ID NOS: 84 to 86 represent the sequences of additional peptides which may be included in the compositions of the invention.

DETAILED DESCRIPTION OF THE INVENTION

Freeze-Drying

Freeze drying is a complex operation where solvent (usually water) is removed from a product by sublimation. As is well known, sublimation occurs when a frozen liquid passes directly into the gaseous phase without passing through the liquid phase. Sublimation is a function of pressure and temperature, the balance of which is central to successful freeze-drying.

The freeze drying process consists of three stages: freezing, primary drying and secondary drying. During the freezing step, the solution is converted to a solid. The freezing procedure must be carefully controlled since the rate of freezing affects the size of the ice crystals formed in the product, which can affect product stability and may also affect the drying rate during the primary and secondary drying phases.

It is very important to perform the freezing step below a critical temperature. This temperature is the eutectic temperature (Teut) for crystalline materials or the glass transition temperature of the maximally freeze concentrated solute (Tg') for amorphous products.

During primary drying, the ice is removed from the frozen product via sublimation, resulting in a dry, structurally intact product. This requires careful control of shelf temperature and chamber pressure in the drying device. The rate of sublimation of ice from a frozen product depends on a variety of factors which will be appreciated by the person skilled in the art. It is important that during primary drying, the product temperature at the sublimation interface (Tp) must not exceed the "critical temperature" of the formulation, i.e. it must not attain sufficient fluidity to flow and thus destroy the structure of the cake. This is also known as the collapse temperature (Tc) and is typically several degrees higher than the Tg'.

As mentioned above, the critical temperature is Teut for mainly crystalline and Tg' or Tc for amorphous materials. Crystalline materials are easy to freeze dry since Teut is generally high (e.g. Teut of the very popular bulking agent mannitol is −3° C.). Furthermore, the resulting freeze-dried "cake" typically has an attractive appearance when derived from crystalline materials. However, crystalline materials are often not well suited to stabilising peptides during the freezing and drying processes. Here, amorphous sugars, polyols and other excipients are generally used. The drawback is that the Tg' of these substances generally much lower than eutectic temperatures (e.g. sucrose: −32° C.).

After primary drying is complete, and all ice has sublimed, bound moisture is still present in the product. The product appears dry, but the residual moisture content may be as high as 7-8%. Continued drying at higher shelf temperature is necessary to reduce the residual moisture content to optimum values (for many formulations<1%). This process, or secondary drying, is also known as isothermal desorption as the bound water is desorbed from the product. Secondary drying is normally continued at a product temperature higher than ambient but still below the glass transition (Tg) or melting temperature of the formulation.

It will be appreciated that the skilled person understands the need for careful consideration of the above parameters, with proper consideration given to differences in properties between different compositions and the potential need for trial and error to establish optimal freezing and drying conditions.

There are several advantages of the freeze drying process to stabilize delicate products (e.g. proteins, peptides, etc.): For example, properly freeze dried products often do not need refrigeration, they may be stored at ambient temperatures, and can rapidly be completely reconstituted with water or another suitable solvent for injection. A freeze-dried composition would typically be expected to have a stable shelf life of over 2 years. In this context, stable is typically taken to mean that the freeze-dried composition may be reconstituted without difficulty and that the reconstituted solution is suitable for pharmaceutical use. Stable is also considered to be the absence of any change in the physical or cosmetic appearance of the product, with the exception of break up of the freeze-dried cake, prior to reconstitution. Suitability for pharmaceutical use is dependent upon the biological material and specific use in question, but may typically be readily assessed by the skilled person. In general terms, the biological material in the reconstituted solution would be expected to have activity comparable to the equivalent material in solution before freeze-drying. In the case of a reconstituted solution comprising a peptide or protein, the reconstituted solution would typically be considered suitable for pharmaceutical use, particularly for injection, if it is sterile and free from visible particulates.

There are a number of difficulties with freeze-drying which may shorten the stable shelf-life of a product, sometimes dramatically, particularly for compositions comprising proteins or peptides having at least one free cysteine residue. Such materials may suffer irreversible change, or degradation, during the freeze-drying process, but also after this process, i.e. during storage of the freeze-dried product.

Degradation during the process of freeze-drying may occur during freezing, during drying, or during both freezing and drying. If product degradation occurs during freezing, addition of a "cryoprotectant" is typical. Cryoprotectants stabilize during freezing, but do not necessarily stabilize during lyophilization (i.e., during both freezing and drying). Common cryoprotectants include high concentrations of disaccharides and some amino acids (up to 0.5M), and low levels of polyethylene glycol (<1%, w/w) or other polymers. The term, "lyoprotection", refers to stabilization during all of the freeze-drying process (i.e., during both freezing and drying). Such stabilisation is often required for freeze-drying of biological materials such as proteins and peptides. This is because complex biological molecules such as proteins often require a moderate level of residual water to maintain structure and function Accordingly a "lyoprotectant" may typically be added. Lyoprotectants known in the art are typically polyhydroxy compounds such as sugars (mono-, di-, and polysaccharides), polyalcohols, and their derivatives.

By contrast to the above, damage and degradation which occur after the freeze-drying process, i.e. during storage or transport of the freeze-dried product, is more difficult to address. Such damage may take the form of for example, deamidation, hydrolysation, racemisation, or oxidation, all of which may typically result in aggregation and/or denaturation of a stored protein or peptide. Oxidation of the side-chains of cysteine residues, leading to the formation of disulphide bonds between molecules and their subsequent dimerisation is a particular problem. Such damage may occur slowly over a long period of time, or may occur rapidly during a short-term change in storage conditions, such as a sudden increase in temperature due to failure of a climate control system or even simple seasonal variation in the ambient temperature.

The present invention addresses the problems of damage and degradation which occur after the freeze-drying process, in freeze-dried compositions comprising at least one peptide, specifically a peptide comprising at least one free cysteine residue, by inhibiting or reducing dimerisation of said at least one peptide.

Freeze-Dried Compositions of the Invention

The present invention is particularly concerned with freeze-dried compositions comprising at least one peptide comprising at least one free cysteine residue. Peptides which are particularly of interest are those which are useful for modulating the immune system, specifically by modulating T-cell responses.

T-cell recognition of antigens requires antigen presenting cells (APCs) to present fragments (peptides) of the antigen protein on their cell surface in association with molecules of the major histocompatibility complex (MHC). T cells use their antigen specific T-cell receptors (TCRs) to recognise with high specificity the fragments presented by the APC. Such recognition acts as a trigger to the immune system to generate a range of responses to eradicate the antigen which has been recognized.

Most of the specificity of T cell recognition of the antigen fragments is provided by a smaller subsequence of amino acids within the fragments. This subsequence is known as the T cell epitope. Thus, peptides comprising such epitopes are of interest for use as therapeutic agents to modulate the immune systems of subjects. In the case of extracellular allergens and auto- or allo-antigens, the peptides are typically presented on MHC Class II molecules, which are recognized by CD4 T cells. Accordingly, interest in allergic and auto- or allo-immune disorders has focused on MHC Class II-binding T cell epitopes. However, MHC Class I-binding T cell epitopes, which are recognised by CD8 T cells, may also be of interest. For example, where it is required to modulate immune responses to endogenous and/or intracellular antigens. This may be desirable in the case of certain cancer markers, peptides from which may be used to induce tumour immunity, or for the treatment of infectious diseases such as those caused by hepatitis and human papilloma viruses.

Administration to subjects of peptide epitopes derived from extracellular allergens and auto- or allo-antigens has been demonstrated to result in the induction of tolerance to the antigen from which the epitope derives. Therapeutic agents based on such an effect have great potential in the prevention and treatment of allergy, and auto- or allo-immune diseases where the down-regulation of a specific immune response is desirable.

Administration to subjects of peptide epitopes derived from, for example, certain proteins associated with cancer or infectious diseases, has been demonstrated to result in the induction of specific immunity to the antigen from which the epitope derives. Therapeutic agents based on such an effect have great potential in the prevention and treatment of diseases where the up-regulation of a specific immune response is desirable.

Further progress in the use of peptide epitopes to produce tolerance or immunity to a specific antigen is hindered by a number of problems. One such problem is that epitope sequences, particularly epitope sequences from allergens and auto- and allo-antigens, are often poorly soluble, and are therefore problematic both to manufacture, to store and to administer to subjects. In particular, peptides comprising epitope sequences that contain cysteine residues may be vulnerable to dimerisation or higher order aggregation, leading to an inappropriate immune response, typically inflammation resulting from IgE or IgG binding.

Accordingly, when peptides comprising such epitopes are comprised within a freeze-dried composition they are particularly vulnerable to the types of damage and degradation which occur during transport and storage, i.e. after the freeze-drying process, as outlined above. This in turn leads to a reconstituted solution which is unsuitable for its intended pharmaceutical use, since when tolerisation is required the provocation of an inappropriate immune responses such as inflammation is highly undesirable. Similarly, when induction of specific immunity is required, the formation of dimers or higher order aggregates will inhibit binding to the MHC class I molecules or subsequent binding to the appropriate T-cells thus preventing the stimulation of T-cell mediated immune responses.

MHC Class II-Binding T Cell Epitopes

As discussed above, interest in peptides for the treatment or prevention of allergic and auto- or allo-immune disorders has focused on MHC Class II-binding T cell epitopes. Such epitopes may also be of interest when the provocation of a specific immune response is required. The MHC Class II-binding T cell epitope comprised in the peptides of the invention is typically the minimal amino acid sequence that is capable of binding to Class II molecules and capable of stimulating CD4 T cells when presented to T cells in association with Class II on the cell surface. The epitope is typically one that binds to a human MHC class II molecule, such as any such molecule mentioned herein.

An MHC Class II molecule consists of two proteins, $\alpha$ and $\beta$, each of which is encoded by a different gene. In humans, there are three clusters of genes encoding different $\alpha$ and $\beta$ proteins. These are the Human Leukocyte Antigen (HLA) clusters, DR, DQ and DP. Each cluster comprises multiple different A genes encoding different variant of the $\alpha$ protein and multiple different B genes encoding different variants of the $\beta$ protein. The resulting MHC Class II heterodimers are therefore extremely diverse, and correspondingly so are the T cell epitopes that they bind.

The binding site of MHC Class II molecules is composed of two separate proteins which form a cleft. The cleft is open-ended, which in theory allows a peptide of any length to bind. However, only 9 amino acids can occupy the cleft itself. The identities of the up to 9 amino acids which occupy the cleft define whether or not a given peptide will bind to a given MHC Class II molecule and be available for presentation to T cells. These up to 9 amino acids therefore represent the minimal sequence that is required for MHC Class II-binding. It is generally assumed that such a sequence will be capable of stimulating T cells when presented to T cells in association with Class II on the cell surface. However, this may be confirmed experimentally by methods standard in the art.

Such methods may typically comprise contacting the epitope with T cells in a sample taken from a subject, under conditions which allow the epitope and the T cells to interact; and then determining whether or not any of the T cells are stimulated. Determining whether or not the T cells are stimulated may be achieved by any suitable method, for example by detecting the production of cytokines by the T cells, wherein cytokine production indicates that T cells have been stimulated. Suitable cytokines include interferon gamma, interleukin 4 and interleukin 13. Cytokine production may be detected by any suitable method, for example an ELISA, ELISPOT assay or a flow cytometric assay. The T cells in a sample from a subject are typically present in a population of peripheral blood mononuclear cells (PBMCs) isolated from a blood or serum sample taken from the subject.

The MHC Class II-binding T cell epitope of the invention typically consists of 8 or 9 amino acids, but may consist of 7, 8, 9, 10, 11, 12, 13, 14, 15, 16, 17, 18, 19 or 20 amino acids. The amino acid sequence of the epitope may be broadly defined by further reference to the binding site of MHC Class II molecules. This binding site has specific binding pockets, which corresponding to primary and secondary anchor positions in the sequence of the binding peptide epitope. The binding pockets are defined by amino acid positions in the sequence of the MHC Class II molecule, and are generally not absolutely discriminatory for a specific amino acid in the epitope. Therefore the peptide binding specificity of any given MHC molecule is relatively broad. Thus, peptides binding to the same MHC allotype exhibit some degree of similarity, but there is no requirement for identity.

For the most common human MHC Class II type, HLA-DR, the key anchor positions for binding to the binding pockets are at positions 1, 4, 6, 7 and 9 of the peptide epitope (counting from the most N terminal residue occupying the cleft to the most C terminal). Different HLA-DR alleles which have similar amino acids in their binding pockets therefore typically bind peptides with similar amino acids at positions 1, 4, 6, 7 and 9. Accordingly, the region containing an MHC Class II binding T cell epitope preferably has amino acids at positions corresponding to positions 1, 4, 6, 7 and 9 that allow binding to the widest range of HLA-DR alleles. Examples of characteristic binding properties of different HLA-DR alleles are set out below:

DR alleles with Glycine at position 86 of the β chain show strong preferences for large hydrophobic side chains (Trp, Tyr, Phe) at peptide position 1, whereas Valine at position 86 restricts the pocket size and alters the preferences to small hydrophobic side chains (Val and Ala) at this position. Medium sized hydrophobic amino acids Leu and Ile are well accepted in all DR alleles.

DR alleles with Gln at position 70, Lysine at position 71, and Arginine or Gln at position 74 of the β chain have an overall positive charge within pocket 4, which requires negatively charged amino acids Asp and Glu at position 4 of the binding peptide (as in for example, DRB1*0301). DR alleles with this motif are associated with two autoimmune diseases: systematic lupus erythematosus and Hashimoto's thyroiditis.

DR alleles with Gln or Arg at position 70, Arg or Lys at position 71 and Glu or Ala at position 74 of the β chain bind similar peptides to those directly above since the only significant difference is at position 74. However, when Ala is present at position 74, pocket 4 increases in size and can accommodate larger amino acids such as Phe, Trp, and Ile (as in for example DRB1*0401, 04, 05). Alleles bearing Glu at position 74 are expected to allow small polar residues, like Ser and Thr at position 4 of the binding peptide. DR alleles with this motif are associated with a susceptibility to rheumatoid arthritis.

DR alleles with Asp at position 70, Glu or Arg at position 71, and Leu or Ala at position 74 of the β chain exclude peptides with negatively charged amino acids at peptide position 4 (for example DRB1*0402). This is due to the presence of Asp at position 70. DR alleles with this motif are associated with the autoimmune diseases Juvenile rheumatoid arthritis (JRA), pemphigus vulgaris, and allergic bronchopulmonary disease/syndrome.

Polymorphisms at position 9 of the β chain define the size of binding pocket 9 in all DR alleles. Alleles with Trp at this position accept only small amino acids in position 9 of the binding peptide, e.g. Ala, Val, Gly, Ser, Thr, Pro (as in for example DRB1*0101 and *1501). Glu at position 9, in combination with Asp at position 57, makes pocket 9 negatively charged, facilitating the accommodation of positively charged amino acids, such as Lys (as in for example DRB1*0401 and *0404) and Histidine (as in for example DRB1*0402). In most MHC class II alleles, Asp at position 57 makes a salt-bridged hydrogen bond with Arg at position 76, allowing the pocket to also accommodate aliphatic and polar amino acids. In cases where Asp at position 57 is replaced by Ser (for example DRB1*0405) or Ala (DQ8), the hydrogen bonding network is destroyed and Arg at position 76 can strongly attract negatively charged amino acids such as Asp or Glu at position 9 of the binding peptide (as in for example DRB1*0405).

An example of a preferred sequence for an epitope therefore has Trp, Tyr, Phe, Val or Ala at position 1; Asp, Glu, Ser or Thr at position 4; and Ala, Val, Gly, Ser, Thr, Pro at position 9. A further example of a preferred sequence for an epitope has a large aromatic or hydrophobic amino acid at position 1, for example Tyr, Phe, Trp, Leu, Ile or Val, and a small, non-charged amino acid at position 6, for example Ser, Thr, Ala, Pro, Val, Ile or Met. Approximately 87.5% of peptides binding to all or a combination of the MHC Class II molecules encoded by the DRB1*0101, *0401 and *0701 alleles contain this motif. Furthermore, since T cell epitopes derived from allergens and autoimmune antigens do not typically contain a large number of repeats of a given amino acid or amino acids, preferred epitopes of the invention typically comprise at least 5, 6, 7 or 8 different amino acids.

The precise amino sequence of an epitope may be predicted by computer-based algorithms and confirmed by in vitro biochemical analysis. Suitable commercially available algorithms include the EpiMatrix algorithm (EpiVax Inc.). Other algorithms are available at, for example http://www.imtech.res.in/raghava/propred/ and http://www.imtech.res.in/raghava/mhc2pred/. Analysis with these algorithms typically comprises parsing a larger polypeptide sequence into multiple overlapping small peptides. The sequences of these small peptides are then analysed using the algorithm to identify those which are predicted to bind MHC Class II molecules. The overlapping small peptides are typically 9-mers.

The candidate peptides which score most highly in this analysis are then assessed for the ability to bind a panel of MHC Class II molecules encoded by different Class II alleles in vitro using standard binding assays. For example a competitive MHC class II binding assay may be used, wherein each peptide is analysed for its ability to displace a known control binder from each of the human MHC class II allotypes investigated. In such an assay each peptide is assigned an IC50 value (the concentration at which 50% inhibition of control peptide binding is achieved). The lower the IC50 the higher the affinity of a peptide for a given MHC class II allotype.

The epitope or epitopes in a polypeptide are taken to be those peptides which show the highest binding affinity to MHC Class II molecules. Particularly preferred epitopes show high affinity binding to different Class II molecules encoded by more than one preferably two, more preferably three, four or five MHC Class II alleles.

Particularly preferred epitopes are those which are comprised in regions which are prone to dimer formation. These regions are defined in a separate section below.

MHC Class I-Binding T Cell Epitopes

As discussed above, MHC Class-1 binding epitopes are usually of more interest for the provocation of a specific immune response (such as tumour immunity or the induction of immune responses against infectious disease causing agents). The MHC Class I-binding T cell epitope comprised in the peptides of the invention is typically the minimal amino acid sequence that is capable of binding to Class I molecules and capable of stimulating CD8 T cells when presented to T cells in association with Class I on the cell surface. The epitope is typically one that binds to a human MHC class I molecule, such as any such molecule mentioned herein.

An MHC Class I molecule consists of a heavy peptide chain noncovalently linked to a smaller peptide called $\beta_2$-microglobulin. The heavy peptide chain is organized into three large globular domains, $\alpha 1$, $\alpha 2$ and $\alpha 3$, and a smaller transmembrane and intracellular region. The heavy peptide chain is encoded by a single gene. In humans, there are three major clusters of genes encoding different Class I heavy chains, and three minor clusters. These are the Human Leukocyte Antigen (HLA) clusters, HLA-A, HLA-B, HLA-C (major) and HLA-E, HLA-F and HLA-G (minor). Each cluster comprises multiple different genes encoding different variant of the heavy chain. The resulting MHC Class I proteins are therefore very diverse, and correspondingly so are the T cell epitopes that they bind.

The binding site of MHC Class I molecules is formed by the cleft between the α1 and α2, domains (those furthest from the cell membrane). The cleft is a closed pocket, and typically a peptide binding in the cleft has a maximum length of up to 12 amino acids. The identities of the up to 12 amino acids which occupy the cleft define whether or not a given peptide will bind to a given MHC Class I molecule and be available for presentation to T cells. These amino acids therefore represent the minimal sequence that is required for MHC Class I-binding. It is generally assumed that such a sequence will be capable of stimulating T cells when presented to T cells in association with Class I on the cell surface. However, this may be confirmed experimentally by methods standard in the art usually equivalent methods to those set out above for Class II epitopes.

The MHC Class I-binding T cell epitope of the invention typically consists of between 6 and 12, more usually between 8 and 12 amino or 8 and 10 amino acids. The epitopes may consist of 8, 9, 10, 11 or 12 amino acids. Most typically, the epitopes are 9 amino acids in length. The amino acid sequence of the epitope may be broadly defined by further reference to the binding site of MHC Class I molecules. The closed nature of the MHC Class I binding cleft means that the residues at each terminus of a Class I epitope are particularly important for recognition. The amino-terminal amine group of the peptide makes contact with an invariant site at one end of the peptide groove, and the carboxylate group at the carboxy terminus binds to an invariant site at the other end of the groove. However, these invariant are generally not absolutely discriminatory for a specific amino acid in the epitope. Therefore the peptide binding specificity of any given MHC molecule is relatively broad. Thus, peptides binding to the same MHC allotype exhibit some degree of similarity, but there is no requirement for identity. Even so, typically, Class I epitopes have a hydrophobic or basic carboxy terminus and an absence of proline in the extreme amino terminus. The epitope lies in an extended confirmation along the groove with further contacts between main-chain atoms and conserved amino acid side chains that line the groove. Variations in length are accommodated by a kinking in the peptide backbone, often at proline or glycine residues.

Particularly preferred epitopes are those which are comprised in regions which are prone to dimer formation. These regions are defined in a separate section below.

Regions Containing at Least One T Cell Epitope

Biochemical assays for the identification of a T cell epitope are not typically able to define the position of the minimal epitope sequence within a larger sequence more accurately than to within approximately 10 to 12 amino acids, and more typically 15, 20 or more amino acids. The reason for this is that a large sequence must be physically fragmented into smaller overlapping peptides, or smaller overlapping peptides must be manufactured de novo prior to in vitro assessment of the ability of these peptides to bind MHC molecules. The skilled person will recognise that the smaller the overlapping peptide fragments used, the more time-consuming and labour intensive is the process of manufacture. Hence epitopes are often identified as being contained within a larger polypeptide region. It is envisaged that the peptides of the invention may comprise such a larger region.

Accordingly, in the peptides of the invention, the region containing a T cell epitope is typically 8 or 9 amino acids in length, but may be 6, 7, 10, 11, 12, 13, 14, 15, 16, 17, 18, 19, 20, 21, 22, 23, 24 or 25 amino acids in length. In the case of MHC Class-I binding T cell epitopes, it will be understood that processing of the region may be required before the epitope can be presented on the MHC molecule. Antigen processing prior to presentation on MHC Class I molecules is a well-known occurrence in the art.

The region of the invention is typically a sequence which is prone to dimer formation. This will be understood to include both homodimer formation (i.e. association of peptide monomers with other identical peptide monomers) and heterodimer formation (i.e. association of peptide monomers with different peptide monomers). It will also be understood that by a sequence prone to dimer formation, it is also intended to refer to sequences which are prone to form higher order oligomers, such as trimers, tetramers and the like. The region of the invention may comprise or consist of any sequence which is prone to dimer formation. The particular amino acid sequence within a given region which promotes dimer formation may be comprised within the minimal MHC class II-binding sequence of the T cell epitope, or may be comprised within the residues which flank this sequence. The sequence prone to dimer formation may thus consist entirely of the minimal MHC binding sequence of the T cell epitope.

The present invention is particularly concerned with the formation of covalent dimers between cysteine containing peptides. Accordingly, preferred sequences comprise at least one cysteine residue. The skilled person will appreciate that any peptide that contains a single cysteine residue may form dimers, either with itself, or with other cysteine containing peptides with which it may be contacted. Peptides that contain two or more cysteines have the potential to form long chains which may then aggregate. Such dimer/aggregate formation leads to the risk of IgE or IgG binding and thus having a local inflammatory response. Accordingly, a preferred region of the invention typically derives from a protein with a high proportion of cysteine residues. For example, the region of the invention may derive from a protein having greater than 20, 21, 22, 23, 24, 25, 26, 27, 28, 29, 30, 31, 32, 33, 34 or 35% cysteine residues as a proportion of the total number of amino acid residues in the protein. The region of the invention is preferably selected from a sequence within such a protein that has a lower proportion of cysteine residues. Accordingly, the region may comprise up to a maximum of 5, 6, 7, 8, 9, 10, 11, 12, 13, 14, 15, 16, 17, 18, 19 or 20% cysteine residues as a proportion of the total number of amino acid residues in the region. The cysteine residues may be comprised in the minimal MHC binding sequence of the epitope, or may be comprised in the residues which flank this sequence.

Other sequences prone to dimer formation may be identified by in silico analysis using suitable computational methods, or by in vitro analysis using suitable laboratory methods which quantify the proportion of a sequence which is present in monomeric or dimeric form as set out below. For a sequence that is prone to dimerisation the proportion of sequence present as a dimer may be minimal, i.e. less than about 0.5% or 1% in the solid state, but this will typically increase over time to at least about 0.5%, 1%, 2%, 3%, 4%, 5%, 6%, 7%, 8%, 9%, 10%, 20%, 30%, 40%, 50%, 60%, 70%, 80% or 90% for material stored in solution for a suitable period of time under suitable conditions. Suitable periods of time and conditions include ranges of time and conditions under which a skilled practitioner might reasonably expect to keep a sequence in solution prior to use. For example, periods of time of about 24 hours, about 48 hours, or about 72 hours are typical, although some solutions may be kept for longer periods for example, at least a week, a month, 6 months, 1 year, 2 years, 3 years or more. Storage conditions may typically be room temperature and relative humidity, or typically 25° C. and 60% relative humidity, but could include any standard storage conditions encountered by the skilled person, for example approximately 5±3° C., −20° C., or −80° C.

The sensitivity of the immune system is such that only a small proportion of dimer is considered likely to trigger an undesirable immune response.

For the assessment of the proportion of a sequence present in a given form a suitable method is, for example, analytical gel electrophoresis under non-denaturing conditions. In such a method, a solution of the sequence is run in a polyacrylamide gel, alongside a set of standard molecular weight markers. If the sequence forms dimers, a protein band will be observed in the gel corresponding to a species with a molecular weight approximately twice that calculated for the sum of the amino acids of the sequence. (Similarly, any trimers or tetramers present will be observed as bands corresponding to species with molecular weights approximately three or four times that calculated for the sum of the residue weights of an amino acids of the sequence). Since it is rare that 100% of a sequence is present in oligomeric form, a second band may also be observed corresponding to a species with approximately the molecular weight calculated for the sum of the amino acids of the sequence—this represents the sequence in monomeric form. The relative intensities of the bands may be used to quantify the proportion of the sequence which is present in each form. Similar methods may assess molecular weight by alternative means, for example, analytical centrifugation, mass spectrometry or size exclusion chromatography. Alternatively, oligomers may be quantified using reverse phase high performance liquid chromatography (RP-HPLC) where the dimers and higher oligomeric species are separated from the monomers based on differences in their hydrophobicities. Identification of the species is achieved using mass spectrometric detection. The same methods may be adapted to assess whether a given peptide shows a tendency to heterodimerise with any other peptide or molecule.

Additionally, the region of the invention may have a solubility of less than 3.5 mg/ml in aqueous solution at pH 2.0 to 12.0, or pH 2.0 to 11.0, pH 2.0 to 10.0, pH 2.0 to 9.0, pH 2.0 to 8.0 or pH 2.0 to 7.0; and/or comprise 1, 2, 3 or 4 cysteine residues; and/or have an isoelectric point lower than 4.5; and/or have a GRAVY score above +0.25. These parameters may be assessed by any suitable method. For example, solubility may be assessed by standard in vitro methods, GRAVY and isoelectric point may be assessed in silico using suitable computational methods, such as the ProtParam tool (Gasteiger E. et al pp. 571-607 The Proteomics Protocols Handbook, Humana Press (2005); John M. Walker (ed)) which is available at http://www.expasy.ch/tools/protparam.html.

Peptides

The peptide of the invention may comprise or consist of the native sequence of the region as defined above or may comprise or consist of the native sequence of the region engineered to reduce dimer formation or improve solubility. However, in the context of a region which has been engineered, it will be understood that the present invention is particularly applicable to those peptides which may still undergo an unacceptable level of dimer formation. Such peptides will typically still comprise at least one cysteine residue.

Where a region is engineered to reduce dimer formation, this will typically be by modification of its native sequence. Particularly preferred modifications are wherein:
- at least one cysteine residue in the native sequence of the region is replaced with serine, 2-aminobutyric acid, alanine or glycine; and for
- at least one cysteine residue in the native sequence of the region is cysteinylated to create a cystine residue.

It will be understood that peptides of the invention is intended to encompass certain variants of said peptides. Other than the engineering to reduce dimer formation discussed above, other modifications to the native amino acid sequence of a peptide may be made. For example to one, two, three, four, or five amino acids in the sequence of a peptide. Any such modifications will typically be conservative, in that if an amino acid in the native sequence is replaced with a different amino acid, the different amino acid will typically have similar properties to the native amino acid. The table below shows the properties of amino acids. Molecular weights are shown alongside the 3-letter code for each amino acid. The molecular weights given are those of the neutral, free amino acids; residue weights can be obtained by subtraction of one equivalent of water (18 g/mol). The invention also includes peptides containing N- and C-terminals modified or blocked to reduce or inhibit degradation by exopeptidase enzymes.

| Ala | 89 | Aliphatic, hydrophobic, neutral | Met | 149 | hydrophobic, neutral |
| Cys | 121 | polar, hydrophobic, neutral | Asn | 132 | polar, hydrophilic, neutral |
| Asp | 133 | polar, hydrophilic, charged (−) | Pro | 115 | hydrophobic, neutral |
| Glu | 147 | polar, hydrophilic, charged (−) | Gln | 146 | polar, hydrophilic, neutral |
| Phe | 165 | Aromatic, hydrophobic, neutral | Arg | 174 | polar, hydrophilic, charged (+) |
| Gly | 75 | Aliphatic, neutral | Ser | 105 | polar, hydrophilic, neutral |
| His | 155 | aromatic, polar, hydrophilic, charged (+) | Thr | 119 | polar, hydrophilic, neutral |
| Ile | 131 | Aliphatic, hydrophobic, neutral | Val | 117 | aliphatic, hydrophobic, neutral |
| Lys | 146 | polar, hydrophilic, charged(+) | Trp | 204 | aromatic, hydrophobic, neutral |
| Leu | 131 | Aliphatic, hydrophobic, neutral | Tyr | 181 | aromatic, polar, hydrophobic |

The residue or residues which are modified may be comprised in any part of the sequence of the region. In one embodiment the residue or residues which are modified are not comprised in the minimal MHC binding sequence of the region. In a preferred embodiment, the modification does not create a new epitope or affect the MHC binding properties of the region.

The peptide of the invention typically contains from 8 to 30 amino acids, and may contain 9, 10, 11, 12, 13, 14, 15, 16, 17, 18, 19, 20, 21, 22, 23, 24, 25, 26, 27, 28 or 29 amino acids. It will be appreciated that the peptide of the invention may consist entirely of the region as defined above, or may comprise additional amino acids flanking the region up to a maximum of 30 amino acids.

Peptides longer than 30 amino acids are likely to possess sufficient tertiary structure to cross-link IgG or IgE on cell surfaces resulting in undesirable immune responses such as B cell activation or mast cell degranulation.

Peptide Synthesis

The peptides of the invention are derived in an intellectual sense from the polypeptide which comprises the region as defined above. This is done by making use of the amino acid sequence of the region and synthesising peptides based on the sequence. Peptides may be synthesised using methods well known in the art. Preferred methods include solid-phase peptide synthesis techniques and most preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropyl-ethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, and include t-butyloxycarbonyl (tBoc) and fluorenyl-methoxycarbonyl (Fmoc).

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH$_2$ replaced with —NH(Me) or —N(Me)$_2$).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

Peptides of Interest

Peptides of interest typically comprise at least one free cysteine residue. "Free" typically means that the cysteine residue is available for chemical modification and/or dimerisation with other cysteine-containing peptides in the absence of an agent which inhibits dimer formation. In other words, a free cysteine is one that contains a thiol group in it's reduced from (—SH) and which is able to undergo an oxidation reaction with another cysteine with a thiol group also in the reduced form (—SH) to form a disulfide bond (—S—S—), in the absence of an agent which inhibits dimer formation.

Peptides of interest also typically comprise a region comprising at least one MHC-binding T cell epitope derived from an allergen or allo-antigen. Thus, an aqueous solution comprising the peptides of interest is typically capable of inducing a late phase response in an individual that is sensitised to the allergen. The term "late phase response" includes the meaning as set forth in Allergy and Allergic Diseases (1997) A. B. Kay (Ed.), Blackwell Science, pp 1113-1130. The late phase response may be any late phase response (LPR). Preferably, the compositions comprising an epitope derived from a protein allergen are capable of inducing a late asthmatic response (LAR) or a late rhinitic response, or a late phase skin response or a late phase ocular response. Whether or not a particular composition can give rise to a LPR can be determined using methods well known in the art; a particularly preferred method is that described in Cromwell O, Durham S R, Shaw R J, Mackay J and Kay A B. Provocation tests and measurements of mediators from mast cells and basophils in asthma and allergic rhinitis. In: Handbook of Experimental Immunology (4) Chapter 127, Editor: Weir D M, Blackwell Scientific Publications, 1986. Thus, preferably, the individual compositions of the invention are able to induce a LPR in an individual who has been sensitised to the protein allergen from which the epitope derives.

Whether or not an individual has been sensitised to the protein from which the epitope derives may be determined by well known procedures such as the detection of antibodies in the individual's blood or serum which are specific for the protein. Where the epitope derives from an allergen, suitable tests for sensitisation to the allergen include skin prick testing with solutions of protein extracts, induction of cutaneous LPRs, clinical history, allergen challenge and radioallergosorbent test (RAST) for measurement of protein specific IgE. Whether or not a particular individual is expected to benefit from treatment may be determined by the physician based, for example, on such tests or determinations.

Desensitising or tolerising an individual to the protein from which the epitope derives means inhibition or dampening of immunological tissue reactions induced by said protein in appropriately sensitised individuals. It has been shown that T cells can be selectively activated, and then rendered unresponsive. Moreover the anergising or elimination of these T-cells leads to desensitisation of the patient for a particular protein. The desensitisation manifests itself as a reduction in response to a protein or protein-derived peptide, or preferably an elimination of such a response, on second and further administrations of the protein or protein-derived peptide. The second administration may be made after a suitable period of time has elapsed to allow desensitisation to occur; this is preferably any period between one day and several weeks. An interval of around two weeks is preferred.

Although the compositions of the invention are able to induce a LPR in an individual who has been sensitised to the protein, it should be appreciated that when a composition is used to treat a patient it is preferable that a sufficiently low concentration of the composition is used such that no observable LPR will occur but the response will be sufficient to partially desensitise the T cells such that the next (preferably higher) dose may be given, and so on. In this way the dose is built up to give full desensitisation but often without ever inducing a LPR in the patient. Although, the composition or peptide is able to do so at a higher concentration than is administered.

The composition of the invention typically has a reduced ability to provoke an early phase response in an individual. By "reduced ability to provoke an early phase response", it will be understood that the composition of the invention will result in a lower severity of early phase symptoms (such as basophil or mast cell degranulation) relative to a composition comprising a peptide comprising the same region as that in the composition of the invention, but without modification of its sequence to reduce dimer formation, and lacking an agent which reduces dimer formation. Accordingly, the composition of the invention will produce a lesser early phase response than an equivalent peptide predominantly present in dimeric form. The peptide is equivalent because it comprises the same MHC Class II-binding T cell epitope.

Alternatively or additionally, the composition of the invention typically has an improved ability to induce tolerance in an individual. By "improved ability to induce tolerance", it will be understood that the composition of the invention will produce a greater level of desensitisation in an individual than a composition comprising a peptide comprising the same region as that in the composition of the invention, but without modification of its sequence to reduce dimer formation, and lacking an agent which reduces dimer formation. Accordingly, the composition of the invention will produce a greater level of desensitisation than an equivalent peptide predominantly present in dimeric form. The peptide is equivalent because it comprises the same MHC Class II-binding T cell epitope.

Desensitisation is as defined above, and its level may be characterised by any suitable means. For example, in allergic asthma, a smaller LAR produced in response to inhalation of the protein from which the epitope derives (or a protein-derived peptide) would indicate a greater level of desensitisation following treatment with the composition of the invention. The size of a LAR can be assessed by any suitable means in the art, for example, detection of the reduction in Forced Expired Volume (FEV) of an individual post-administration of protein. A greater reduction in FEV indicates a larger LAR. The composition of the invention preferably results in an LAR at least 10%, 20%, 30%, 40% or 50% smaller than a composition comprising an equivalent peptide predominantly present in dimeric form.

Alternatively, a greater level of desensitisation may be indicated by a greater reduction in the protein-specific production by T cells of inflammatory cytokines such as interferon gamma, interleukin 4 and interleukin 13. Cytokine production by T cells may be detected by any suitable method, for example an ELISA, ELISPOT assay or flow cytometric assay. Particularly preferred methods include Multiplex bead array assays as described in, for example de Jager et al; Clinical and Diagnostic Laboratory Immunology, 2003, Vol 10(1) p. 133-139. By "a greater reduction", it is preferred that treatment with the composition of the invention will result in the production of preferably at least 10%, 20%, 30%, 40% or 50% less inflammatory cytokines than a composition comprising an equivalent peptide predominantly present in dimeric form.

Preferred compositions of the invention comprise at least one peptide comprising or consisting of an epitope which derives from:

- an allergen selected from: a plant allergen (particularly a grass allergen), animal dander allergens, a mold or fungal allergen, a dust allergen, an antibiotic or other drug, a stinging insect venom, an environmental allergen or a food allergen; or
- an antigen selected from the major antigens associated with Acute disseminated encephalomyelitis (ADEM); Addison's disease; Ankylosing spondylitis; Antiphospholipid antibody syndrome (APS); Aplastic anemia; Autoimmune hepatitis; Autoimmune Oophoritis; Coeliac disease; Crohn's disease; Diabetes mellitus type 1; Gestational pemphigoid; Goodpasture's syndrome; Graves' disease; Guillain-Barré syndrome (GBS); Hashimoto's disease; Idiopathic thrombocytopenic purpura; Kawasaki's Disease; Lupus erythematosus; Multiple sclerosis; Myasthenia gravis; Narcolepsy, Opsoclonus myoclonus syndrome (OMS); Optic neuritis; Ord's thyroiditis; Pemphigus; Pernicious anaemia; Polyarthritis in dogs; Primary biliary cirrhosis; Rheumatoid arthritis; Reiter's syndrome; Sjögren's syndrome; Takayasu's arteritis; Temporal arteritis (also known as "giant cell arteritis"); Warm autoimmune hemolytic anemia; or Wegener's granulomatosis Particularly preferred epitopes derive from isoforms of: cat dander protein Fe1 d1; House dust mite proteins Der p 1, Der p 2, Der p 7, Der p 3 to 15, Der p 18, 20, 21 and 23, Der f 1, 2, 7, 10, 11 to 18 and 20 to 22; Ragweed protein amb a 1, 2, 3, 5, 6, 7, 8, 9 and isoforms thereof including amb a 1.1, a 1.2, a1.3 or a1.4; Rye grass proteins 1ol p1 and 1ol p5; Timothy grass proteins ph1 p1 and ph1 p5; Bermuda grass protein Cyn d 5; *Alternaria alternata* proteins Alt a 1, Alt a 2, Alt a 3 to Alt a 10, Alt a 12, Alt a 13 and Enolase (Alt a 6), C1a h 1, 2, 5 to 10, 12, GST, HCh1, HSP70, NTF2, TCTP; Birch protein Bet v1, 2, 3, 4, 6, 7, 8 and P14; German Cockroach proteins B1a g 1, B1a g 2, B1a g 3, B1a g 4, B1a g 5 and B1a g 6, 7, 8, 9, GSTD1, Trypsin; Mugwort protein Art v 1; Russian thistle protein Sal k 1, Sal k 2 and Sal k 8; peanut Ara h1, Ara h2, Ara h3, Ara h4, Ara h5, Ara h6, plant profilins or lipid transfer proteins or a human leukocyte antigen.

Particularly preferred peptides comprise or consist of the sequences of (ordered by reference to the relevant allergic or auto/alloimmune disorder):

| | | SEQ ID: |
|---|---|---|
| | Cat allergy | |
| MLA01 | CPAVKRDVDLFLT | 1 |
| MLA04 | KALPVVLENARILKNCV | 2 |
| MLA05 | RILKNCVDAKMTEEDKE | 3 |
| MLA12 | TAMKKIQDCYVENGLI | 4 |
| MLA15 | ISSSKDCMGEAVQNTV | 5 |
| | House Dust Mite allergy | |
| HDM02 | RTVTPIRMQGGCG | 6 |
| HDM03C | RNQSLDLAEQELVDCASQH | 7 |
| HDM06A | RYVAREQSCRRPN | 8 |
| HDM19 | DQVDVKDCANHEIKK | 9 |
| HDM26 | GVLACAIATHAKIR | 10 |
| HDM20 | CIIHRGKPFQLEA | 11 |
| HDM 100 | RFGISNYCQIYPPNVNK | 12 |
| HDM101 | NYCQIYPPNVNKIREA | 13 |
| HDM102 | NAQRFGISNYCQI | 14 |
| HDM203A | DLRQMRTVTPIRMQGGCGS | 15 |

| | | SEQ ID: |
|---|---|---|
| HDMtre1 | QESYYRYVAREQSCRRPNAQRF | 16 |
| HDMtre2 | EPCIIHRGKPFQLEAVFEANQN | 17 |
| Ragweed allergy | | |
| RGW02A | GSSQIWIDHCSLSKS | 18 |
| RGW02B | GGSQIWIDHCSLSKA | 19 |
| RGW08x | GSSHVTVSNCKF | 20 |
| RGW08A | GSTHVTISNCKF | 21 |
| RGW08B | GSTHFTVSNCLF | 22 |
| RGW12 | DGCWRGKADWAENRKALADCA | 83 |
| Transplant rejection (HLA Class I) | | |
| TRA30 | HAVSDHEATLRCWAL | 23 |
| TRA31 | HPISDHEATLRCWAL | 24 |
| TRA32 | HPVSDHEATLRCWAL | 25 |
| TRA39 | RCWALSFYPAEITLT | 26 |
| TRA40 | RCWALGFYPAEITLT | 27 |
| (Neonatal) Alloimmune Thrombocytopenia (Glycoprotein IIIa) | | |
| AIT | VSPMCAWCSDEALPLGSPRCDLKENLLKD | 28 |
| AITa | VSPMCAWCSDEALPL | 29 |
| NAIT01 | AWCSDEALPL | 30 |
| NAIT01A | AWCSDEALPLGSPR | 31 |
| NAIT02 | AWCSDEALPLGSPRCDLK | 32 |
| NAIT02A | AWSSDEALPLGSPRCDLK | 33 |
| NAIT02B | AWGSDEALPLGSPRCDLK | 34 |
| NAIT02C | AWCSDEALPLGSPRSDLK | 35 |
| NAIT02D | AWCSDEALPLGSPRGDLK | 36 |
| AIT02 | TTRGVSSCQQCLAVS | 37 |
| AIT47 | DLPEELSLSFNATCL | 38 |
| AIT53 | FKDSLIVQVTFDCDC | 39 |
| AIT70 | PGSYEDTCEKCPTCP | 40 |
| AIT77 | DDCVVRFQYYEDSSG | 41 |
| Rhesus D hemolytic disease of the newborn | | |
| RHD28 | AYFGLSVAWCLPKPL | 42 |
| Hemophilia (Factor VIII) | | |
| FAC01 | LCLLRFCFSATRRYYLGAVELSWD | 43 |
| FAC04 | VNGYVNRSLPGLIGCH | 44 |
| FAC06 | ISPITFLTAQTLLMDLGQFLLFC | 45 |
| FAC07 | HDGMEAYVKVDSCPEEPQ | 46 |
| FAC12 | PRCLTRYYSSFVNMERDLASGLIGP | 47 |
| FAC30 | KTAFKKKDTILSLNACESNHA | 48 |
| FAC42 | IARYIRLHPTHYSIRSTLRMELMGC | 49 |
| FAC47 | PQSWVHQIALRMEVLGCEAQD | 50 |
| FACa1 | PRCLTRYYSSFVNME | 59 |
| Grass allergy | | |
| G1 | GDEQKLRSAGELELQFRRVKCKY | 60 |
| G2 | GAYDTYKCIPSLEAAVKQAY | 61 |
| Alternaria allergy | | |
| A1 | SDDITYVATATLPNYCRAGGNGP | 62 |
| A2 | RNGFKRCLQFTLYRPRDLLSLLNE | 63 |
| A3 | AIELKSCNALLLKVNQIGTITEA | 64 |
| A4 | EFIKKAIELKSCN | 65 |
| A5 | IELKSCNALLLK | 66 |
| A6 | CAEYGADLAITYNSRAEGAEKNA | 67 |
| A7 | ATELKGAYVYFASDASSYCTG | 68 |
| A8 | SDDITYVATATLPNYCRAGGNG | 69 |
| A9 | AIHWVNFGIYFNHGQACCAG | 70 |
| A10 | CAEMGAAVAITYASRAQGAEENV | 71 |
| A11 | YNVAKAGCI | 72 |
| A12 | AISWVNFGIFFNHGQCCCAG | 73 |
| A13 | PDTFNYVKKEPIGVCRS | 74 |
| A14 | SYNVAKAGCIHLAK | 75 |
| Birch allergy | | |
| B1 | CNEIKIVATPDGGSI | 76 |
| B2 | CNEIKLVATPDGGST | 77 |
| B3 | CNEIKIVATPDGGCV | 78 |
| B4 | SNEIKIVATPDGGC | 79 |
| B5 | SNEIKIVTTPDGGCV | 80 |
| B6 | CNEIKIVAAPGGGSILK | 81 |
| B7 | AENFRALCTGEKGNG | 82 |

The House Dust Mite sequences shown above typically derive from the mite species *Dermatophagoides pteronyssinus*. Preferred variants of these sequences include homologous sequences derived from the related mite species *Dermatophagoides farinae*. These are indicated in the table below by the identifier "_f".

Other preferred variants of the peptides of the invention include truncations or extensions by 1, 2, 3, 4, 5, 6, 7, 10, 11, 12, 13, 14, 15, 16, or 17 amino acids at the N and/or C terminus of a given peptide. Examples of preferred extensions and truncations of the House Dust Mite peptide HDM03C are also shown below as HDM03M, P and W.

| | | |
|---|---|---|
| HDM03C_f | RNTSLDLSEQELVDCASQH | 51 |
| HDM03M | RNQSLDLAEQELVDCASQHG | 52 |
| HDM03P | SAYLAHRNQSLDLAEQELVDCAS | 53 |
| HDM03W_n | ELVDCASQHG | 54 |
| HDM06_f | PYVAREQRCRRPN | 55 |
| HDM19_f | DQVDVKDCANNEIKK | 56 |
| HDM20_f | CIIHRGKPFTLEA | 57 |
| HDM26A_f | NGVLACAIATHGKIR | 58 |

Where polypeptides comprise residues which are typically difficult to preserve during manufacture, these residues may be replaced. For example, a glutamate or a glutamine residue spontaneously forms pyroglutamate in solution particularly when present at the N terminus of a peptide. Thus, residues of the peptides of the invention which correspond to glutamate or glutamine in the sequence of a native protein sequence may be replaced with pyrogluatmate in the peptides of the invention when such residues are present at the N terminus of a peptide. For example. HDM03W_n (SEQ ID NO:54) may have pyroglutamate in place of E at the N terminus.

In one embodiment, the composition of the invention comprises the peptides of SEQ ID NOS. 1 to 4. The composition may further comprise the peptides of SEQ ID NOS. 83 to 85, and optionally no further peptides.

Other Components

As will be appreciated from the above section relating to freeze-drying, compositions which are to be freeze-dried will typically comprise additional components as well as the biological materials of interest. The present invention relates to the use of a combination of additional components to prevent or reduce dimerisation of the at least one peptide in the compositions of the invention, thereby leading to a more stable freeze-dried composition. The present invention also relates to methods for making such compositions. The present inventors have determined that the combination of (i) a non-reducing carbohydrate and (ii) at least one agent which inhibits dimer formation achieves this effect.

As mentioned herein, carbohydrates and related compounds have the advantage that they are useful as cryo- and lyoprotectants during the freeze-drying process. However, they do not prevent dimer formation by a peptide comprised within the final freeze-dried product during its storage. Additional components are required to achieve this. That is, at least one agent which inhibits dimer formation by peptides must also be included. The agents which inhibit dimer formation in peptide compositions for pharmaceutical purposes must typically be pharmaceutically acceptable. Such agents include agents suitable for reducing a disulfide bond, antioxidant agents or preservative agents. Suitable reducing agents include any trialkylphosphine compound, including tris(2-carboxyethyl)phosphine (TCEP), 2-Mercaptoethanol and dithiothreitol (DTT). Other suitable agents include thioglycerol, thioanisole, and cysteine. Thioglycerol is particularly preferred.

In order to effectively prevent dimer formation, such agents should ideally be present at least at an equivalent molar concentration to that of the material which is susceptible to dimer formation, when measured prior to freezing. Thus, where the material susceptible to dimer formation is one or more peptides comprising at least one free cysteine residue, the agent is present at least at an equivalent molar concentration to the concentration of the one or more peptides comprising at least one free cysteine residue. The concentration of other components, such as peptides which do not contain a free cysteine residue, is not typically taken into account. That is where a composition comprises, for example, four peptides which contain a free cysteine residue and three peptides which do not contain a free cysteine residue, the concentration of the agent which inhibits dimer formation is determined relative to the overall concentration of the four free cysteine-containing peptides. The concentration of the three peptides which do not contain cysteine, and of any other components in the composition, is not relevant to the level of agent required.

In one embodiment the at least one agent which inhibits dimer formation may be present in a greater or lesser amount than the material which is susceptible to dimer formation, when measured prior to freezing, provided that dimer prevention is effectively prevented. In a particular embodiment, the agent is present in a greater amount than the material which is susceptible to dimer formation. For example, the agent may be present at a molar concentration which is at least approximately 10, 20, 30, 40, 50, 60, 70, 80, 90, 100, 150, 200, 250, 300, 400, 500, 600, 700, 800, 900 or 1000 fold greater than the molar concentration of the material which is susceptible to dimer formation. Preferably, the agent is present at a molar concentration which is at least between 60 and 80 fold greater than the molar concentration of the material which is susceptible to dimer formation. For example, where the material is present at a molar concentration of 200 µM, the agent will preferably be present at a molar concentration of between 12 mM and 16 mM.

Such a situation applies in, for example, the Thioglycerol "low" composition in Example 4, wherein four peptides containing at least one free cysteine are each present at 50 µM, and three peptides not containing cysteine are also each present at 50 µM. Thus, in a liter of this composition, there are 350 micromoles of total peptide (seven peptides) and 200 micromoles of peptides with free cysteine (4 peptides with free cysteine). Accordingly, the material susceptible to dimer formation is at 200 µM and thioglycerol is present at a concentration of 14 mM, which is 70 fold greater.

Alternatively the agent may be present at a molar concentration which is at least between 30 and 40 fold greater than the molar concentration of the material which is susceptible to dimer formation. For example, where the material is present at a molar concentration of 400 µM, the agent will preferably be present at a molar concentration of between 12 mM and 16 mM.

Such a situation would apply in, for example, the Thioglycerol "low" composition in Example 4, if all peptides were present at 100 µM rather than 50 µM. That is, in a liter of this composition, there are 700 micromoles of total peptide (seven peptides) and 400 micromoles of peptides with free cysteine (4 peptides with free cysteine). Accordingly, the material susceptible to dimer formation is at 400 µM and thioglycerol is present at a concentration of 14 mM, which is 35 fold greater.

The material is typically at least one peptide comprising at least one free cysteine residue. The lower limit of the amount of peptide present in the composition before freezing as a proportion will typically be about 0.01, 0.02, 0.03, 0.04, 0.05, 0.06, 0.07, 0.08, 0.09, 0.1, 0.15, 0.2, 0.3, 0.4, 0.5, 0.6, 0.7, 0.8, 0.9, 1.0, 1.1, 1.2, 1.3, 1.4, or 1.5% wt/wt or w/v. The upper limit of the amount of peptide present in the composition before freezing as a proportion will typically be about 1.5, 1.6, 1.7, 1.8, 1.9, 2.0, 2.1, 2.2, 2.3, 2.4, 2.5, 3, 4 or 5% wt/wt or w/v. It will be recognised the amount of peptide may typically be between any of the lower limits independently combined with any of the upper limits set out above. The at least one agent which inhibits dimer formation will therefore be present in a similar range as a proportion of the composition, provided the total concentration of agent is at least at an equivalent molar concentration to the total concentration of peptides comprising at least one free cysteine residue in the composition prior to freezing. For example, if the total concentration of peptides comprising at least one free cysteine residue is 0.03 nmol/ml, total agent concentration will be at least 0.03 nmol/ml. If the total concentration of peptides comprising at least one free cysteine residue is 500 nmol/ml, the total agent concentration will be at least 500 nmol/ml.

It will also be appreciated that the at least one agent may typically be included at a higher proportion relative to the peptide as explained above, for example to ensure that dimer formation is effectively reduced. In addition, the upper limit for the total concentration of the agent may typically take account of clinical requirements or limitations as applied to pharmaceutical compositions. For example, a reconstituted solution for injection would typically have no more than 0.5, 0.6, 0.7, 0.8, 0.9, 1.0, 1.5, 2.0, 2.5, 3.0, 3.5 or 4.0% wt/wt or w/v of agent. This corresponds to approximately 5, 6, 7, 8, 9, 10, 15, 20, 25, 30, 35 or 40% wt/wt or w/v, respectively in the freeze-dried product. Accordingly, the amount of peptide in the product may need to be limited to conform with these clinical requirements.

It will be understood by the skilled person that the proportion of any component in the composition before freezing will typically correspond to a proportion about 5 to 10 fold higher in the final freeze-dried composition The difficulty with including at least one agent which inhibits dimer formation in a freeze-dried composition is that, as determined by the present inventors, such agents escape from a freeze-dried product, particularly when said product is stored over extended periods of time at ambient temperatures, or when said product is exposed to sudden increases in temperature. The agents are typically volatile, and thus are not retained in the final product, which either experiences damage and degradation during storage and transport, thereby reducing its stable shelf-life, or is unacceptable for pharmaceutical use. For example, due to changes in the appearance of the freeze-dried composition or the solution reconstituted from it.

In order to overcome this difficulty, the present inventors have devised combinations of non-reducing carbohydrate and dimer inhibiting agents which do not result in escape of said agents from a final freeze-dried product. In order to achieve this, it is necessary that the freeze-dried composition has an amorphous structure. Accordingly, a non-reducing carbohydrate which is particularly suitable for use in the present invention is a carbohydrate which is amorphous upon freeze-drying, referred to hereinafter as an "amorphous carbohydrate". In order to ensure that the composition as a whole has an amorphous structure upon freeze-drying, the amorphous carbohydrate or carbohydrates in the compositions of the invention should typically present at an amount which is at least 50%, but more preferably at least 60%, 70%, or 80% and most preferably at least 90% as a proportion of the total components of the freeze-dried composition.

Alternatively, an overall amorphous structure could be achieved with a proportion of amorphous carbohydrate which is below 50% as a proportion of the total components of the composition. This can be achieved if the amorphous carbohydrate is used in combination with a carbohydrate which is crystalline upon freeze-drying, referred to hereinafter as a "crystalline carbohydrate". However, for such a combination to retain some amorphous structure in which the biological molecules or interest are dispersed, it will typically be necessary to carry out a cyclical heating and cooling of the composition during the freezing stage of the freeze-drying process. This cyclical heating and cooling is typically referred to as annealing, and when carried out at appropriate conditions it can result in the formation of a mixed crystalline/amorphous cake structure. In this instance, the amorphous carbohydrate or carbohydrates in the compositions of the invention would typically present at an amount which is at least 20% as a proportion of the total components of the composition.

Particularly preferred carbohydrates for the uses of the invention include maltulose, iso-maltulose, lactulose and sucrose, maltose, lactose, isomaltose and sugar alcohols thereof, maltitol, lactitol, palatinit, a mixture of α-D-glucopyranosyl-mannitol, and α-D-glucopyranosyl-sorbitol, and its individual sugar alcohols, non-reducing glycosides of polyhydroxy compounds selected from sugar alcohols, other straight chain polyalcohols, trehalose, sucrose, raffinose, stachyose, melezitose and dextran.

Preferred carbohydrates are non-reducing di-, tri and tetrasaccharides including trehalose, sucrose, raffinose, stachyose, and melezitose. Trehalose is particularly preferred.

Ideally, the carbohydrate should have a Tg (Glass Transition Temperature) at least 5, 10, 15, or most preferably 20° C. above the highest anticipated storage temperature of the final freeze-dried product for best stability. Reported values for Tg and related parameters for some preferred carbohydrates are shown below.

| Compound | Tg (° C.) | Tg' |
|---|---|---|
| Sucrose | 43-65 | Approx. −46 |
| Raffinose | 70-106 | Approx. −36 |
| Trehalose | 63-115 | Approx. −27 |
| Melezitose | >100 | |
| Stachyose | 81-123 | |

Tg = glass transition temperature;
Tg' = Tg for the maximally freeze concentrated state;

As demonstrated herein, the amorphous structure of the freeze-dried carbohydrate traps the agent which inhibits dimer formation within the final freeze-dried product. This is by contrast to materials which have a crystalline structure upon freeze-drying. Crystalline or mixed/amorphous materials have previously been preferred for freeze-drying applications of the type described herein, in part because the final freeze-dried "cake" typically has a more attractive appearance and shorter more aggressive drying cycles may be employed.

Thus, the present invention relates to use of (i) at least one non-reducing carbohydrate and (ii) at least one agent which inhibits dimer formation in a freeze-dried composition comprising at least one peptide comprising a free cysteine residue, wherein the use is for preventing or reducing dimerisation of said at least one peptide in said composition. The at least one agent which inhibits dimer formation is retained in the freeze-dried product by the amorphous structure of the at least one carbohydrate, and is thereby able to reduce or prevent dimerisation of the peptide or peptides therein throughout the storage life of the product. In this way, a stable shelf-life is achieved which is ideally at least 1 year, or at least 2 years, at 5±3° C., 25° C./60% RH, 30° C./65% RH or 40° C./75% RH.

In accordance with the above, a preferred embodiment of the invention relates to the use of (i) at least one non-reducing carbohydrate selected from trehalose, sucrose, raffinose, stachyose or melezitose and (ii) thioglycerol, in a freeze-dried composition comprising at least one peptide comprising at least one free cysteine residue, wherein the use is for preventing or reducing dimerisation of said at least one peptide in said composition.

In a particularly preferred embodiment, the non-reducing carbohydrate is trehalose or sucrose, most preferably trehalose.

Whilst not wishing to be bound by any specific hypothesis, the inventors consider that this embodiment is particularly advantageous because of the good retention of thioglycerol in the freeze-dried cake. Thioglycerol had previously been considered less suitable for incorporation in freeze-dried compositions because it does not itself freeze to form a glass under typical freeze-drying conditions, i.e. it remains liquid at temperatures as low as −80° C. However, in the present invention, it is demonstrated that thioglycerol can be retained, particularly in combination with trehalose, without any signs of escape or negative impact on the physical quality of the freeze-dried cake. The presence of thioglycerol effectively prevents formation of peptide dimers in the composition.

Reconstituted Compositions of the Invention

It will be appreciated that the freeze-dried compositions made according to the invention may be reconstituted in solution, typically in an aqueous solution suitable for injection, such as sterile, pyrogen-free water. Ideally, the solution will be isotonic/iso-osmolar and thereby suitable for parenteral injection.

The reconstituted composition will typically have a minimal proportion of peptide present as a dimer. That is, dimer formation will be effectively prevented. By a minimal proportion of peptide present as a dimer it is meant that a maximum of 5%, 4%, 3%, 2%, 1%, 0.9%, 0.8%, 0.7%, 0.6%, 0.5%, 0.4%, 0.3%, 0.2%, 0.1%, 0.05% or 0.01% is present in solution as a dimer. It will be understood that the proportion of peptide present as a dimer in solution will be the proportion present as a dimer following a suitable period of time in solution. Suitable periods of time include ranges of time that a skilled practitioner might reasonably expect to keep a sequence in solution prior to use. For example, about 24 hours, about 48 hours, or about 72 hours. The proportion of a peptide present in a given form may be assessed by any suitable method.

The reconstituted composition will typically be a pharmaceutical formulation. for tolerising or immunising an individual to a protein from which a peptide comprised in the composition derives. As such, the reconstituted composition may comprise one or more pharmaceutically acceptable carriers or diluents and optionally one or more other therapeutic ingredients. The carrier (s) must be 'acceptable' in the sense of being compatible with the other ingredients of the formulation (in particular they must not promote dimer formation) and not deleterious to the recipient thereof. Typically, carriers for injection, and the final formulation, are sterile and pyrogen free. The additional components may have been present in the freeze-dried composition or may be added during or following reconstitution. Thus, auxiliary substances, such as wetting or emulsifying agents, pH modifying or buffering substances, antioxidants, chelating agents and the like, may be present. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

The compositions of the invention will comprise a suitable concentration of each peptide to be effective without causing adverse reaction. Typically, for use in tolerisation, the concentration of each peptide in the composition will be in the range of 0.03 to 500 nmol/ml or 0.03 to 200 nmol/ml. More preferably in the range of 0.3 to 200 nmol/ml, 3 to 180 nmol/ml, 10 to 150 nmol/ml or 30 to 120 nmol/ml. Particularly preferred is the range 3 to 12 nmol/ml. The composition should have a purity of greater than 90%, or 95% or 98% or a purity of at least 99%. Injection volumes may typically be 60 μl or 120 μl.

A composition may therefore be formulated which comprises a molecule and/or cell of the invention and also one or more other therapeutic molecules. A composition of the invention may alternatively be used simultaneously, sequentially or separately with one or more other therapeutic compositions as part of a combined treatment.

Typically, for use in immunisation, the composition will provide a presentation that once reconstituted that allows the administration of between 1 μg and 10 mg of each peptide. More preferably an amount of each peptide in the range 3 μg to 5 mg, 5 μg to 5 mg, 10 μg to 2 mg or 20 μg to 1 mg. The concentration of each peptide will be dependent upon the route of administration, but may typically be delivered intradermally, subcutaneously, intramuscularly, intravenously, orally, intranasally or by inhalation. The composition should have a purity of greater than 90%, or 95% or 98% or a purity of at least 99%.

Therapeutic Methods and Individual to be Treated

The present invention relates to compositions comprising at least one peptide that is capable of modulating the immune system of an individual.

"Modulating" may mean sensitizing or inducing immunity in individuals to a protein from which the at least one peptide of the compositions of the invention derives. In this instance, the protein is typically a tumour antigen protein or an antigen protein from an infectious disease, such as those caused by hepatitis and human papilloma viruses. The compositions of the invention are therefore useful in the prevention or treatment of cancer or infectious diseases.

Alternatively, "modulating" may mean desensitising or tolerising individuals to a protein from which the at least one peptide of the compositions of the invention derives. In this instance, the protein is typically an allergen or other antigen to which an immune response is undesirable. Examples of such antigens include antigens associated with autoimmune diseases, antigens associated with graft-versus-host disease or transplant rejection (herein referred to as alloimmune conditions) and antigens associated with maternal-foetal immune responses, for example Rhesus D Haemolytic Disease of the Newborn. The compositions of the invention are therefore useful in the prevention or treatment an allergic disease, an autoimmune disease, an alloimmune condition or a maternal-foetal immune response.

The invention provides compositions for use in preventing or treating the above conditions. The invention also provides a method of preventing or treating a subject having the above conditions, comprising administering a reconstituted composition of the invention. The individual to be treated or provided with the composition of the invention is preferably human.

Where desensitisation/tolerisation is desired, it will be appreciated that the individual to be treated may be known to be sensitised to the particular allergen or antigen, at risk of being sensitised or suspected of being sensitised. The individual can be tested for sensitisation using techniques well known in the art and as described herein. Alternatively, the individual may have a family history of the conditions described above. It may not be necessary to test an individual for sensitisation to allergens because the individual may display symptoms of allergy when brought into proximity to a suitable allergen source. By proximity is meant 10 meters or less, 5 meters or less, 2 meters or less, 1 meter or less, or 0 meters from the source. Symptoms of allergy can include itchy eyes, runny nose, breathing difficulties, red itchy skin or rash. The individual to be treated for allergic disease may have had allergy for at least 2 weeks, 1 month, 6 months, 1 year or 5 years. The individual may suffer from a rash, nasal congestion, nasal discharge and/or coughing caused by the allergy. The individual may or may not have been administered with other compositions/compounds which treat allergy.

In general, the individual to be treated may be of any age. However, preferably, the individual may be in the age group of 1 to 90, 5 to 60, 10 to 40, or more preferably 18 to 35. Preferably, the individual to be treated is from a population that has MHC allele frequencies within the range of frequencies that are representative of the Caucasian population. Reference population allele frequencies for 11 common DRB1 allele families are shown below:

| DRB1 | 1 | 3 | 4 | 7 | 8 | 11 | 12 | 13 | 14 | 15 | 16 |
|---|---|---|---|---|---|---|---|---|---|---|---|
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MHC allele frequencies as the reference population for the alleles referred to in the above table (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:
4—at least 9%
7—at least 10%
11—at least 8%.

The invention is particularly suitable for use with individuals who may need to receive multiple administrations of the compositions of the invention as described above. Peptides which are more prone to dimer formation than the peptides of the invention are more likely to induce an adverse response in an individual receiving multiple administrations. Since monomeric peptides are typically less inflammatory than dimeric peptides, the invention is also particularly suitable for administration to an individual who has or is at risk of a condition, wherein the condition is characterised by an adverse inflammatory reaction to a treatment comprising a peptide. An adverse inflammatory reaction to a treatment comprising a peptide may be diagnosed as a result of the onset of any of the symptoms of allergy as defined above following administration of a treatment comprising a peptide. An individual may be considered to be at risk of such a reaction for any suitable medical reason, for example, a family history of similar reactions, a personal medical history of multiple allergic responses, or strongly positive skin prick or skin patch responses to common allergens.

The following Examples illustrate the invention:

EXAMPLES

The following examples and comparative examples show the performance of different compositions under different storage conditions. Each of the different compositions comprises the peptides consisting of the sequences of SEQ ID NOS: 1 to 4 (peptides MLA01, 04, 05 and 12), and three additional peptides: MLA03 (EQVAQYKALPVVLENA (SEQ ID NO: 84)), MLA07 (KENALSLLDKIYTSPL (SEQ ID NO: 85)) and MLA14 (SRVLDGLVMTTISSSK (SEQ ID NO: 86)).

In every case, the composition was prepared in solution prior to being subjected to freeze-drying. Freeze-drying conditions were selected as appropriate for each composition and a typical freeze-drying cycle is shown for each. Degradation of peptides during the freeze-drying process was measured by comparing the level of peptide degradation in a sample of solution before and after the process. All compositions tested experienced only minor degradation of peptides during the freeze-drying process (data not shown).

Following freeze-drying, a sample of each composition was stored at a variety of different conditions (−80° C., 5° C., 25° C./65% RH, 40° C./75% RH) (RH: relative humidity) for up to 28 weeks. The degradation during storage of the final freeze-dried product was monitored by reconstituting a sample at intervals and comparing the level of peptide degradation to that in a freshly prepared standard solution of MLA07.

In each composition tested, the only volatile component is thioglycerol. Accordingly, retention of thioglycerol is determined by observing the presence or absence of condensation on the walls of the storage vials.

Example 1

Trehalose Formulation

Typical Freeze-Drying Cycle

| Step | Shelf Temp (° C.) | Chamber pressure (mbar) | Duration (h · min) |
|---|---|---|---|
| 1 | 20 | 1000 | 0 |
| 2 | −40 | 1000 | 00.36 |
| 3 | −40 | 1000 | 1.30 |
| 4 | −24 | 0.05 | 2.00 |
| 5 | −24 | 0.05 | 24.00 |
| 6 | 24 | 0.05 | 9.20 |
| 7 | 24 | 0.05 | 6.00 |

Non-peptide components (values in brackets indicate concentrations in mM) trehalose/thioglycerol/methionine (250:46:5).

Characteristics
Tg'=−31.9° C.
Tg=83-87° C. (first run)
Residual moisture=nd
WAXS diffractogram: fully amorphous Retention of thioglycerol is excellent. No condensation is visible on vial walls for all storage conditions. The thioglycerol is evidently immobilised within the amorphous cake.

Figure 4:
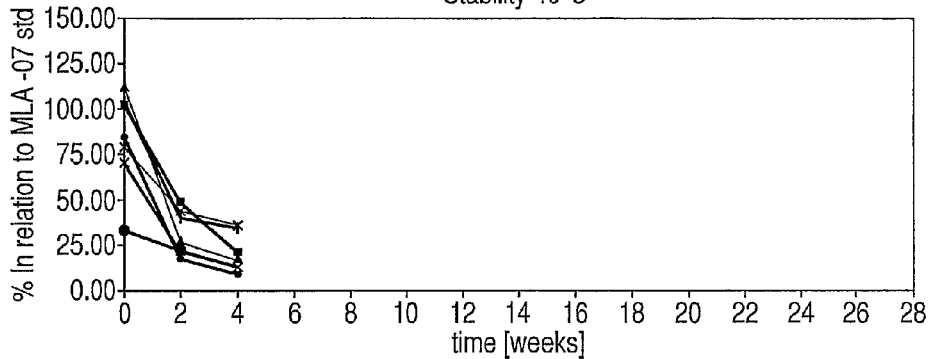
Figure 5:
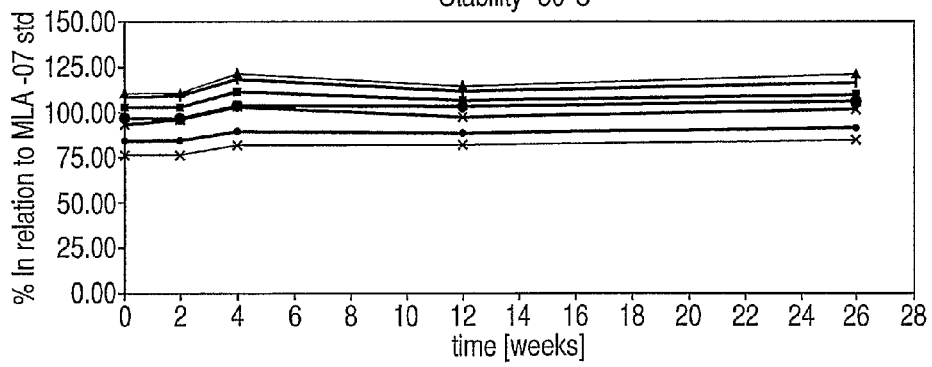
Figure 6:
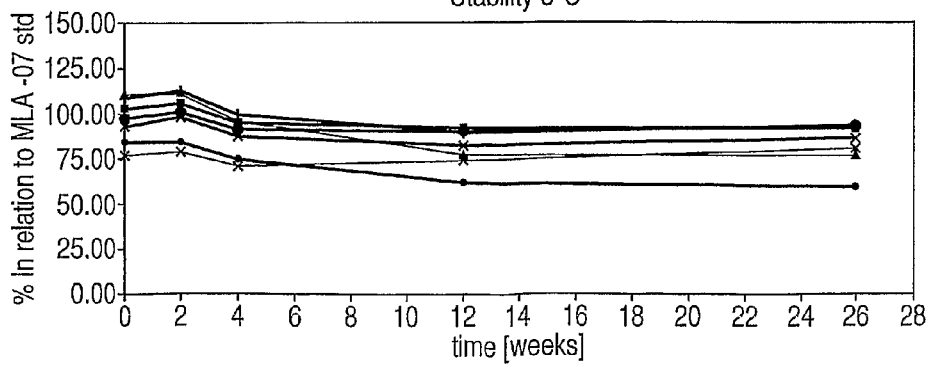
Figure 7:
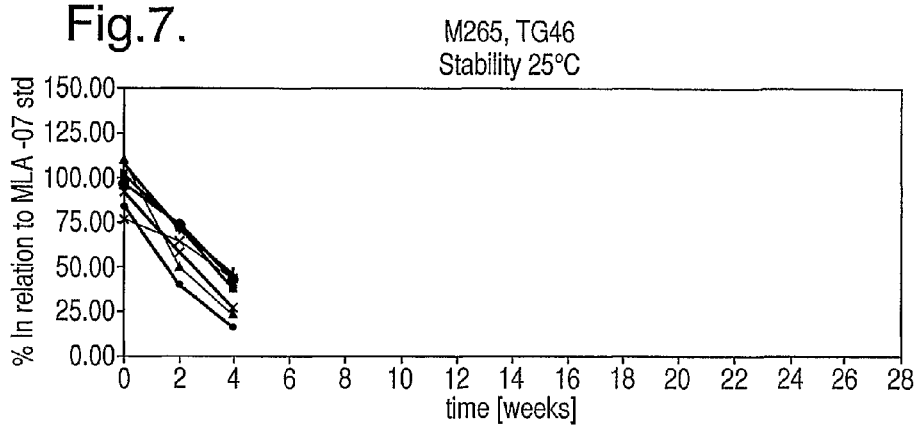
Figure 8:
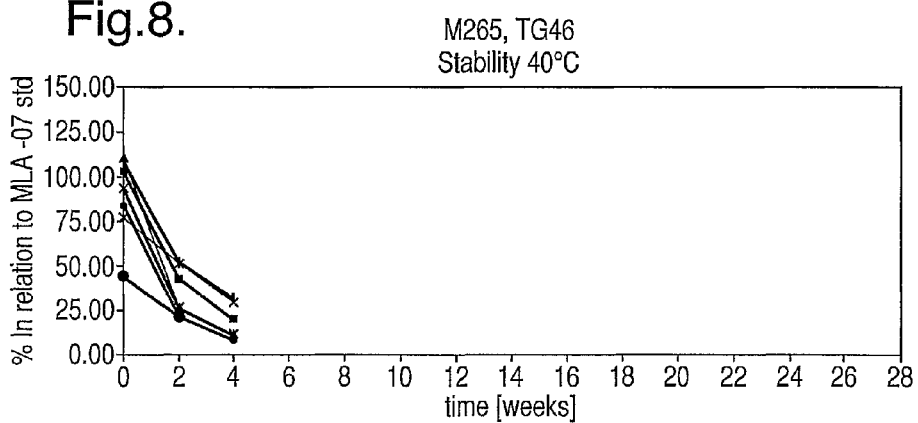
Figure 9:
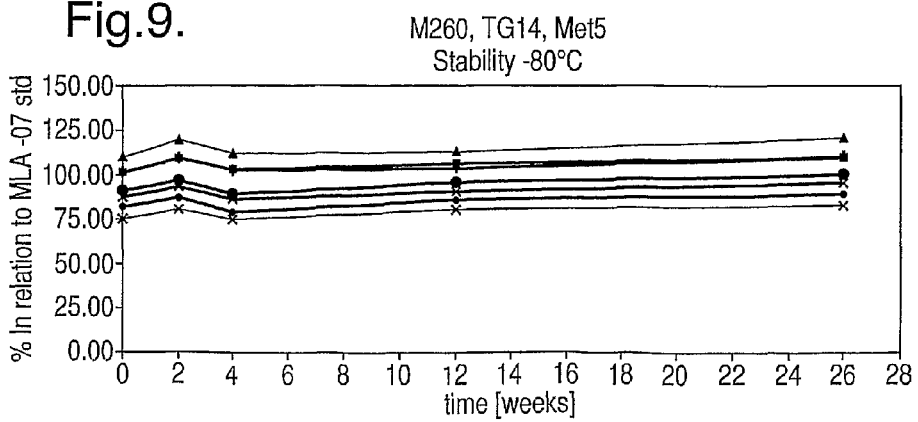
Figure 13:
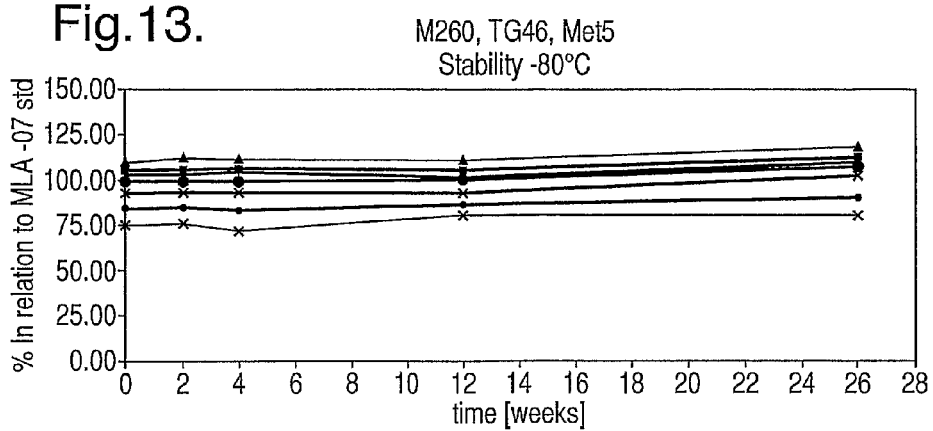
Figure 14:
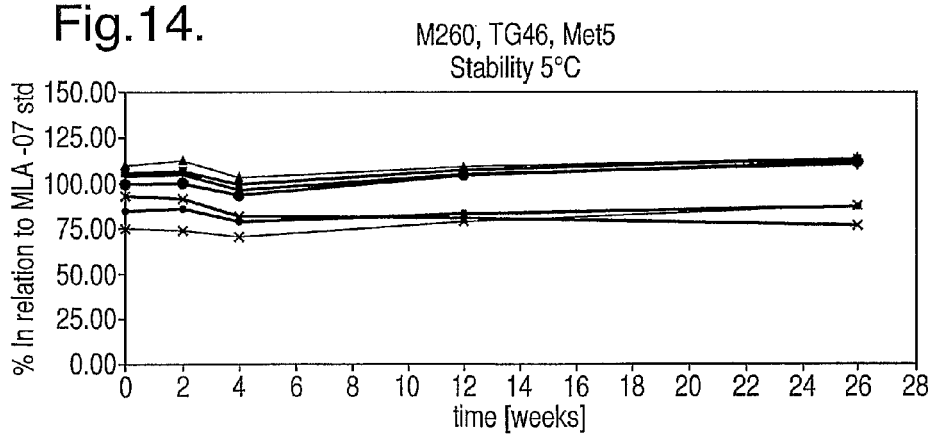
Figure 15:
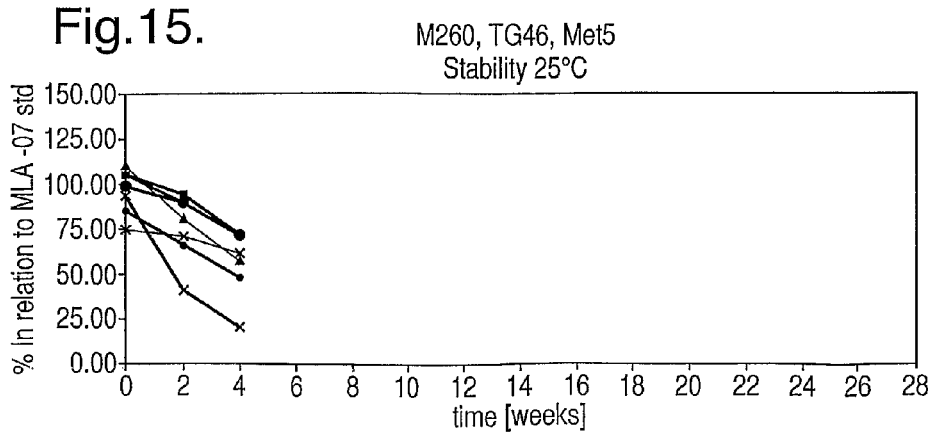
Figure 16:
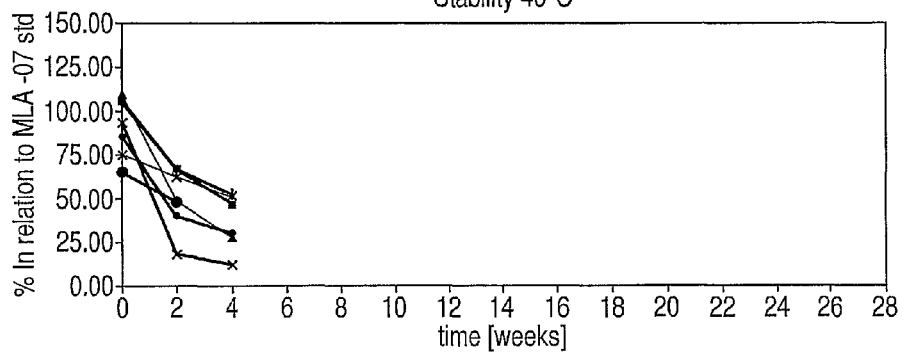
Figure 17:
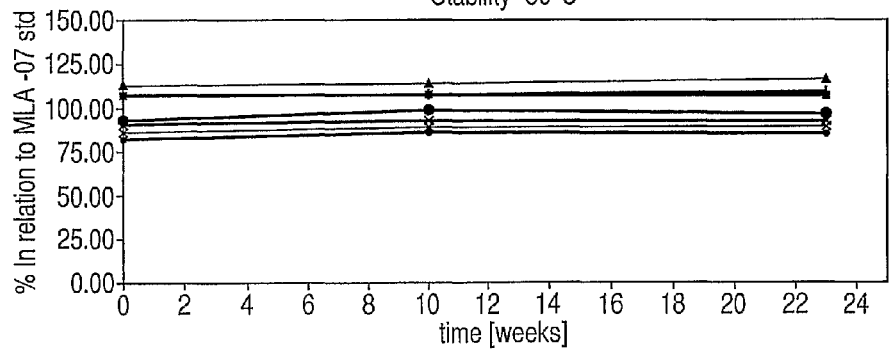
Figure 18:
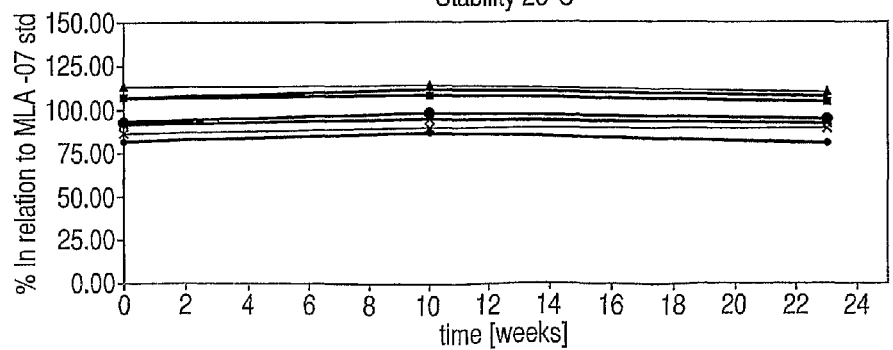
Figure 49:
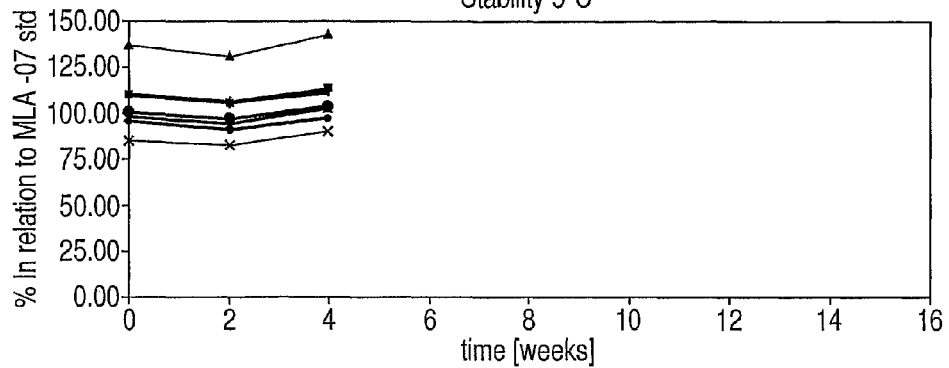
Figure 50:
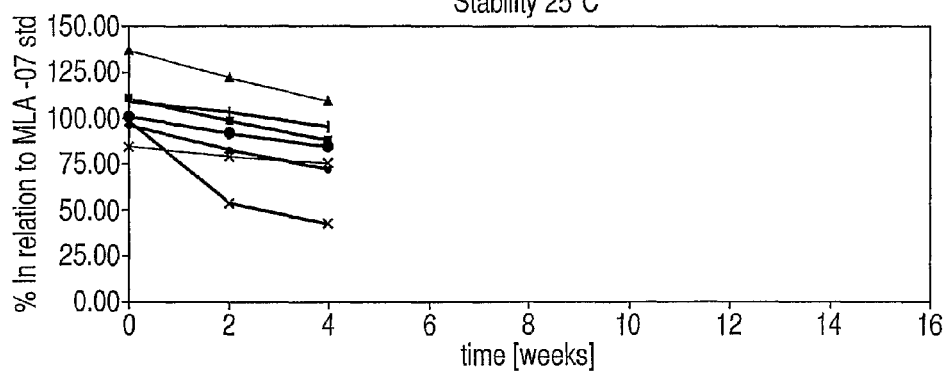
Figure 51:
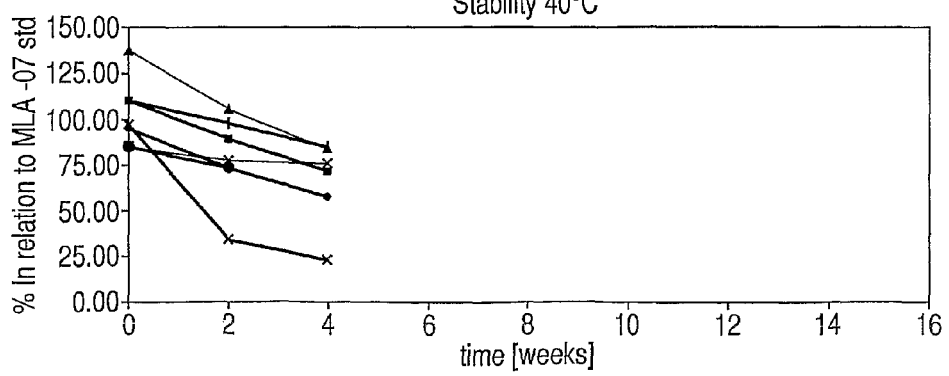
Figure 58:
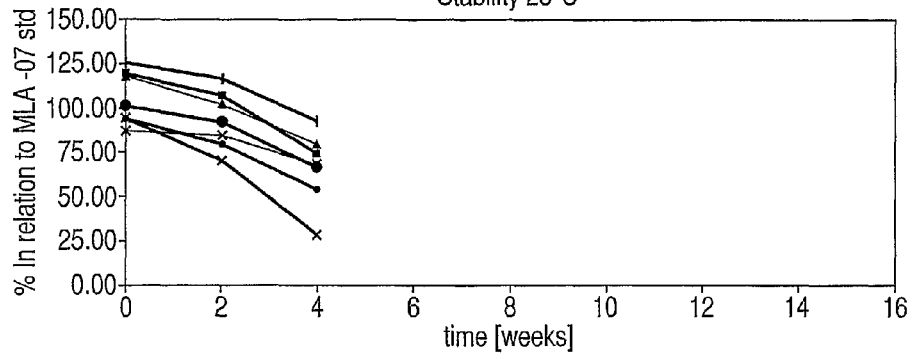
Figure 59:
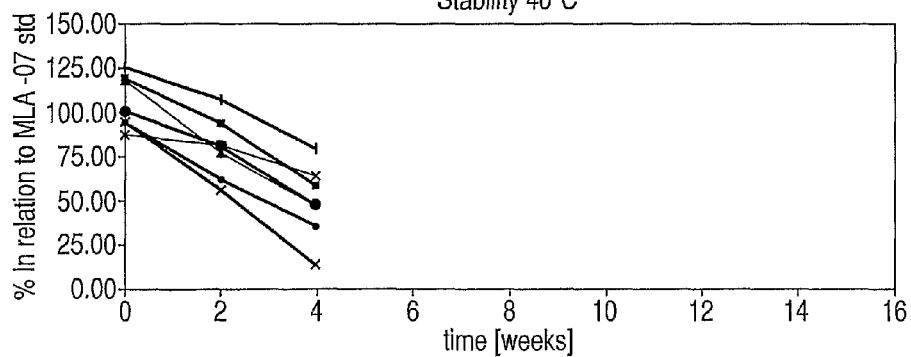
Figure 60:
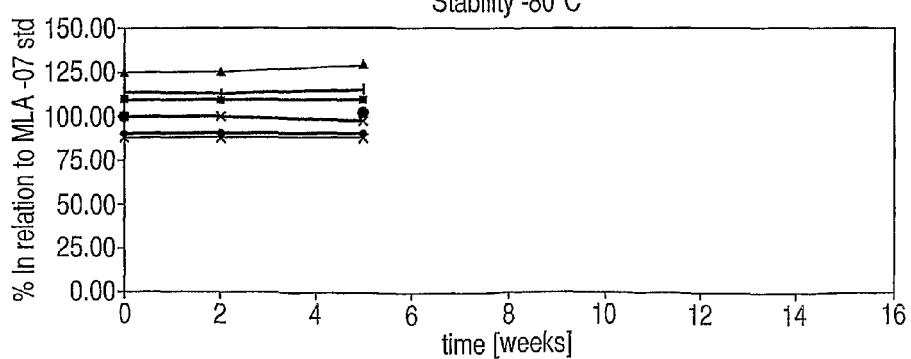

Cake appearance is cracked and so not aesthetically pleasing, but storage stability is excellent as shown in FIGS. 17 to 19. No significant peptide degradation was observed apart from for the most extreme conditions tested (40° C./75% RH) after approx. 8 weeks.

Example 2

'Amorphous' Binary Mixture Series

Typical Freeze-Drying Cycle

| Step | Shelf Temp (° C.) | Chamber pressure (mbar) | Duration (h · min) |
|---|---|---|---|
| 1 | −40 | 1000 | 0 |
| 2 | −40 | 1000 | 1.00 |
| 3 | −15 | 0.03 | 0.30 |
| 4 | −15 | 0.03 | 20.00 |
| 5 | 30 | 0.03 | 0.25 |
| 6 | 30 | 0.03 | 8.00 |

2A

Non-peptide components (values in brackets indicate concentrations in mM) trehalose/glycine/thioglycerol/methionine (165:95:46:5)
Characteristics
Tg'=−36.7° C.
Tg=62.5° C.
Residual moisture=0.61% w/v
Cake structure: fully amorphous Retention of thioglycerol is excellent. No condensation is visible on vial walls for all storage conditions. The thioglycerol is evidently immobilised within the amorphous cake.

Cake appearance is cracked and so not aesthetically pleasing, but storage stability is excellent as shown in FIGS. 20 to 23. No significant peptide degradation was observed apart from for the most extreme conditions tested (40° C./75% RH), at which continual decline in peptide content was observed.

2B

Non-peptide components (values in brackets indicate concentrations in mM) sucrose/glycine/thioglycerol/methionine (182:78:46:5)
Characteristics
Tg'=−37.8° C.
Tg=38.6° C.
Residual moisture=0.56% w/v
WAXS diffractogram: fully amorphous Retention of thioglycerol is less good than Example 2A, condensation is visible on vial walls stored at 25° C./65% RH. The thioglycerol is evidently not completely immobilised within the amorphous cake.

Cake appearance is cracked and so not aesthetically pleasing, but storage stability is good as shown in FIGS. 24 to 27. Significant peptide degradation was only observed for the most extreme conditions tested: 25° C./65% RH (which showed a clear decline particularly after 5 weeks) and 40° C./75% RH (which showed very poor peptide stability).

2C

Non-peptide components (values in brackets indicate concentrations in mM) trehalose/mannitol/thioglycerol/methionine (160:100:46:5)
Characteristics
Tg'=−36.6° C.
Tg=51.6° C.
Residual moisture=0.42% w/v
WAXS diffractogram: fully amorphous Retention of thioglycerol is less good than Example 2A, condensation is visible on vial walls stored at 25° C./65% RH. The thioglycerol is evidently not completely immobilised within the amorphous cake.

Cake appearance is cracked and so not aesthetically pleasing, but storage stability is good as shown in FIGS. 28 to 31. No significant peptide degradation was observed apart from for the most extreme conditions tested (40° C./75% RH), at which continual decline in peptide content was observed. Stability at 25° C./65% RH was good, although not as good as for Example 2A.

2D

Non-peptide components (values in brackets indicate concentrations in mM) sucrose/mannitol/thioglycerol/methionine (150:110:46:5)
Characteristics
Tg'=−38.7° C.
Tg=nd (<25° C.)
Residual moisture=0.34% w/v
WAXS diffractogram: fully amorphous Retention of thioglycerol is less good than Example 2A, condensation is visible on vial walls stored at 25° C./65% RH. The thioglycerol is evidently not completely immobilised within the amorphous cake.

Cake appearance is cracked and so not aesthetically pleasing, but storage stability is less good than other formulations as shown in FIGS. 32 to 35. Peptide degradation was only observed at 25° C./65% RH (poor stability) and 40° C./75% RH (very poor stability).

Comparative Example 1

Mannitol Series

Typical Freeze-Drying Cycle

| Step | Shelf Temp (° C.) | Chamber pressure (mbar) | Duration (h · min) |
|---|---|---|---|
| 1 | 20 | 1000 | 0 |
| 2 | −5 | 1000 | 00.25 |
| 3 | −5 | 1000 | 00.30 |
| 4 | −40 | 1000 | 1.10 |
| 5 | −40 | 1000 | 1.00 |
| 6 | −20 | 1000 | 0.20 |
| 7 | −20 | 1000 | 4.30 |
| 8 | −40 | 1000 | 0.20 |
| 9 | −40 | 1000 | 1.00 |
| 10 | −15 | 0.09 | 0.50 |
| 11 | −15 | 0.09 | 14.00 |
| 12 | 25 | 0.05 | 6.00 |
| 13 | 25 | 0.05 | 12.00 |

C1A
Non-peptide components (values in brackets indicate concentrations in mM) mannitol/thioglycerol (265:14)
Characteristics
Tg'=none
Tg=none
Residual moisture=0.75% w/v
Cake structure: crystalline Retention of thioglycerol is poor. Condensation is visible on vial walls for all storage conditions. The thioglycerol is evidently not immobilised within the crystalline cake.

Cake appearance is good and so is aesthetically pleasing, but storage stability is poor as shown in FIGS. 1 to 4. Significant peptide degradation was observed at all conditions apart from the most favourable (−80° C.). This storage condition is unlikely to be commercially viable for a pharmaceutical product.

C1B
Non-peptide components (values in brackets indicate concentrations in mM) mannitol/thioglycerol (265:46)
Characteristics
Tg'=none
Tg=none
Residual moisture=0.33% w/v
Cake structure: crystalline Retention of thioglycerol is poor. Condensation is visible on vial walls to similar degree as for C1A. The thioglycerol is evidently not immobilised within the crystalline cake even when present at a higher.

Cake appearance is good and so is aesthetically pleasing, but storage stability is poor as shown in FIGS. 5 to 8. Significant peptide degradation was observed at all conditions apart from the most favourable (−80° C.).

C1C
Non-peptide components (values in brackets indicate concentrations in mM) mannitol/thioglycerol/methionine (265:14:5)
Characteristics
Tg'=none
Tg=none
Residual moisture=1.04% w/v
Cake structure: crystalline Retention of thioglycerol is poor. Condensation is visible on vial walls to similar degree as for C1A. The thioglycerol is evidently not immobilised within the crystalline cake in the presence of methionine.

Cake appearance is good and so is aesthetically pleasing, but storage stability is poor as shown in FIGS. 9 to 12. Significant peptide degradation was observed at all conditions apart from the most favourable (−80° C.). Methionine has not improved the properties of this composition.

C1D
Non-peptide components (values in brackets indicate concentrations in mM) mannitol/thioglycerol/methionine (265:46:5)
Characteristics
Tg'=none
Tg=none
Residual moisture=0.61% w/v
Cake structure: crystalline Retention of thioglycerol is poor. Condensation is visible on vial walls to similar degree as for C1A. The thioglycerol is evidently not immobilised within the crystalline cake even when present at a higher concentration and in the presence of methionine.

Cake appearance is good and so is aesthetically pleasing, but storage stability is poor as shown in FIGS. 13 to 16. Significant peptide degradation was observed at all conditions apart from the most favourable (−80° C.). Methionine has not improved the properties of this composition.

Comparative Example 2

'Crystalline' Binary Mixture Trehalose Series

Typical Freeze-Drying Cycle

| Step | Shelf Temp (° C.) | Chamber pressure (mbar) | Duration (h · min) |
|---|---|---|---|
| 1 | 20 | 1000 | 0 |
| 2 | −40 | 1000 | 00.36 |
| 3 | −40 | 1000 | 1.30 |
| 4 | −24 | 0.05 | 2.00 |
| 5 | −24 | 0.05 | 24.00 |
| 6 | 24 | 0.05 | 9.20 |
| 7 | 24 | 0.05 | 6.00 |

C2A
Non-peptide components (values in brackets indicate concentrations in mM) mannitol/trehalose/thioglycerol/methionine (245:10:46:5)
Characteristics
Tg'=−58.3° C.
Tg=70-73° C.
Tm=ca. 160° C.
Residual moisture=0.11% w/v
Cake structure: crystalline (not fully)

Retention of thioglycerol is poor. Condensation is visible on vial walls after 6 weeks at 25° C. and 40° C. The thioglycerol is evidently not immobilised within the crystalline cake.

Cake appearance is good and so is aesthetically pleasing, but storage stability is poor as shown in FIGS. 36 to 39. Significant peptide degradation was observed at all conditions apart from the two most favourable (5° C. and −80° C.).

C2B
Non-peptide components (values in brackets indicate concentrations in mM) mannitol/trehalose/thioglycerol/methionine (235:20:46:5)
Characteristics
Tg'=nd
Tg=nd
Tm=nd
Residual moisture=nd
Cake structure: crystalline (not fully)

Retention of thioglycerol is poor. Condensation is visible on vial walls especially at 25° C. and 40° C. The thioglycerol is evidently not immobilised within the crystalline cake even at a higher concentration of trehalose.

Cake appearance is good and so is aesthetically pleasing, but storage stability is poor as shown in FIGS. 40 to 43. Significant peptide degradation was observed at all conditions apart from the two most favourable (5° C. and −80° C.).

C2C
Non-peptide components (values in brackets indicate concentrations in mM) mannitol/trehalose/thioglycerol/methionine (225:30:46:5)
Characteristics
Tg'=nd
Tg=nd
Tm=nd
Residual moisture=nd
Cake structure: crystalline (not fully)

Retention of thioglycerol is poor. Condensation is visible on vial walls especially at 25° C. and 40° C. The thioglycerol is evidently not immobilised within the crystalline cake even at a still higher concentration of trehalose.

Cake appearance is good and so is aesthetically pleasing, but storage stability is poor as shown in FIGS. 44 to 47. Significant peptide degradation was observed at all conditions apart from the two most favourable (5° C. and −80° C.).

C2D

Non-peptide components (values in brackets indicate concentrations in mM) mannitol/trehalose/thioglycerol/methionine/EDTA (245:10:46:5:0.5)

Characteristics

Tg'=nd

Tg=nd

Tm=nd

Residual moisture=nd

Cake structure: crystalline (not fully)

Cake appearance is good and so is aesthetically pleasing, but storage stability is poor as shown in FIGS. 48 to 51. Significant peptide degradation was observed at all conditions apart from the two most favourable (5° C. and −80° C.). Addition of EDTA does not affect the properties of this composition.

C2E

Non-peptide components (values in brackets indicate concentrations in mM) mannitol/trehalose/thioglycerol/methionine/EDTA (235:20:46:5:0.5)

Characteristics

Tg'=nd

Tg=nd

Tm=nd

Residual moisture=nd

Cake structure: crystalline (not fully)

Cake appearance is good and so is aesthetically pleasing, but storage stability is poor as shown in FIGS. 52 to 55. Significant peptide degradation was observed at all conditions apart from the two most favourable (5° C. and −80° C.). Addition of EDTA does not affect the properties of this composition.

C2F

Non-peptide components (values in brackets indicate concentrations in mM) mannitol/trehalose/thioglycerol/methionine/EDTA (225:30:46:5:0.5)

Characteristics

Tg'=nd

Tg=nd

Tm=nd

Residual moisture=nd

Cake structure: crystalline (not fully)

Retention of thioglycerol is poor. Condensation is visible on vial walls especially at 25° C. and 40° C. The thioglycerol is evidently not immobilised within the crystalline cake even at a high concentration of trehalose and in the presence of EDTA.

Cake appearance is good and so is aesthetically pleasing, but storage stability is poor as shown in FIGS. 56 to 59. Significant peptide degradation was observed at all conditions apart from the most favourable (−80° C.). Addition of increased levels of EDTA does not significantly affect the properties of this composition.

Comparative Example 3

'Crystalline' Binary Mixture Sucrose Series

Typical Freeze-Drying Cycle

| Step | Shelf Temp (° C.) | Chamber pressure (mbar) | Duration (h · min) |
|---|---|---|---|
| 1 | 20 | 1000 | 0 |
| 2 | −40 | 1000 | 00.36 |
| 3 | −40 | 1000 | 1.30 |
| 4 | −24 | 0.05 | 2.00 |
| 5 | −24 | 0.05 | 24.00 |
| 6 | 24 | 0.05 | 9.20 |
| 7 | 24 | 0.05 | 6.00 |

C3A

Non-peptide components (values in brackets indicate concentrations in mM) mannitol/sucrose/thioglycerol/methionine (250:10:46:5)

Characteristics

Tg'=nd

Tg=nd

Tm=nd

Residual moisture=nd

Cake structure: crystalline (not fully)

Retention of thioglycerol is poor. Condensation is visible on vial walls after 5 weeks at 25° C. and 40° C. The thioglycerol is evidently not immobilised within the crystalline cake.

Cake appearance is good and so is aesthetically pleasing, but storage stability is poor as shown in FIGS. 60 to 63. Significant peptide degradation was observed at all conditions apart from the two most favourable (5° C. and −80° C.).

C3B

Non-peptide components (values in brackets indicate concentrations in mM) mannitol/sucrose/thioglycerol/methionine (235:20:46:5)

Characteristics

Tg'=nd

Tg=nd

Tm=nd

Residual moisture=nd

Cake structure: crystalline (not fully)

Retention of thioglycerol is poor. Condensation is visible on vial walls especially at 25° C. and 40° C. The thioglycerol is evidently not immobilised within the crystalline cake even at a higher concentration of sucrose.

Cake appearance is good and so is aesthetically pleasing, but storage stability is poor as shown in FIGS. 64 to 67. Significant peptide degradation was observed at all conditions apart from the two most favourable (5° C. and −80° C.).

C3C

Non-peptide components (values in brackets indicate concentrations in mM) mannitol/sucrose/thioglycerol/methionine (225:30:46:5)

Characteristics

Tg'=nd

Tg=nd

Tm=nd

Residual moisture=nd

Cake structure: crystalline (not fully)

Retention of thioglycerol is poor. Condensation is visible on vial walls after 5 weeks, especially at 25° C. and 40° C. The thioglycerol is evidently not immobilised within the crystalline cake even at a still higher concentration of sucrose.

Cake appearance is good and so is aesthetically pleasing, but storage stability is poor as shown in FIGS. 68 to 71. Significant peptide degradation was observed at all conditions apart from the two most favourable (5° C. and −80° C.).
C3D
Non-peptide components (values in brackets indicate concentrations in mM) mannitol/sucrose/thioglycerol/methionine/EDTA (245:10:46:5:0.5)
Characteristics
Tg'=nd
Tg=nd
Tm=nd
Residual moisture=nd
Cake structure: crystalline (not fully)

Retention of thioglycerol is poor. Condensation is visible on vial walls after 5 weeks, especially at 25° C. and 40° C. The thioglycerol is evidently not immobilised within the crystalline cake even at a still higher concentration of sucrose.

Cake appearance is good and so is aesthetically pleasing, but storage stability is poor as shown in FIGS. 72 to 75. Significant peptide degradation was observed at all conditions apart from the two most favourable (5° C. and −80° C.).
C3E
Non-peptide components (values in brackets indicate concentrations in mM) mannitol/sucrose/thioglycerol/methionine/EDTA (235:20:46:5:0.5)
Characteristics
Tg'=nd
Tg=nd
Tm=nd
Residual moisture=nd
Cake structure: crystalline (not fully)

Retention of thioglycerol is poor. Condensation is visible on vial walls after 5 weeks, especially at 25° C. and 40° C. The thioglycerol is evidently not immobilised within the crystalline cake.

Cake appearance is good and so is aesthetically pleasing, but storage stability is poor as shown in FIGS. 76 to 79. Significant peptide degradation was observed at all conditions apart from the two most favourable (5° C. and −80° C.). Addition of EDTA does not affect the properties of this composition.
C3F
Non-peptide components (values in brackets indicate concentrations in mM) mannitol/sucrose/thioglycerol/methionine/EDTA (225:30:46:5:0.5)
Characteristics
Tg'=nd
Tg=nd
Tm=nd
Residual moisture=nd
Cake structure: crystalline (not fully)

Retention of thioglycerol is poor. Condensation is visible on vial walls after 5 weeks especially at 25° C. and 40° C. The thioglycerol is evidently not immobilised within the crystalline cake even at a high concentration of sucrose and in the presence of EDTA.

Cake appearance is good and so is aesthetically pleasing, but storage stability is poor as shown in FIGS. 80 to 83. Significant peptide degradation was observed at all conditions apart from the two most favourable (5° C. and −80° C.). Addition of EDTA does not affect the properties of this composition.

Example 4

A formulation based on the findings of Example 1 was tested further for long-term stability. The following formulation (called Thioglycerol "high") was stored for up to one year at 30° C./65% RH:

| Raw material | Function | Nominal concentration[1] | |
|---|---|---|---|
| MLA01, acetate salt | Active ingredient | 50 μM | 73.8 μg/mL |
| MLA03, acetate salt | Active ingredient | 50 μM | 88.6 μg/mL |
| MLA04, acetate salt | Active ingredient | 50 μM | 94.0 μg/mL |
| MLA05, acetate salt | Active ingredient | 50 μM | 101.1 μg/mL |
| MLA07, acetate salt | Active ingredient | 50 μM | 90.3 μg/mL |
| MLA12, acetate salt | Active ingredient | 50 μM | 91.3 μg/mL |
| MLA14, acetate salt | Active ingredient | 50 μM | 84.7 μg/mL |
| D(+) Trehalose dihydrate | Tonicity agent | 270 mM | 102.149 mg/mL |
| 1-Thioglycerol | Reducing agent | 46 mM | 1.514 mg/mL |
| L-Methionine | Antioxidant | 5 mM | 0.746 mg/mL |
| Phosphoric acid | pH adjustment | As required | |

Concentrations are given for the composition when in a liquid state, that is before freeze drying and after reconstitution. An alternative formulation (Thioglycerol "low") was tested under the same conditions, and was identical except in that thioglycerol was present at 14 mM rather than 46 mM. Degradation of peptide was monitored at intervals as shown in FIG. 84. The results indicate that both formulations achieved excellent peptide stability throughout the test period.

The invention claimed is:

1. A method of producing a stable freeze-dried composition comprising the peptides of SEQ ID NOs: 1 to 4, said method comprising:
   a) preparing a composition comprising in solution: (i) trehalose as the sole non-reducing carbohydrate; (ii) thioglycerol; and (iii) the peptides of SEQ ID NOs: 1 to 4; and
   b) freeze-drying the composition resulting from step (a).

2. A method of reconstituting a stable freeze-dried composition comprising the peptides of SEQ ID NOs: 1 to 4, wherein said method comprises reconstituting in solution a freeze-dried composition comprising (i) trehalose as the sole non-reducing carbohydrate, (ii) thioglycerol and (iii) the peptides of SEQ ID NOs: 1 to 4.

3. A stable, freeze-dried composition comprising the peptides of SEQ ID NOs: 1 to 4, thioglycerol and trehalose as the sole non-reducing carbohydrate.

4. A composition according to claim 3 wherein the composition further comprises the peptides of SEQ ID NOs: 84 to 86.

5. The method of claim 1 wherein the composition prepared in step (a) further comprises the peptides of SEQ ID NOs: 84 to 86.

6. The method of claim 2, wherein the composition further comprises the peptides of SEQ ID NOs: 84 to 86.

7. The composition of claim 4, wherein the composition comprises no further peptides.

8. The method of claim 5, wherein the composition prepared in step (a) comprises no further peptides.

9. The method of claim 6, wherein the composition comprises no further peptides.

* * * * *